(12) United States Patent
Bianco-Peled et al.

(10) Patent No.: US 11,096,891 B2
(45) Date of Patent: Aug. 24, 2021

(54) HYBRID MUCO-ADHESIVE DELIVERY SYSTEMS AND USE THEREOF

(71) Applicant: TECHNION RESEARCH & DEVELOPMENT FOUNDATION LIMITED, Haifa (IL)

(72) Inventors: Havazelet Bianco-Peled, Alonei Aba (IL); Avi Schroeder, Binyamina (IL); Shlomit Avidan-Shlomovich, Zurit (IL); Yarden Degani, Yehud (IL); Mor Goldfeder, Nahalal (IL)

(73) Assignee: TECHNION RESEARCH & DEVELOPMENT FOUNDATION LIMITED, Haifa (IL)

( * ) Notice: Subject to any disclaimer, the term of this patent is extended or adjusted under 35 U.S.C. 154(b) by 0 days.

(21) Appl. No.: 16/311,861

(22) PCT Filed: Jun. 21, 2017

(86) PCT No.: PCT/IL2017/050693
§ 371 (c)(1),
(2) Date: Dec. 20, 2018

(87) PCT Pub. No.: WO2017/221251
PCT Pub. Date: Dec. 28, 2017

(65) Prior Publication Data
US 2019/0224111 A1 Jul. 25, 2019

(30) Foreign Application Priority Data
Jun. 21, 2016 (IL) .......................... 246378

(51) Int. Cl.
| | |
|---|---|
| *A61K 9/00* | (2006.01) |
| *A61K 47/36* | (2006.01) |
| *A61K 9/06* | (2006.01) |
| *A61K 33/243* | (2019.01) |
| *A61K 9/127* | (2006.01) |
| *A61K 31/513* | (2006.01) |
| *A61K 31/704* | (2006.01) |
| *A61K 39/395* | (2006.01) |

(52) U.S. Cl.
CPC ............... *A61K 9/006* (2013.01); *A61K 9/06* (2013.01); *A61K 9/127* (2013.01); *A61K 31/513* (2013.01); *A61K 31/704* (2013.01); *A61K 33/243* (2019.01); *A61K 39/39558* (2013.01); *A61K 47/36* (2013.01)

(58) Field of Classification Search
None
See application file for complete search history.

(56) References Cited

U.S. PATENT DOCUMENTS

| | | | |
|---|---|---|---|
| 9,713,591 B2* | 7/2017 | Barenholz | A61K 9/127 |
| 2011/0104052 A1 | 5/2011 | Barnett et al. | |
| 2011/0111033 A1* | 5/2011 | Stover | C08B 37/0084 424/487 |
| 2011/0244029 A1* | 10/2011 | Barenholz | A61K 9/127 424/450 |
| 2014/0234212 A1 | 8/2014 | Goldberg et al. | |

FOREIGN PATENT DOCUMENTS

EP     0356339 A1     2/1990

OTHER PUBLICATIONS

Dini et al (J Microencapsulation, 2003, 20(3), 375-385) (Year: 2003).*
B. Menchicchi et al: "Structure of Chitosan Determines Its Interactions with Mucin", Biomacromolecules, 2014, vol. 15, pp. 3550-3558.
Avi Schroeder et al: "Controlling Liposomal Drug Release with Low Frequency Ultrasound: Mechanism and Feasibility", Langmuir, 2007, vol. 23, pp. 4019-4025.
Mitsugu Tomioka et al: "Effects of Concentration and Degree of Polymerization on the Rheological Properties of Methylcellulose Aqueous Solution", Chemical and Pharmaceutical Bulletin, 1987, vol. 35, No. 6, pp. 2510-2518.
"A Review on Composite Liposomal Technologies for Specialized Drug Delivery"; J.Drug Delivery, vol. 2011, p. 1-19. Mufamadi M.S. et. al. Feb. 8, 2011 (Feb. 8, 2011) p. 1-19, par. 2, 2.1, 3, 3.1, 4.3, 4.5, 6-8.
International Search Report of PCT/IL2017/050693 Completed Sep. 26, 2017; dated Sep. 26, 2017 7 pages.
Written Opinion of PCT/IL2017/050693 Completed Sep. 26, 2017; dated Sep. 26, 2017 6 pages.
S. Al-Musa et al: "Evaluation of parameters involved in preparation and release of drug loaded in crosslinked matrices of alginate"; Journal of Controlled Release, vol. 57, (1999), pp. 223-232.

* cited by examiner

*Primary Examiner* — Celeste A Roney
(74) *Attorney, Agent, or Firm* — The Roy Gross Law Firm, LLC; Roy Gross

(57) ABSTRACT

A composition and method for the administration of therapeutic and/or diagnostic agents is provided. Specifically, a hybrid system, composed of polymer that harbors drug-loaded lipid nanoparticles, and use thereof for the administration of active agents e.g., anti-cancer agents, is provided.

16 Claims, 35 Drawing Sheets

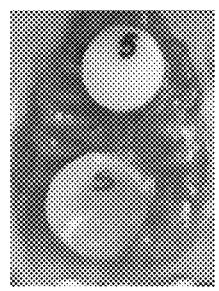
Figure 4D
Figure 4E
Figure 4F
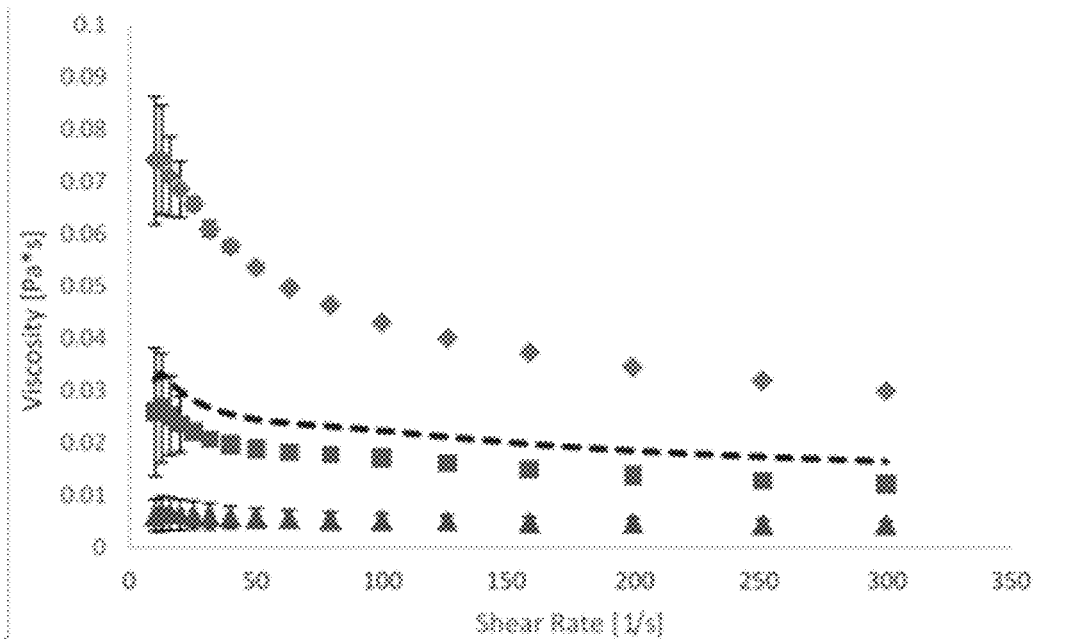
Figure 4G
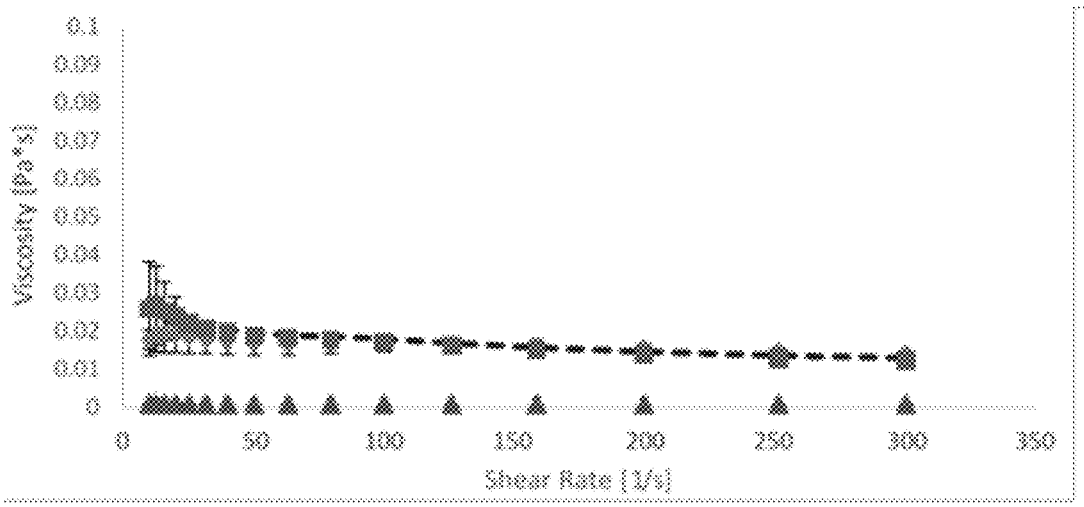

Figure 14B
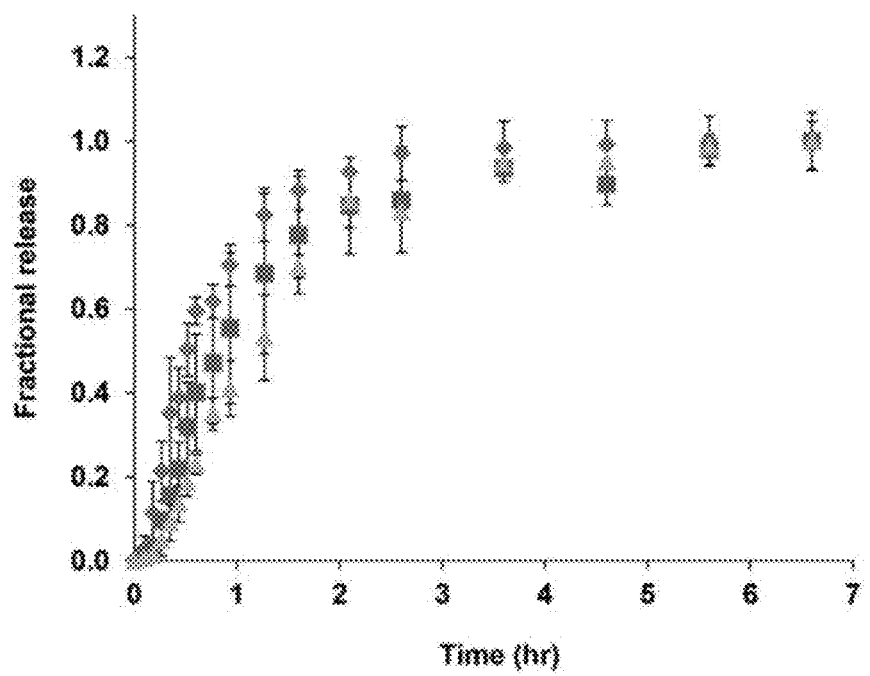
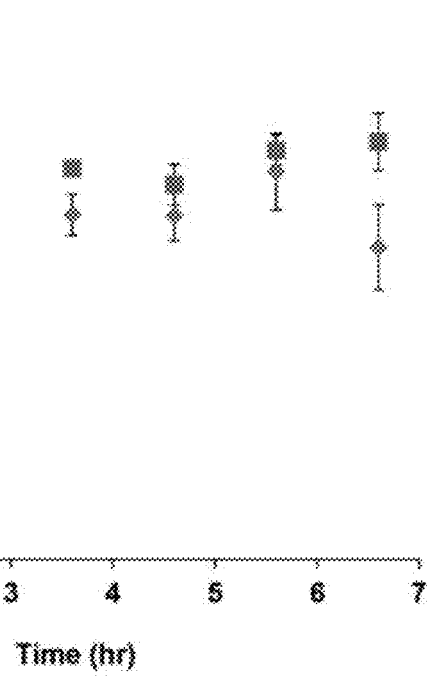
Figure 14D

Figure 14C
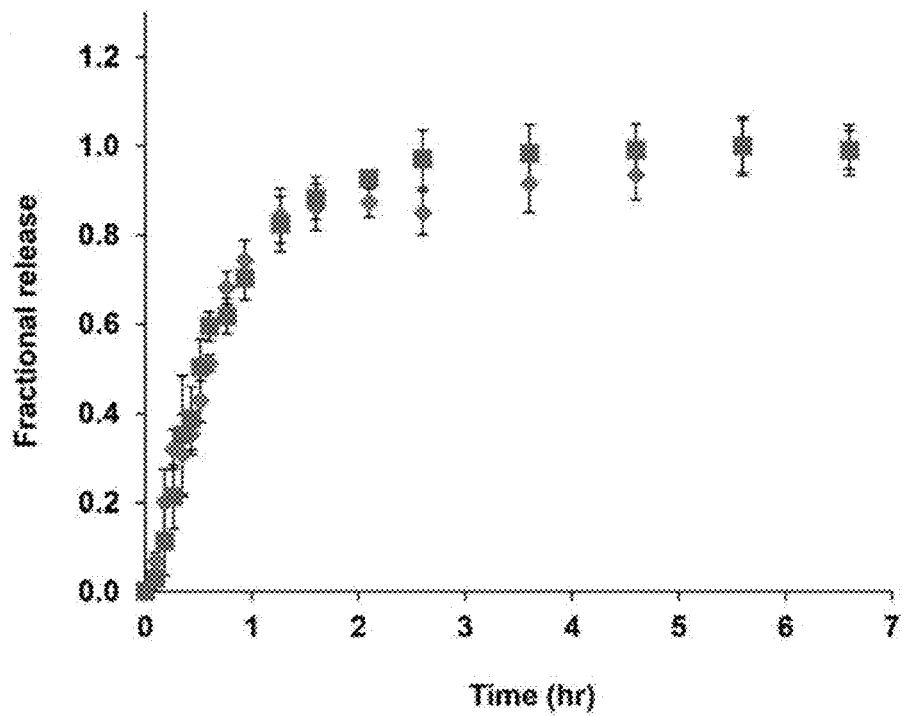
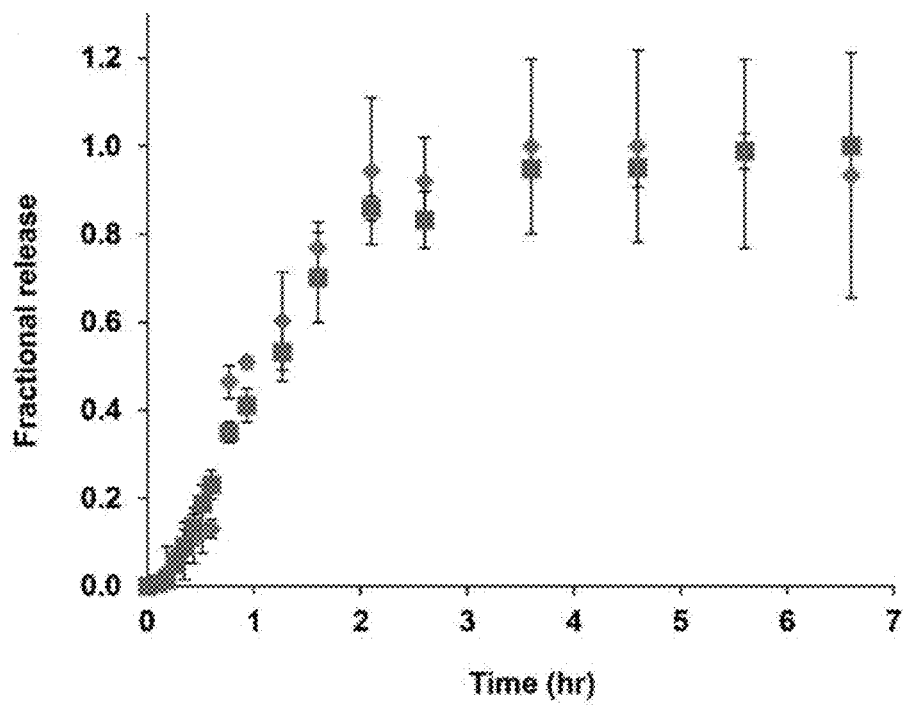
Figure 14E

Figure 23A　　Figure 23B　　Figure 23C　　Figure 23D
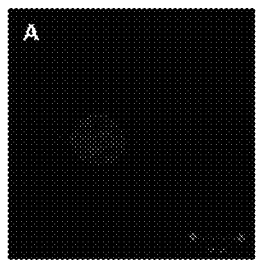 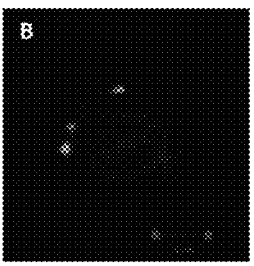 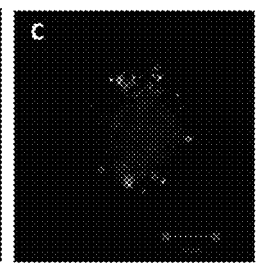 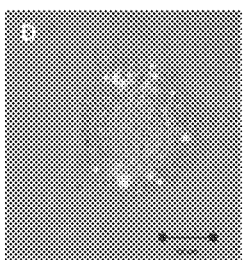
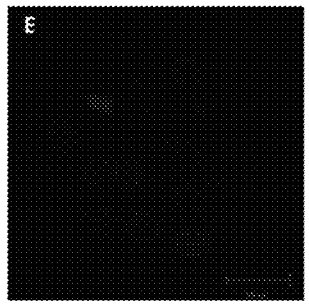 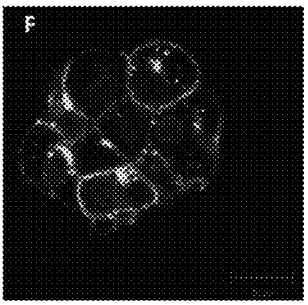 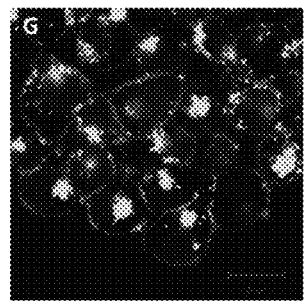
Figure 23E　　Figure 23F　　Figure 23G

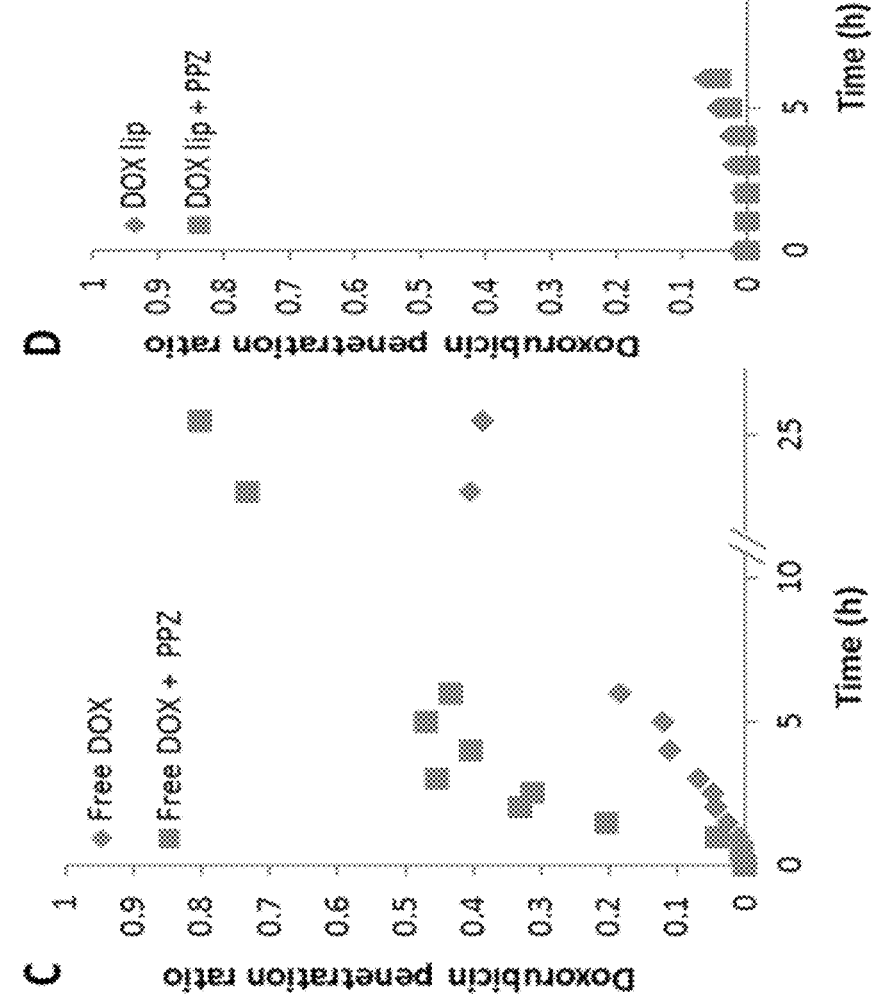
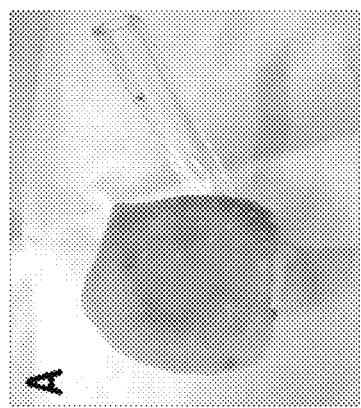
Figure 24A
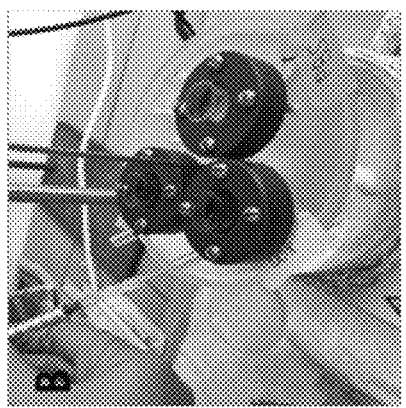
Figure 24B
Figure 24C
Figure 24D

HYBRID MUCO-ADHESIVE DELIVERY SYSTEMS AND USE THEREOF

RELATED APPLICATIONS

This application is a National Phase of PCT Patent Application No. PCT/IL2017/050693 having International filing date of Jun. 21, 2017, which claims the benefit of priority of Israeli Patent Application No. 246378 filed on Jun. 21, 2016. The contents of the above applications are all incorporated by reference as if fully set forth herein in their entirety.

FIELD OF INVENTION

The present invention, in some embodiments thereof, is directed to compositions and methods for transmucosal delivery of agents, e.g., therapeutic agents, including but not limited to the oral cavity.

BACKGROUND OF THE INVENTION

Transmucosal drug delivery involves transport of therapeutic agents through the mucosa; a moist gel layer that lines organs which are exposed on the outer surface of the body, yet are not covered with skin. This mode of delivery offers multiple benefits over oral or intravenous administration, especially when dealing with lesions of the oral cavity. For example, mucoadhesive drug delivery facilitates rapid circulation of drugs in the local capillaries. In addition, it enables enhanced bioavailability, resulting from the ability of mucoadhesive drug delivery to avoid some of the body's natural defense mechanisms and first-pass metabolism.

The mucus layer covers organs such as the oral and nasal routs, and mucins are its main components responsible for its elastic gel-like structure. Mucins are a family of high molecular weight glycoproteins, with a peptide backbone and oligosaccharides as side chains. Their protein backbone is characterized by the presence of repeating sub-domains of serine, threonine, and proline residues. The oligosaccharide side chains are often terminated in sialic acid, sulfonic acid, or L-fructose. As a result, mucins can form electrostatic, hydrophobic, sulfide and H-bonding interactions with other substances, which can lead to mucoadhesion.

Mucoadhesive polymers are capable of attaching to mucosal surfaces, providing prolong residence time of drugs at the site of application. The mechanism of mucoadhesion involves intimate contact of the polymer with the mucus membrane; when dry dosage forms are used, the polymer is activated in the presence of moisture allowing the polymer chains to penetrate into the mucus layer to form electrostatic, van-der walls and hydrogen bond interactions. The most widely investigated group of mucoadhesive polymers are commercially available hydrophilic macromolecules such as poly(acrylic) acid, cellulose, alginate and chitosan. These polymers, often referred to as first generation mucoadhesive polymers, are capable of creating multiple non-covalent bonds with the mucus membrane. The strength of these interactions depends on the characteristics of the polymer, as well as environmental conditions such as pH and ionic strength. For example, mucoadhesive properties of polymers can vary depending on the molecular weight, flexibility of the polymeric chains, hydrogen bonding capacity, cross-linking density, charge, concentration, or hydration degree of the polymer. In addition, the saliva environment as the dissolution medium affects the behavior of polymers. For example, the saliva pH (6.4-6.8) and its salts content may lead to a different ionization state of an ionic polymer, and eventually may affect the polymer's viscosity, hydration capacity, flexibility and contact time with the mucin.

Natural polysaccharides are particularly attractive as drug delivery matrixes because they are economical, readily available, biodegradable, biocompatible and non-toxic. Generally, they are linear high molecular weight polymers containing hydrophilic functional groups, often with ionic charges; consequently, they are water soluble so their bioadhesive properties can be utilized in transmucosal oral drug delivery. The mucoadhesive polymeric forms may include tablets, patches, films, hydrogels and pastes.

Oral cancer, as a non-limiting example, is the sixth most prevalent cancer worldwide. Specifically, squamous cell carcinoma (SCC) accounts for over 90% of all head and neck cancers, and the overall survival rates are only 40-50%. Over the past decade, incidences of oral cancers have risen by 35%, with limited treatment modalities. Administering anti-cancer agents in close proximity to cancerous lesion has proven clinically effective when dealing with head and neck tumors. However, no drug delivery system of anti-cancer agents, for controlled administration to the oral cavity, exists in the clinic.

There is an unmet need for compositions and methods for the transmucosal delivery of agents, e.g., therapeutic agents, such as in a sustained release manner. Further, for transmucosal delivery to the oral cavity, there is a need for compositions which are stable under dilution, shear flow and physiological conditions of the saliva fluids.

SUMMARY OF THE INVENTION

The present invention provides compositions and methods useful for the transmucosal administration of therapeutic and/or diagnostic agents.

The present invention presents for the first time, inter alia, a hybrid system, composed of polymer (e.g., alginate) that harbors drug-loaded lipid nanoparticles, and use thereof for the administration of active agents e.g., anti-cancer agents for treating oral cancers.

In one aspect, the present invention provides a composition comprising a muco-adhesive polymer and a nano-carrier, wherein the nano-carrier is encapsulated within the muco-adhesive polymer, and the nano-carrier comprising at least one therapeutic or diagnostic agent.

In some embodiments, at least 0.5% to 60%, by total volume of said muco-adhesive polymer, are crosslinked via a crosslinking agent.

In some embodiments, the disclosed composition is in the form of a muco-adhesive matrix, wherein the cross-linked muco-adhesive polymer defines a network having internal pores.

In some embodiments, the internal pores may be e.g., 10 nm, 20 nm, 50 nm, 100 nm, 150 nm, 200 nm, 500 nm, or 1000 nm, by average diameter size, including any value therebetween.

In some embodiments, the one or more nano-carriers are entrapped within the internal pores.

In some embodiments, the muco-adhesive matrix is characterized by a first surface and a second surface, wherein a backbone of the muco-adhesive polymer is substantially not crosslinked within the portion defining the first surface.

The low cross-linking density (e.g., below 0.5%, or 0.1%) allows to maintain the adhesiveness property of the polymer.

In some embodiments, the composition further comprises a blocking agent, wherein the blocking agent is attached to the second surface, and wherein the blocking agent is adapted to inhibit the one or more nano-carriers from passing therethrough.

In some embodiments, the one or more nano-carriers further comprises a coupling agent attached thereto.

In some embodiments, the coupling agent is derived from polyethylene glycol (PEG).

In some embodiments, at least 10% of the nano-carriers are linked to the muco-adhesive polymer via the coupling agent.

In some embodiments, the blocking agent is selected from the group consisting of polymeric and non-polymeric materials.

In some embodiments, the crosslinking agent is an ion selected from the group consisting calcium, barium or a combination thereof.

In some embodiments, an average diameter of the internal pores is at least 10% smaller than an average diameter of the one or more nano-carriers.

In some embodiments, the muco-adhesive polymer is selected from alginate and chitosan. In some embodiments, the muco-adhesive polymer is bioerodible.

In some embodiments, the nano-carrier is a lipid-based particle. In some embodiments, the lipid-based particle is a liposome or a micelle.

In some embodiments, the nano-carrier has an average diameter of about 50-5000 nanometers. In some embodiments, the nano-carrier has an average diameter of about 100-500 nanometers.

In some embodiments, the molar ratio of nano-carrier and polymer is 1:100 to 1:800. In some embodiments, the molar ratio of nano-carrier and polymer of 1:120 to 1:600.

In some embodiments, the agent is a therapeutic agent having a therapeutic effect in the treatment of a disease or disorder associated with the oral cavity.

In some embodiments, the agent is a diagnostic agent selected from the group consisting of: chromophores, fluorescent compounds, phosphorescent compounds, heavy metal clusters, radioactive labeling compounds and contrast agents.

In another aspect, the present invention provides a polymeric formulation comprising a plurality of the disclosed composition. In some embodiments, the polymeric formulation is a sustained-release formulation applicable to mucous membrane. In some embodiments, the mucous membrane is oral cavity mucous membrane.

In some embodiments, the molar concentration of the nano-carriers in the composition is about 10-200 millimolar (mM). In some embodiments, the concentration of the nano-carriers in the composition is about 50-150 millimolar (mM).

In another aspect, the present invention provides a kit for forming a drug-eluting bioadhesive matrix comprising: a formulation comprising a muco-adhesive polymer, and a formulation comprising one or more nano-carriers, wherein the nano-carrier comprises at least one therapeutic or diagnostic agent.

In some embodiments, the kit further comprises a composition comprising one or more crosslinking agents.

In some embodiments, the kit further comprises a composition comprising one or more blocking agents.

In another aspect, the present invention provides a method for preparing a drug-eluting bioadhesive matrix on a mucous membrane, the method comprising performing the following steps in a predetermined order:

incorporating a composition (e.g., a paste or a formulation) comprising a muco-adhesive polymer on a mucous membrane.

introducing a composition (e.g., a paste or a formulation) comprising one or more nano-carriers on the mucous membrane (or into the composition comprising a muco-adhesive on the paste on a mucous membrane), wherein the nano-carrier comprises a therapeutic or diagnostic agent;

introducing a composition comprising one or more crosslinking agents into the polymer, thereby forming a polymeric drug-eluting bioadhesive matrix.

In some embodiments, the method further comprises a step of introducing a composition (e.g., solution or paste) comprising a blocking agent onto the matrix.

In another aspect, the present invention provides a bioadhesive matrix, formed by the disclosed method in any embodiment thereof.

Further embodiments and the full scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

(FIG. 1B).

FIGS. 4A-H present characterization of chitosan-related product: $^1$H NMR spectra of: a. chitosan b. chitosan-PEGAc at 25° C. in 2% acetic acid-d4 (FIG. 4A); a bar graph showing the maximum detachment strength (MDS) of the dry compressed polymer tablets from fresh intestine surfaces (FIG. 4B); a photograph showing pulling a chitosan-PEGA (10) tablet from fresh small intestine surface during a tensile test (FIG. 4C) (**) refers to statistically significant difference (p<0.01); photographs showing chitosan (FIG. 4D) and chitosan-PEGA(10) samples after 30 minutes of experiment (FIG. 4E); Graphs showing viscosity vs. shear rate for chitosan-PEGA(10), mucin (5%) and their mixture (FIG. 4F) and chitosan-PEGA(0.7), mucin (5%) and their mixture in 0.1 M PBS at 37° C. (FIG. 4G). Symbols: (♦) chitosan-PEGA/mucin mixture, (■) mucin and (▲) chitosan-PEGA. Dashed line represents summation of the viscosity of chitosan-PEGA and that of mucin (5%). FIG. 4H presents a scheme showing the synthesis of chitosan-PEGA.

(FIG. 10A) and a graph showing the fractional release of liposome vs. time into 5% dextrose solution or 0.01M PBS, pH=6.8, at 37° C.; (♦) liposome release to 5% dexstrose, and (■) liposome release to 0.01M PBS pH=6.8 (FIG. 10B).

FIGS. 11A-B presents graphs showing the fractional release of liposomes vs. time: from different alginate hydrogel compositions into 0.01M PBS, pH=6.8, at 37° C. (♦) 1%, (▲) 3%-w/v alginate within the hydrogel, (■) 1.33% w/v alginate in concentrated hydrogel, (x)++1% w/v alginate in high cross linked hydrogel (FIG. 11A), and fractional release of liposomes from alginate hydrogels with different crosslinker compositions (♦) alginate hydrogels cross-linked with 20 mM $CaCl_2$; (■) alginate hydrogels cross-linked with 19.5 mM $CaCl_2$ and 0.5 mM $BaCl_2$ mixture; (▲) alginate hydrogels cross-linked with 19.5 mM $CaCl_2$ and 2 mM $SrCl_2$ mixture; (o) alginate hydrogels cross-linked with 19.5 mM $CaCl_2$ and 1 mM $BaCl_2$ in simulated saliva buffer vs. time, pH=6.8, at 37° C. (FIG. 11B). FIG. 11C presents a scheme of an exemplary hybrid polymer/liposomes system as discloses herein.

FIGS. 14A-E present a graph showing the fractional release of liposome vs. time from different alginate pastes: into 0.01M PBS, pH=6.8, at 37° C. (♦) 4% w/v alginate paste, (▲) 4% w/v alginate-SH paste, and (■) 30% w/v alginate-PEGAc paste (FIG. 14A); and into simulated saliva buffer, pH=6.8, at 37° C. (♦) 3% alginate paste; (■) 4% alginate paste; (▲) 5% alginate paste. Fractional release of liposome and polymer chains vs. time into saliva simulated buffer, pH=6.8, at 37° C. (♦) liposome release, (■) polymeric chain release (FIG. 14B); 3% Alginate paste (FIG. 14C); 4% Alginate paste (FIG. 14D); 5% Alginate paste (FIG. 14E) (Same symbols were used in all graphs).

(FIG. 18B).

FIG. 22A); comparison between fluorescence intensity of Cetuximab binding to oral cancer cells, CAL-27 and normal cells, NHDF (FIG. 22B); flow cytometry chromatograms are presented as well for CAL-27 (FIG. 22C) and NHDF (FIG. 22D), and chromatograms of Cetuximab loaded liposomes immunostaining of CAL-27 cells (FIG. 22E).

FIGS. 23A-G present confocal microscopy images of cancer cells to which protein loaded liposomes were delivered. The nucleus (blue) was stained using Hoechst. Delivery of sfGFP (green) loaded liposomes into SCC 7 cells was examined in comparison to delivery of empty liposomes (FIG. 23A), and delivery of free sfGFP (FIG. 23B); The delivery of sfGFP loaded liposomes into the cells is observed (FIG. 23C), as can be seen also with the bright field image (FIG. 23D). Delivery of labeled Cetuximab loaded liposomes (cyan) to CAL 27 cells was examined in comparison to delivery of labeled isotype control loaded liposomes (FIG. 23E); Delivery of cetuximab loaded liposomes was observed mostly on the membrane after 2 hr incubation (FIG. 23F) and also inside the cell after overnight incubation (FIG. 23G). Figures A-D: bar is 10 µm; Figures E-G: bar is 20 µm.

FIGS. 24A-D present doxorubicin penetration assessment using Franz Cell system. The top tongue layer used for the experiment as it is placed on the donor cell of the Franz cell system (FIG. 24A); The complete Franz cell system as it is prepared for an experiment testing three samples simultaneously (FIG. 24B); Doxorubicin penetration ratio over time in free doxorubicin (♦) compared to free doxorubicin with the permeation enhancer phenylpiprazin (PPZ) (■) (FIG.

24C), and in doxorubicin loaded liposomes (♦) compared to these liposomes with PPZ (■) (FIG. 24D).

Figure 25:
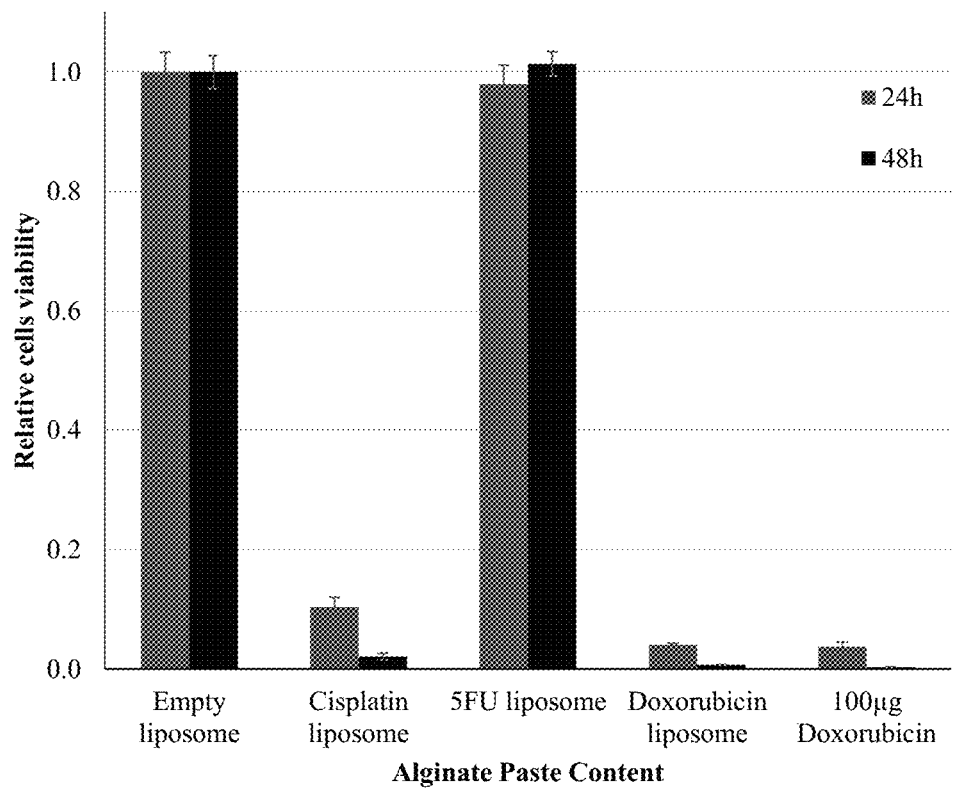

FIG. 25 presents in vitro efficacy of hybrid system: cell viability of CAL-27 cells after 24 and 48 hr in the presence of different alginate pastes containing empty liposomes, cisplatin loaded liposomes, 5FU loaded liposomes, doxorubicin loaded liposomes and free doxorubicin (100 μg). Cell viability was determined using the CellTiter-Glo® assay (left bar: 24 h, right bar: 48 h)

Figures 26A, 26B:
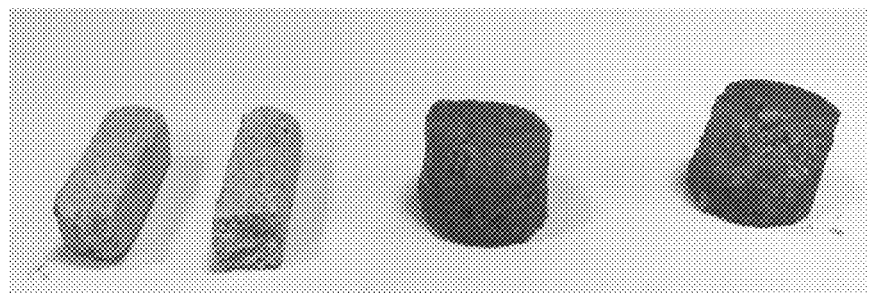

FIGS. 26A-B present photographs showing mice food for pre-clinical model. Normal pelleted food (FIG. 26A) and agar-based soft food (FIG. 26B)

Figure 27:
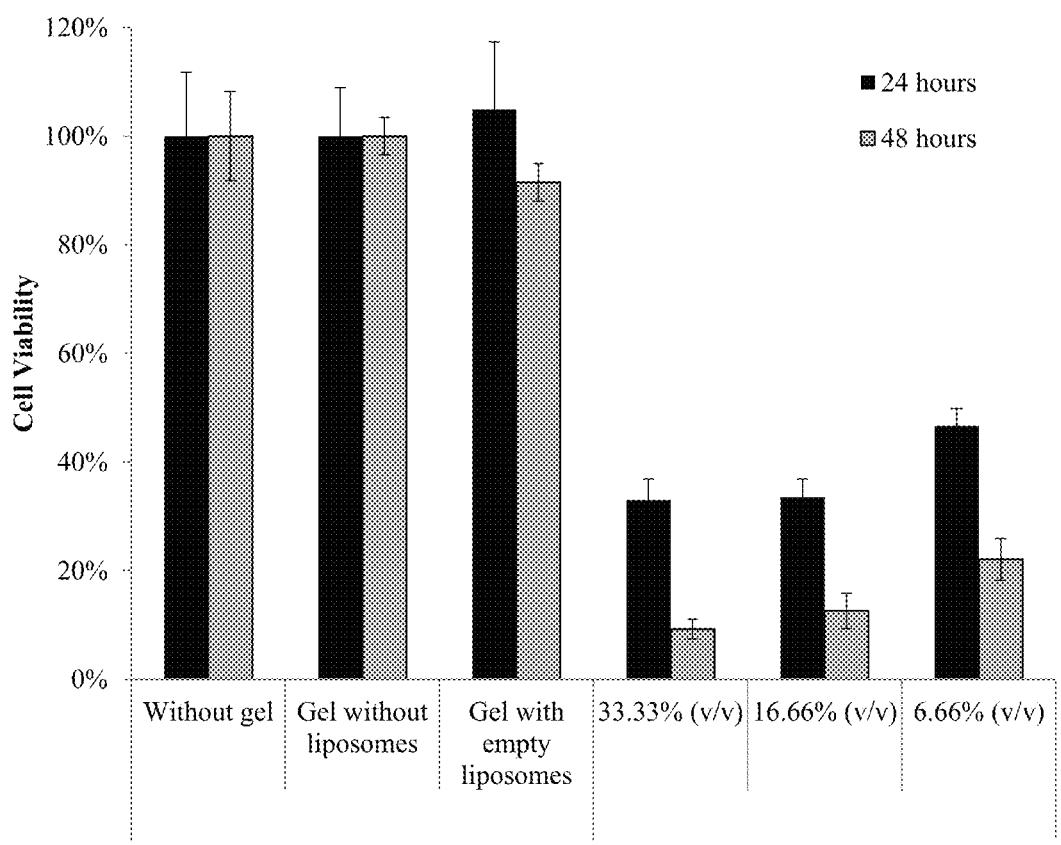

FIG. 27 presents bar graphs showing the cell viability of CAL-27 cells after 24 and 48 hr in the presence of alginate gel formulations with and without drug loaded liposomes. Liposomes containing Doxorubicin (400 μg/mL) were examined. Cell viability was determined using the MTT assay.

DETAILED DESCRIPTION OF THE INVENTION

The present invention provides compositions and methods useful for transmucosal delivery of at least one active agent (e.g., therapeutic agents, or diagnostic agents or combinations thereof).

Before explaining at least one embodiment of the invention in detail, it is to be understood that the invention is not necessarily limited in its application to the details set forth in the following description or exemplified by the Examples. The invention is capable of other embodiments or of being practiced or carried out in various ways.

According to an aspect of some embodiments of the present invention, there is provided a composition comprising a muco-adhesive polymer and a nano-carrier, wherein the nano-carrier is encapsulated within the muco-adhesive polymer, and wherein the nano-carrier comprises at least one agent selected from a therapeutic agent and a diagnostic agent.

In some embodiments, the term "muco-adhesive" refers to a feature of a substance (e.g., a formulation or a matrix) having improved adherence to a mucus tissue. In some embodiments, the term "muco-adhesive" means a material that will adhere to mucus and thus prolong the residence of the formulation.

In some embodiments, at least 0.1%, at least 0.2%, at least 0.5%, at least 1%, at least 2%, at least 3%, at least 4%, at least 5%, at least 6%, at least 7%, at least 8%, at least 9%, at least 10%, at least 20%, at least 30%, at least 40%, at least 50%, at least 60%, or at least 70%, by total volume of the muco-adhesive polymer is crosslinked. In some embodiments, at most 75%, at most 70%, at most 65%, at most 60%, at most 55%, at most 50%, at most 45%, at most 40% at most 35%, at most 30%, at most 25%, at most 20%, at most 15%, at most 10%, by total volume of the muco-adhesive polymer is crosslinked.

In some embodiments, the present invention provides a delivery vehicle for any one of a drug and a diagnostic agent (herein "agent") that is muco-adhesive. The vehicle comprises vesicles or carriers such as nano-carriers (e.g., liposomes) encapsulated within polymers having one or more muco-adhesive groups or regions. The nano-carriers can be loaded with an agent, or the agent can be otherwise carried by the nano-carriers. The incorporation of the agent within the vesicle may be by any means, whether in the interior or membrane of the vesicle.

In some embodiments, "vesicle" and "carrier" are synonymous and refer to a particle having a hollow core or a core filled with a material to be delivered or released. Vesicles may have a spherical or other shape. They may have a unilamellar or multilamellar membrane. In some embodiments, the disclosed carriers are nano-carriers, such as in the range of about 50 nanometers to 500 nanometers.

Non-limiting exemplary vesicles are liposomes. In some embodiments, liposomes refer to vesicles with an internal aqueous core surrounded by a lipid bilayer/s, and are widely used as drug carriers. This is greatly due to their unique characteristics such as good biocompatibility, low toxicity, lack of immune system activation, and the ability to incorporate both hydrophobic and hydrophilic compounds.

In some embodiments, combining mucoadhesion with the advantages of liposomal drug delivery, such as a sustained release rate, allows protecting pharmaceuticals from chemical and enzymatic degradation, and improving drug bioavailability, hence providing a powerful method for non-invasive hybrid (polymer/lipid) drug delivery vehicles.

The drug delivery vehicle can be used for delivery of an agent to an area of the body having a mucous membrane, such as, but not limited to, the oral cavity. For example, the delivery vehicle can be designed for use in oral, buccal, nasal, rectal and vaginal routes for both systemic and local effects.

Matrix, Hydrogel and Paste:

In some embodiments, the disclosed composition or the disclosed polymeric material is in the form of a muco-adhesive matrix, wherein the cross-linked muco-adhesive polymer defines a network. In some embodiments, the network is further characterized by internal pores.

In some embodiments, one or more nano-carriers are entrapped within the network e.g., within the internal pores.

In some embodiments, the disclosed polymeric material is characterized by a first surface and a second surface, wherein the muco-adhesive polymer in/on the first surface is substantially (e.g., less than 0.01%, by total volume) not crosslinked.

In some embodiments, the first surface is tissue adhesive, i.e., is adapted to be applied on a surface of a biological object, e.g., oral mucosa, and to allow releasing therefrom the therapeutic agent and/or the nano-carrier at a defined rate.

In some embodiments, the composition further comprises a blocking agent. In some embodiments, the blocking agent is attached to the second surface. In some embodiments, the blocking agent is adapted to be attached to the second surface. In some embodiments, the blocking agent is adapted to maintain the one or more nano-carriers entrapped within the network, while substantially blocking the nano-carriers from passing thereto. That is, normally, the blocking agent will function by physically blocking at least a portion of the network in order to inhibit passage therethrough of the nano-carrier or the therapeutic agent. For topical delivery, the blocking agent will usually be selected to provide a substantially constant inhibition of diffusion of active substance and/or nano-carriers from the matrix, such as to the oral cavity.

In some embodiments, an average diameter of the internal pores is at least 5%, at least 10%, at least 20%, or at least 30% smaller than an average or a median diameter of the one or more nano-carriers.

In some embodiments, the blocking agent is selected from polymeric and non-polymeric materials.

In some embodiments, the disclosed composition or the disclosed polymeric material is in the form of a hydrogel.

As used herein, the term "hydrogel" refers to a three-dimensional fibrous network containing from about 50%, or from about 80%, and up to 99.9% (by mass) water. A hydrogel can be regarded as a material which is mostly water, yet behaves like a solid or semi-solid due to a three-dimensional crosslinked network within the liquid, made of natural and/or synthetic polymeric chains. In some embodiments, a hydrogel may contain polymeric chains of various molecular weights in the range of $10^3$ to $10^6$ gr/mole and chemical compositions which may stem from monomers, oligomers, block-polymeric units, which are inter-connected (crosslinked) by chemical bonds.

In some embodiments, the term "chemical bond" refers to a covalent bond. In some embodiments, the term "chemical bond" refers to a hydrogen bond. In some embodiments, the term "chemical bond" refers to one or more from ionic, complex, or metallic bonds.

As used herein, the term "polymer", or any grammatical derivative thereof, describes an organic substance composed of a plurality of repeating structural units (monomeric units) covalently connected to one another.

The polymers used in the present invention may be a copolymer with one or more other monomers unless they do not undesirable effect on the physio-chemical properties of the polymers, and include also a polymer crosslinked by an appropriate crosslinking agent. When the polymers are copolymerized with not more than 30% by mole of the other monomer(s), the physio-chemical properties of the polymers are not affected, and hence, such copolymers can be used in the present invention.

In some embodiments, the polymer is selected from non-natural polymers. In some embodiments, the polymer is selected from natural polymers.

In some embodiments, the polymer is hydrophilic or water-swellable gel-type polymer material selected from polysaccharides.

For example, in some embodiments, the polymer is material selected from, without being limited thereto, pectin, chitosan, alginate, cellulose, or any derivative thereof.

In some embodiments, the polymer is selected from, without being limited thereto polyvinyl alcohol, polyethylene glycol, and polypropylene vinyl pyrrolidone, or any derivative thereof.

In some embodiments, the polymer is a biodegradable. The term "biodegradable" describes a substance which can decompose under physiological and/or environmental conditions into breakdown products. Such physiological and/or environmental conditions include, for example, hydrolysis (decomposition via hydrolytic cleavage), enzymatic catalysis (enzymatic degradation), and mechanical interactions. This term typically refers to substances that decompose under these conditions such that e.g., 50 weight percent of the substance decompose within a time period shorter than one year.

The term "biodegradable" as used in the context of embodiments of the invention, also encompasses the term "bioresorbable", which describes a substance that decomposes under physiological conditions to break down products that undergo bioresorption into the host-organism, namely, become metabolites of the biochemical systems of the host-organism.

The polymer of the invention may comprise a combination of bio-stable polymers and/or biodegradable polymers.

In some embodiments, the polymeric chains are inter-connected (crosslinked) by ions. In some embodiments, the polymeric chains are inter-connected by calcium ions. In some embodiments, the polymeric chains are inter-connected by barium ions. In some embodiments, the polymeric chains are inter-connected by strontium ions. In some embodiments, the polymeric chains are inter-connected by any combination of the above-mentioned ions. Other non-limiting examples of crosslinker (e.g., for alginate) are selected from sodium tripolyphosphate, phosphorus oxychloride or carboxylic acids. In some embodiments, the polymeric chains are inter-connected by a therapeutically acceptable cross-linker such as an ion.

In some embodiments, the barium ions, calcium ions, or any combination thereof are at a defined concentration so as to allow a controlled release of the liposome(s) to the medium, as further exemplified hereinbelow.

In some embodiments, the ions (e.g. barium or calcium) are at a concentration (in mM) of e.g., 0, 0.01, 0.1, 0.2, 0.3, 0.4, 0.5, 0.6, 0.7, 0.8, 0.9, 1, 1.2, 1.4, or 1.5, including any value and range therebetween.

In some embodiments, "crosslinked" and/or "crosslinking", and any grammatical derivative thereof refers generally to a chemical process or the corresponding product thereof in which two chains of polymeric molecules are attached by bridge(s) (termed: "cross-linker", also referred to as: "cross-linking agent") composed of an element, a group or a compound, which join certain carbon atoms of the chains by primary chemical.

In some embodiments, the cross-linker is selected from the group consisting of:

gluteraldehyde, formaldehyde, benzoquinone, epichlorohydrin (e.g., for chitosan or alginate).

In exemplary embodiments, the cross-linker is genipin.

In some embodiments, the macromolecules are characterized by a desired friction and/or hydrophility that fits surface properties, of e.g., mucoadhesion in the oral cavity. By "fits surface properties" it is meant that the polymer, either in the form of paste or in the form of hydrogel, adheres to the mucosa, for example by formation of inter-chain bridges of the polymeric functional group and mucin glycoproteins. As used herein, the term "paste", relates to a viscous thick liquid. In some embodiments, the crosslinking percent in the paste is less than e.g., 1%, 0.5%, or 0.1%.

Hence, in some embodiments, the disclosed macromolecules are mucoadhesive polymers.

In some embodiments, the hydrogel (or the paste) comprises 1, 2, 3, 4, or 5 regions, each region being characterized by one or more from: having a polymeric matrix which is capable of beholding and releasing liposomes in a desired rate; or serving as an external sealant layer which prevents the liposome from leaking from the hydrogel to the tissue.

In some embodiments, the macromolecules include acrylated polymer. In some embodiments, the disclosed macromolecules include gelatin. In some embodiments, the macromolecules include alginate. In some embodiments, the macromolecules include alginate methacrylate. In some embodiments, the macromolecules include chitosan or any derivative thereof.

In some embodiments, the macromolecules include chitosan methacrylate. In some embodiments, the macromolecules include glycol chitosan. In some embodiments, the macromolecules include thiol modified chitosan. In some embodiments, the macromolecules include glycol chitosan methacrylate. In some embodiments, the macromolecules include hyaluronic acid. In some embodiments, the macromolecules include hyaluronic acid methacrylate. In some embodiments, the macromolecules include non-crosslinked natural or synthetic polymeric chains and the likes. Further non-limiting exemplary macromolecules include polyethylene glycol diacrylate (optionally conjugated to e.g., alginate), pectin, chitosan or any other hydrophilic polymer. In some embodiments, the macromolecules are hydrophilic polymers, each bearing at least one non-saturated end or pendant group.

In some embodiments, the macromolecules include macromolecule (alginate) and ion (e.g., calcium ion), in a defined ratio. In some embodiments, the ratio of $Ca^{2+}$: alginate is selected from 300:1, 252:1, 200:1, 100:1, or 50:1, including any value and ratio therebetween.

In some embodiments, the disclosed composition comprises liposome and macromolecule (non-liposomal polymer) in a ratio of (liposome:polymer): 400:1, 350:1, 300:1, 250:1, 200:1, 150:1, or 100:1, including any value and range therebetween.

In some embodiments, the disclosed composition comprises macromolecule (non-liposomal polymer) in a concentration of (w/v %) 0.25, 0.5, 0.75, 1, 1.25, or 1.5, including any value and range therebetween.

In some embodiments, the amount of such non-crosslinked additives is small, and does not exceed e.g., 100 mg in 1 ml of the hydrogel-forming precursor solution.

In some embodiments, the polymeric composition is in the form of a paste (non-hydrogel structure), i.e., in the form of viscous solution or suspension.

The term "viscous solution or suspension" is used to describe solutions or suspensions of polymers according to the present invention wherein the solution has a viscosity which is greater than about 1 centipoises unit and is less than about 500,000 centipoises units.

Viscous solutions or suspensions of polymers according to the present invention at viscosities approaching the high end of the range of viscosities may be indistinguishable from gels at the low end of a viscosity range.

In some embodiments, the paste is substantially devoid of crosslinking bonds.

In some embodiments, the paste or hydrogel are characterized by a desired "hardness" property. Exemplary hardness properties hardness properties are the indention load deflection (ILD) or indention force deflection (IFD) and is measured e.g., in accordance with ASTM D-3574.

In some embodiments, the paste comprises a crosslinker (e.g., ions) in a ratio (crosslinker to macromolecule (non-liposomal polymer)) of 100:1, 75:1, 50:1, or 25:1, including any value and range therebetween.

In some embodiments, the paste comprises a liposome in a ratio (liposome to macromolecule (non-liposomal polymer)) of 800:1, 750:1, 700:1, 650:1, 600:1, 550:1, or 500:1 including any value and range therebetween.

In some embodiments, the paste comprises a macromolecule(s) (non-liposomal polymer) at a concentration of (w/v %) 1, 2, 3, 4, 5, 6, 7, 8, 9, or 10, including any value and range therebetween.

In some embodiments, the hydrogel/paste is dispersed in a liquid. In some embodiments, the liquid further comprises a stabilizer so as to allow keeping the hydrogel in a swollen form. In some embodiments, the liquid is water. In some embodiments, the liquid is characterized by a defined pH. In some embodiments, the defined pH range is in the acidic range, i.e. lower than 7, e.g., 5, 6, 6.9, including any value therebetween. In some embodiments, the defined pH range is about 7.

Therapeutic and Diagnostic Agents

In some embodiments, the composition further comprises an active agent such as a therapeutic agent or a diagnostic agent (e.g., a labeling agent). In some embodiments, the agent is attached to and/or encapsulated within the carrier (e.g., liposome).

As used herein, the phrase "a therapeutically active agent" describes a chemical substance, which exhibit a therapeutic activity when administered to a subject. As used herein, the phrase "biologically active agent", or "bioactive agent", describes a chemical substance, which exhibits a biological or physiological activity in an organism.

As used herein, a "therapeutically effective amount" or "an amount effective" refers to an amount effective, at dosages and for periods of time necessary, to achieve the desired therapeutic result. The therapeutically effective amount of the therapeutic agent will depend on the nature of the disorder or condition and on the particular agent and can be determined by standard clinical techniques known to a person skilled in the art.

As used herein, the phrase "labeling agent" refers to a detectable moiety or a probe and includes, for example, chromophores, fluorescent compounds, phosphorescent compounds, heavy metal clusters, and radioactive labeling compounds, as well as any other known detectable moieties. Also included are contrast agents, e.g., a magnetic resonance imaging (MRI) contrast agent, a computed tomography (CT) contrast agent, a single photon emission computed tomography (SPECT) contrast agent, a positron emission tomography (PET) contrast agent, a bioluminescence (BL) contrast agent, an optical contrast agent, an X-ray contrast agent, and an ultrasonic contrast agent.

The phrase "radioactive agent" describes a substance (i.e. radionuclide or radioisotope) which loses energy (decays) by emitting ionizing particles and radiation. When the substance decays, its presence can be determined by detecting the radiation emitted by it. For these purposes, a particularly useful type of radioactive decay is positron emission. Exemplary radioactive agents include $^{99m}Tc$ $^{18}F$, $^{131}I$ and $^{125}I$.

Non-limiting examples of therapeutically active agents that can be beneficially used in embodiments of the present invention include, without limitation, one or more of an agonist agent, an amino acid agent, an analgesic agent, an antagonist agent, an antibiotic agent, an antibody agent, an antidepressant agent, an antigen agent, an antihistamine agent, an anti-hypertensive agent, an anti-inflammatory drug, an anti-metabolic agent, an antimicrobial agent, an antioxidant agent, an anti-proliferative drug, an antisense agent, a chemotherapeutic drug, a co-factor, a cytokine, a drug, an enzyme, a growth factor, a heparin, a hormone, an immunoglobulin, an inhibitor, a ligand, a nucleic acid, an oligonucleotide, a peptide, a phospholipid, a prostaglandin, a protein, a toxin, a vitamin and any combination thereof.

The active agents to be contained in the vesicles of the present invention include all medicaments useful for oral diseases, teeth diseases and also systemic diseases, for example, analgesics and anti-inflammatory agents (e.g. indometacin, ibuprofen), mouth disinfectants (e.g. chlorohexidine hydrochloride, hexylresorcine), enzymes (e.g. lysozyme chloride, dextranase, kallikrein), coronary vasodilators (e.g. nitroglycerin, isosorbide dinitrate, nifedipine), antiasthmatics (e.g. disodium cromoglycate), antibiotics (e.g. penicillins, erythromycin), chemothera-peutics (e.g. sulfathiazole, nitrofurazone), local anesthetics (e.g. benzocaine), cardiotonics (e.g. digitalis, digoxin), antitussives and expectorants (e.g. codeine phosphate, isoproterenol hydrochloride), agents affecting digestive organs (e.g. water-soluble azulene (sodium azulene sulfonate), vitamin U), antihistamins (e.g. diphenhydramine hydrochloride, chlorpheniramine maleate), antiinflammatory steroids (e.g. prednisolone, triamci-nolone), antifungal agents (e.g., miconazoel, nystatin and amphotericin), hemostatics, sexual hormones, sedatives, antitumor agents, or the like.

In some embodiments, the therapeutically active agent is an anti-cancer drug. The term "cancer" as used herein, refers to a disease or disorder resulting from the proliferation of oncogenically transformed cells. Examples of particular cancers that may be treated according to the method of the present invention include oral cancer, such as oral squamous cell carcinoma and oral pharyngeal cancer.

The phrase "anticancer agent" or "anticancer drug", as used herein, describes a therapeutically active agent that directly or indirectly kills cancer cells or directly or indirectly inhibits, stops or reduces the proliferation of cancer cells. Anti-cancer agents include those that result in cell death and those that inhibit cell growth, proliferation and/or differentiation. In some embodiments, the anti-cancer agent is selectively toxic against certain types of cancer cells but does not affect or is less effective against normal cells. In some embodiments, the anti-cancer agent is a cytotoxic agent.

Non-limiting examples of commercially available anti-cancer agents for treating cancers of the oral cavity and oropharynx include: Cisplatin, Carboplatin, 5-fluorouracil (5-FU), Paclitaxel, Docetaxel, Methotrexate, Ifosfamide, and Bleomycin.

In some embodiments, the active agent is selected from, without being limited thereto, chloroform, Dextrose, cyanoacrylate glue, L-glutamine, penicillin, streptomycin, trypsin, EDTA, and doxorubicin.

The terms "cancer" and "tumor" are used interchangeably herein to describe a class of diseases in which a group of cells display uncontrolled growth (division beyond the normal limits). The term "cancer" encompasses malignant and benign tumors as well as disease conditions evolving from primary or secondary tumors. The term "malignant tumor" describes a tumor which is not self-limited in its growth, is capable of invading into adjacent tissues, and may be capable of spreading to distant tissues (metastasizing). The term "benign tumor" describes a tumor which is not-malignant (i.e. does not grow in an unlimited, aggressive manner, does not invade surrounding tissues, and does not metastasize). The term "primary tumor" describes a tumor that is at the original site where it first arose. The term "secondary tumor" describes a tumor that has spread from its original (primary) site of growth to another site, close to or distant from the primary site.

As used herein, the term "saliva" refers to the oral fluid typically made up of a combination of secretions from a number of sources (e.g., parotid, submandibular, sublingual, accessory glands, gingival mucosa and buccal mucosa).

The combined friction reduction and therapeutic effect is particularly advantageous when the polymeric/liposomes composition is used in an application that also requires a localized enhanced effect of the therapeutically active agent.

The release rate of the active agent from the hydrogel is governed inter alia by the chemical composition of the polymer chains, the "degree of crosslinking" (number of interconnected links between the chains), the aqueous media content and composition, and temperature.

Carriers

In some embodiments, the invention provides carriers in the form of nanoparticles and liposomal membranes. In some embodiments, carrier is in a form of a vesicle such that carried materials (therapeutic agent or diagnostic agent) are inside an internal core. In some embodiments, the at least one carrier is a lipid-based particle. In another embodiment, the lipid-based particle is a liposome. In another embodiment, the at least one carrier is a micelle.

In some embodiments, the at least one carrier is in a form of a vesicle such that carried materials form a complex/particulate with the carried materials with or without the another agent such as a polymer, protein, or salt. In some embodiments, the at least one carrier forms a dendrimer like structure in which the components are conjugated to the polymeric backbone or complexed via van der Waals or hydrophobic interactions.

As described herein, liposomes are known in the art as artificial vesicles composed of a substantially spherical lipid bilayer which typically, but not exclusively, comprises phospholipids, sterol, e.g., cholesterol, and other lipids.

Hereinthroughout, "liposomes" refer to one or more liposomes.

In some embodiments, the liposomes are characterized by a proper packing parameter. As used herein and in the art, packing parameter is a relative measure of a given lipid composition, and depend on factors such as size relationships between lipid head groups and lipid hydrocarbon chains, charge, and the presence of stabilizers such as cholesterol. It should also be noted that the packing parameter may be not constant. In some embodiments, the parameter is dependent on various conditions which effect each the volume of the hydrophobic chain, the cross-sectional area of the hydrophilic head group, and the length of the hydrophobic chain. Factors can affect these include, but are not limited to, the properties of the solvent, the solvent temperature, and the ionic strength of the solvent.

In some embodiments, the proper packing parameter is in the range of 0.3 to 1, e.g., 0.3, 0.5, 0.7, 0.9, or 1, including any value and range therebetween.

In some embodiments, the liposome is characterized by a desired surface charge, anionic surface charge, or cationic surface charge, as described hereinbelow.

Without being bound by any particular theory, it is noted herein that the use of liposomes dispersed in a hydrogel rather than the use of liposome in liquid suspension, is advantageous, as it provides a reservoir of liposomes within the hydrogel that provide a desired release profile (e.g., controlled release) of the liposomes and substances encapsulated therein from the disclosed composition to a targeted area.

Without being bound by any particular theory, it is suggested that the micro-structural effect of incorporation of liposomes in a hydrogel can result in the distribution of the liposomes throughout the bulk of the hydrogel.

In some embodiments, the liposomes are distributed in the hydrogel substantially uniformly in a single liposome form or in the form of clusters of liposomes.

In some embodiments, the liposomes are held physically, or electrostatically, through chemical bonds in the hydrogel matrix.

In some embodiments, the disclosed hydrogel holds liposomes of different types. In some embodiments, "by different types" it is meant to refer to liposomes that encapsulate different active agents (e.g., drugs). In some embodiments, "by different types" it is meant to refer to liposomes that are of different structure and configurations.

In some embodiments, the liposome conjugates a moiety on its surface that connects to the hydrogel. In some embodiments, by "conjugate" it is meant some of the backbone units of the liposome have the moiety attached thereto.

In some embodiments, the liposome comprises a targeting moiety on at least one surface thereof. A targeting moiety is a moiety know in the art to associate with a cell. This may be achieved, for example, by inserting modifying the targeting moiety with a lipophilic moiety to allow insertion into or association with a desired cell membrane or an external tissue. In some embodiments, by "desired cell membrane" it is meant to refer to a membrane of a pathological cell.

Non-limiting examples of external tissue include skin, gastrointestinal tract, oral cavity, anus, etc.

In some embodiments, a targeting moiety may contain a tag which facilitates its isolation, immobilization, identification, or detection In some embodiments, the concentration of the liposomes may range from about 20 mM to 200 mM, or from about 30 mM to 150 mM, or from about 40 mM to 120 mM, from about 50 mM to 100 mM.

It is noted that in general, liposomes having a small diameter have a high radius of curvature that confers an asymmetric distribution of the bilayer constituents. Furthermore, small liposomes are limited in terms of the encapsulation of aqueous space per mole of lipid. Hence, liposomes having a small diameter may exhibit a less stable spherical structure. Relatively unstable liposomes may be disadvantageous, especially while applying high loads and or may be advantageous, in embodiments where liposome breakdown is desirable.

In some embodiments, the liposomes are nanosized. In some embodiments, the size of the liposomes described herein represents an average or median size of a plurality of liposomes.

In some embodiments, the average or median size of at least e.g., 50%, 60%, 70%, 80%, 90%, or 95% of the liposomes, including any value therebetween, ranges from: about 50 nanometers to 500 nanometers, or, in other embodiments, from 100 nm to 300 nm.

In some embodiments, a plurality of the liposomes has a uniform size. By "uniform size" it is meant to refer to diameter size distribution of the liposomes that varies within a range of less than e.g., 60%, 50%, 40%, 30%, 20%, 10%, including any value therebetween.

The liposome size distribution may be measured by any method known in the art (e.g., Dynamic Light Scattering; DLS).

In some embodiments, the size of the liposomes dispersed throughout the bulk of the hydrogel, is about 50 nm, about 50 nm, about 60 nm, about 70 nm, about 80 nm, about 90 nm, about 100 nm, about 150 nm, about 200 nm, about 250 nm, about 300 nm, about 400 nm, or about 500 nm diameter, including any value and range therebetween.

In some embodiments, the size of the liposomes stated herein and throughout refers to the size which has been measured shortly before gelation and incorporation of the liposomes in the past's or hydrogel's network. In some embodiments, the liposomes do not change their size once entrapped in the hydrogel's network.

In some embodiments, the liposomes that are incorporated into hydrogels are comprised of at least one phospholipid or cholesterol.

In some embodiments, the liposomes can be prepared such that the lipid bilayer comprises stabilizing components, surface-altering components and structure-altering components.

In some embodiments, the liposomes encapsulate or incorporate into their lipid bilayer, or are used in combination with, an additional active agent as described hereinbelow. The additional agent can be used in the preparation of the liposomes. In some embodiments, such additional agents, can be a polymer, cholesterol, a liposome-stabilizing agent and/or an active agent, while an active agent can be a labeling agent, a bioactive agent or a therapeutically active agent. In some embodiments, the additional agent can serve one, two or all three of the above functions.

In some embodiments, liposome(s) encapsulates various factors, solutes, compounds, macromolecules, genetic-coding materials, drugs and many other chemical entities, as further described hereinbelow. Such chemical entities, whether incorporated into the lipid bilayer or encapsulated within the liposome, may affect the structure of the liposome in terms of its size and stability, may affect the reactivity of the liposome towards other chemical entries.

The process of incorporation of a desired entity into a liposome is often referred to as "loading" (Lasic, et al., FEBS Lett., 312: 255-258, 1992). The liposome-incorporated therapeutic/diagnostic agents, may be completely or partially located in the interior space of the liposome, within the bilayer membrane of the liposome. Incorporation of an agent into liposomes is also referred to herein as "encapsulation" wherein the agent is entirely contained within the interior space of the liposome. Typically, for encapsulation of an agent within a carrier (e.g. liposome) a chemical linkage, such as a covalent linkage between the agent and the carrier, is not required. The purpose of incorporating an agent into a transfer vehicle, such as a liposome, is often to protect the agent from an environment which may contain enzymes or chemicals that degrade the agent (e.g., nucleic acids) and/or systems or receptors that cause the rapid excretion of the agent. Accordingly, in a preferred embodiment of the present invention, the selected transfer vehicle is capable of enhancing the stability of the therapeutic agent and the nucleic acid molecule and optionally the tag contained therein. The liposome can allow the encapsulated agents to reach the target cell and/or may preferentially allow the encapsulated agents to reach the target cell, or alternatively limit the delivery of the agents to other undesired target sites or cells.

In some embodiments, liposomal transfer vehicles are prepared to encapsulate one or more desired agent such that the compositions demonstrate a high transfection efficiency and enhanced stability. While liposomes can facilitate introduction of nucleic acids into target cells, the addition of polycations (e.g., poly L-lysine and protamine), as a copolymer can facilitate, and in some instances markedly enhance the transfection efficiency of several types of cationic liposomes by 2-28 fold in a number of cell lines both in vitro and in vivo.

In another embodiment, the at least one carrier is a nanoliposome or lipid nanoparticle. Nanoliposomes are able to enhance the performance of bioactive agents by improving their solubility and bioavailability, in vitro and in vivo stability, as well as preventing their unwanted interactions with other molecules. Another advantage of nanoliposomes is cell-specific targeting, which is a prerequisite to attain drug concentrations required for optimum therapeutic efficacy in the target cell while minimizing adverse effects on healthy cells and tissues.

As used herein, the phrase "lipid nanoparticle" refers to a transfer vehicle comprising one or more lipids (e.g., cationic lipids, non-cationic lipids, and PEG-modified lipids (e.g., by a covalent bond)). Preferably, the lipid nanoparticles are formulated to deliver one or more agents to one or more target cells. Examples of suitable lipids include, for example, the phosphatidyl compounds (e.g., phosphatidylglycerol, phosphatidylcholine, phosphatidylserine, phosphatidylethanolamine, sphingolipids, cerebrosides, and gangliosides). Also contemplated is the use of polymers as transfer vehicles, whether alone or in combination with other transfer vehicles. Suitable polymers may include, for example, polyacrylates, polyalkycyanoacrylates, polylactide, polylactide-polyglycolide copolymers, polycaprolactones, dextran, albumin, gelatin, alginate, collagen, chitosan, cyclodextrins, dendrimers and polyethylenimine. In one embodiment, the transfer vehicle is selected based upon its ability to facilitate the transfection of a nucleic acid to a target cell.

The invention contemplates the use of lipid nanoparticles as transfer vehicles comprising a cationic lipid to encapsulate and/or enhance the delivery of nucleic acid into the target cell. As used herein, the phrase "cationic lipid" refers to any of a number of lipid species that carry a net positive charge at a selected pH, such as physiological pH. The contemplated lipid nanoparticles may be prepared by including multi-component lipid mixtures of varying ratios employing one or more cationic lipids, non-cationic lipids and PEG-modified lipids. Several cationic lipids have been described in the literature, many of which are commercially available.

Suitable cationic lipids for use in the compositions and methods of the invention include those described in international patent publication WO 2010/053572, incorporated herein by reference. In certain embodiments, the compositions and methods of the invention employ a lipid nanoparticle comprising an ionizable cationic lipid. In some embodiments, the cationic lipid N-[1-(2,3-dioleyloxy)propyl]-N,N,N-trimethylammonium chloride or "DOTMA" is used. (U.S. Pat. No. 4,897,355). DOTMA can be formulated alone or can be combined with the neutral lipid, dioleoylphosphatidyl-ethanolamine or "DOPE" or other cationic or non-cationic lipids into a liposomal transfer vehicle or a lipid nanoparticle, and such liposomes can be used to enhance the delivery of nucleic acids into target cells. Other suitable cationic lipids include, for example, 5-carboxyspermylglycinedioctadecylamide or "DOGS," 2,3-dioleyloxy-N-[2(spermine-carboxamido)ethyl]-N,N-dimethyl-1-pr-opanaminium or "DOSPA" (U.S. Pat. Nos. 5,171,678; 5,334,761), 1,2-Dioleoyl-3-Dimethylammonium-Propane or "DODAP", 1,2-Dioleoyl-3-Trimethylammonium-Propane or "DOTAP". Contemplated cationic lipids also include 1,2-distearyloxy-N,N-dimethyl-3-aminopropane or "DSDMA", 1,2-dioleyloxy-N,N-dimethyl-3-aminopropane or "DODMA", 1,2-dilinoleyloxy-N,N-dimethyl-3-aminopropane or "DLinDMA", 1,2-dilinolenyloxy-N,N-dimethyl-3-aminopropane or "DLenDMA", N-dioleyl-N,N-dimethyl-ammonium chloride or "DODAC", N,N-distearyl-N,N-dimethylammonium bromide or "DDAB", N-(1,2-dimyristyloxyprop-3-yl)-N,N-dimethyl-N-hydroxyethyl ammonium bromide or "DMRIE", 3-dimethylamino-2-(cholest-5-en-3-beta-oxybutan-4-oxy)-1-(cis,cis-9,12-oc-tadecadienoxy)propane or "CLinDMA", 2-[5'-(cholest-5-en-3-beta-oxy)-3'-oxapentoxy)-3-dimethy 1-1-(cis,cis-9',1-2'-octadecadienoxy)propane or "CpLinDMA", N,N-dimethyl-3,4-dioleyloxybenzylamine or "DMOBA", 1,2-N,N'-dioleylcarbamyl-3-dimethylaminopropane or "DOcarbDAP", 2,3-Dilinoleoyloxy-N,N-dimethylpropylamine or "DLinDAP", 1,2-N,N'-Dilinoleylcarbamyl-3-dimethylaminopropane or "DLincarbDAP", 1,2-Dilinoleoylcarbamyl-3-dimethylaminopropane or "DLinCDAP", 2,2-dilinoleyl-4-dimethylaminomethyl-[1,3]-dioxolane or "DLin-K-DMA", 2,2-dilinoleyl-4-dimethylaminoethyl-[1,3]-dioxolane or "DLin-K-XTC2-DMA", and 2-(2,2-di((9Z,12Z)-octadeca-9,12-dien-1-yl)-1,3-dioxolan-4-yl)-N,N-dimethylethanamine (DLin-KC2-DMA)) (See, WO 2010/042877; Semple et al., Nature Biotech. 28:172-176 (2010)), or mixtures thereof. (Heyes, J., et al., J Controlled Release 107: 276-287 (2005); Morrissey, D V., et al., Nat. Biotechnol. 23(8): 1003-1007 (2005); PCT Publication WO2005/121348A1).

The use of cholesterol-based cationic lipids is also contemplated by the present invention. Such cholesterol-based cationic lipids can be used, either alone or in combination with other cationic or non-cationic lipids. Suitable cholesterol-based cationic lipids include, for example, DC-Chol (N,N-dimethyl-N-ethylcarboxamidocholesterol), 1,4-bis(3-N-oleylamino-propyl)piperazine (Gao, et al. Biochem. Biophys. Res. Comm. 179, 280 (1991); Wolf et al. BioTechniques 23, 139 (1997); U.S. Pat. No. 5,744,335), or ICE.

In addition, several reagents are commercially available to enhance transfection efficacy. Suitable examples include LIPOFECTIN (DOTMA:DOPE) (Invitrogen, Carlsbad, Calif.), LIPOFECTAMINE (DOSPA:DOPE) (Invitrogen), LIPOFECTAMINE2000. (Invitrogen), FUGENE, TRANSFECTAM (DOGS), and EFFECTENE.

Also contemplated are cationic lipids such as the dialkylamino-based, imidazole-based, and guanidinium-based lipids. For example, certain embodiments are directed to a composition comprising one or more imidazole-based cationic lipids.

In some embodiments, one or more nano-carriers further comprises a coupling agent attached thereto. Such molecule of coupling agent can extend from the liposome surface or be an integral part of the liposome lipid. In some embodiments, the coupling agent is derived from polyethylene glycol (PEG). The use of polyethylene glycol (PEG)-modified phospholipids and derivatized lipids such as derivatized ceramides (PEG-CER), including N-Octanoyl-Sphingosine-1-[Succinyl(Methoxy Polyethylene Glycol)-2000] (C8 PEG-2000 ceramide) is also contemplated by the present invention, either alone or preferably in combination with other lipids together which comprise the transfer vehicle (e.g., a lipid nanoparticle).

The addition of such coupling agents may allow homogenization of the nanocarriers within the matrix, prevent complex aggregation and may also provide a means for increasing circulation lifetime and increasing the delivery of the agent to the target cell, or they may be selected to rapidly exchange out of the matrix in vivo conditions.

In some embodiments, by "homogenization" it is meant that the concentration of the nano-carriers in e.g., at least 10%, at least 20%, at least 30%, at least 40%, at least 50%, or at least 60% of the volume of the disclosed matrix varies within less than ±20%.

Particularly useful exchangeable lipids are PEG-ceramides having shorter acyl chains (e.g., C14 or C18). The PEG-modified phospholipid and derivitized lipids of the present invention may comprise a molar ratio from about 0% to about 20%, from about 0.5% to about 20%, from about 1% to about 15%, from about 4% to about 10%, or about 2% of the total lipid present in the liposomal transfer vehicle.

In some embodiments, at least 0.5%, at least 1%, at least 10%, or at least 20% of the nano-carriers are linked to the muco-adhesive polymer via the coupling agent.

In some embodiments, by the terms "linked", "coupled", or any other grammatical derivative thereof, it is meant to refer to a covalent bond between the nanocarrier (liposome) and the matrix, e.g., though amine or carboxyl groups on the liposome surface which covalently bind the gel.

In some embodiments, these terms refer to a non-covalent ("physical") bond between the liposome and the matrix (such as, without being limited thereto, hydrogen bonds), for example via hydrogen bonds to PEG.

The present invention also contemplates the use of non-cationic lipids. As used herein, the phrase "non-cationic lipid" refers to any neutral, zwitterionic or anionic lipid. As used herein, the phrase "anionic lipid" refers to any of a number of lipid species that carry a net negative charge at a selected pH, such as physiological pH. Non-cationic lipids include, but are not limited to, distearoylphosphatidylcholine (DSPC), dioleoylphosphatidylcholine (DOPC), dipalmitoylphosphatidylcholine (DPPC), dioleoylphosphatidylglycerol (DOPG), dipalmitoylphosphatidylglycerol (DPPG), dioleoylphosphatidylethanolamine (DOPE), palmitoyloleoylphosphatidylcholine (POPC), palmitoyloleoyl-phosphatidylethanolamine (POPE), dioleoyl-phosphatidylethanolamine 4-(N-maleimidomethyl)-cyclohexane-1-carboxylate (DOPE-mal), dipalmitoyl phosphatidyl ethanolamine (DPPE), dimyristoylphosphoethanolamine (DMPE), distearoyl-phosphatidyl-ethanolamine (DSPE), 16-O-monomethyl PE, 16-O-dimethyl PE, 18-1-trans PE, 1-stearoyl-2-oleoyl-phosphatidyethanolamine (SOPE)-2-dimyristoyl-sn-glycero-3-phosphocholine, hydrogenated soybean phosphatidylcholine, cholesterol, or a mixture thereof. Such non-cationic lipids may be used alone, but are preferably used in combination with other excipients, for example, cationic lipids. When used in combination with a cationic lipid, the non-cationic lipid may comprise a molar ratio of 5% to about 90%, or preferably about 10% to about 70% of the total lipid present in the transfer vehicle.

In some embodiments, the transfer vehicle (e.g., a lipid nanoparticle) is prepared by combining multiple lipid and/or polymer components. The selection of cationic lipids, non-cationic lipids and/or PEG-modified lipids which comprise the lipid nanoparticle, as well as the relative molar ratio of such lipids to each other, is based upon the characteristics of the selected lipid(s), the nature of the intended target cells and the characteristics of the agents to be delivered. Additional considerations include, for example, the saturation of the alkyl chain, as well as the size, charge, pH, pKa, fusogenicity and toxicity of the selected lipid(s).

The liposomal transfer vehicles for use in the compositions of the invention can be prepared by various techniques which are presently known in the art. Multi-lamellar vesicles (MLV) may be prepared conventional techniques, for example, by depositing a selected lipid on the inside wall of a suitable container or vessel by dissolving the lipid in an appropriate solvent, and then evaporating the solvent to leave a thin film on the inside of the vessel or by spray drying. An aqueous phase may then be added to the vessel with a vortexing motion which results in the formation of MLVs. Uni-lamellar vesicles (ULV) can then be formed by homogenization, sonication or extrusion of the multi-lamellar vesicles. In addition, unilamellar vesicles can be formed by detergent removal techniques.

In certain embodiments, the liposome of the invention comprises DMPC:cholesterol in a defined ratio. In certain embodiments, the liposome of the invention comprises DMPC:cholesterol in the ratio of e.g., from 80:20 to 70:30 or from 60:40 to 70:30, respectively. In certain embodiments, the liposome of the invention comprises DMPC:cholesterol in the ratio of 80:20, 75:25, 70:30, 65:35, or 60:40, respectively, including any value and range therebetween.

In certain embodiments, the liposome of the invention comprises polyethylene glycol (PEG). In certain embodiments, the liposome of the invention comprises DMPC:cholesterol:PEG in a defined ratio. In certain embodiments, the liposome of the invention comprises DMPC:cholesterol:PEG in the ratio of from 55:40:5 to 65:30:5, respectively. In certain embodiments, the liposome of the invention comprises DMPC:cholesterol:PEG in the ratio of 55:40:5, 60:35:5, or 55:30:5, respectively, including any value and range therebetween.

In certain embodiments, the liposome of the invention comprises hydrogenated soy phosphatidylcholine (HSPC):cholesterol:PEG in a defined ratio. In certain embodiments, the liposome of the invention comprises HSPC:cholesterol:PEG in the ratio of 65:30:5, respectively. In certain embodiments, the liposome of the invention comprises HSPC:cholesterol:PEG in the ratio of 55:40:5, 60:35:5, or 55:30:5, respectively, including any value and range therebetween.

In certain embodiments, the compositions of the invention may be loaded with diagnostic radionuclide, fluorescent materials or other materials that are detectable in both in vitro and in vivo applications.

In some embodiments, the nanoparticle carriers of the invention are fabricated of lipids using an in-line microfluidic setup adapted to accommodate high-throughput synthesis and labeling of the particles. Such fabrication methods are known in the art, e.g., Jahn et al., 2007, Langmuir 23, 6289-6293. Typically, particles of appropriate sizes to accommodate the therapeutic payload are fabricated.

Chemical agents may be loaded into stable HSPC particles, for examples as shown by Schroeder et al., 2007, Langmuir 23, 4019-4025. Biological therapeutics (protein/RNA) may be synthesized inside 'protein producing nanoparticles'. In some embodiments, a synthetic nanoparticle is controllably triggered to synthesize proteins and RNA at a target site, as shown in Schroeder, A. et al. *Nano Lett* 12, 2685-2689, (2012). These nanoparticles consist of lipid vesicles filled with the molecular machinery responsible for transcription and translation, including amino acids, ribosomes, and DNA caged with a photo-labile protecting group. The particles serve as nano-factories capable of producing RNA/proteins. In vitro and in vivo, protein/RNA synthesis may be spatially and temporally controllable, and can be initiated by illuminating micron-scale tissue regions on the timescale of milliseconds. As such, this platform may be used to screen RNA (Png et al. 2012 Nature 481, 190-194) and proteins for their activity, e.g., anti-cancer activity.

Sustained-Release Formulations

In another embodiment, the sustained-release preparation of the present invention is characteristic in that it is easily adhered to mucous membrane in oral cavity and the adhesion is maintained for a long period of time, for example, for 0.1 to 24 hours. Besides, it can be kept within the oral cavity without being peeled off even by usual mouth action such as drinking, smoking, eating and speaking.

In some embodiments, the preparation (e.g., in the form of hydrogel or paste) may be sprayed on the desired tissue surface.

In some embodiments, the release rate of the liposomes is dependent on the erosion of e.g., the hydrogel.

In some embodiments, the liposomes release the encapsulated active agent when the liposome is retained inside the hydrogel matrix. In some embodiments, the liposome releases the encapsulated active agent when the liposome is released from the hydrogel matrix.

In another embodiment, the sustained-release preparation of the present invention is characteristic in that the formed preparation is swollen by saliva to become soft, and hence, it does not give any abnormal feeling to the persons to whom the preparation is applied.

In another embodiment, the sustained-release preparation of the present invention is characteristic in that the release of the active ingredient can be sustained in accordance with the viscosity of the base materials.

In another embodiment, the sustained-release preparation of the present invention is characteristic in that the dose of each preparation is previously fixed when it is prepared, and hence, there is no difference of dose in each application (not like in ointment).

In another embodiment, the sustained-release preparation of the present invention is characteristic in that the adhesion and release sustaining property of the preparation can be controlled by appropriately controlling the components, as described hereinbelow.

The compositions and formulations of the invention may further comprise additives such as lubricants, binding agents, excipients, flavors and seasonings. The lubricants used in this invention include, for example, talc, stearic acid and a salt thereof, waxes, etc.; the binding agents include, for example, starches, dextrin, tragacanth, gelatin, hydroxypropyl cellulose, etc.; the excipients include, for example, starches, crystalline cellulose, dextrin, lactose, mannitol, sorbitol, anhydrous calcium phosphate, etc.; and the flavors and seasonings include, for example, citric acid, fumaric acid, tartaric acid, menthol, flavors of citrus fruits, etc. These additives other than the polymers are incorporated in an amount of not more than 40% by weight, preferably not more than 20% by weight, based on the whole weight of the preparation in order to avoid deterioration of the release sustaining properties of the present preparation.

According to another aspect of some embodiments of the present invention, there is provided a kit for storing, preparing and/or applying a bioadhesive matrix presented herein, which includes at least two compartments, such as a first compartment and a second compartment, wherein the first compartment contains sub-formulation A, as presented hereinabove, and the second compartment contains sub-formulation B.

In some embodiments, by "preparing" it is meant to refer to making a single concoction, composition or a matrix as disclosed herein which can be formed ex vivo, in vitro or in situ, namely the formulation can be in the form of two or more sub-formulations kept separately, or as a set of dry powders and a pre-measured amount of solvent (water) kept separately, as discussed hereinbelow, which are combined to form the single concoction by one of the following manners.

In vitro means that the formulation as a single concoction is formed by mixing (e.g., in a vial) all the components of the formulation, as these are defined, described and exemplified herein, prior to applying the formulation onto the object(s) to be bonded.

In situ means that the formulation as a single concoction is formed by applying one sub-formulation on one object, and another sub-formulation on another object, and adjoining the objects together to form the single concoction at the site of adhesion; or by applying one sub-formulation on an object and thereafter applying another sub-formulation on the same object.

For example, cross-linked polymers may be formed in situ thereby forming a network by the absorption of cross-linking agent.

When applied to animated objects, in vitro corresponds to ex vivo, and in situ corresponds to in vivo.

In some embodiments, the kit includes at least two compartments, each containing the constituents corresponding to the particular sub-formulation, which have been pre-dissolved in a solvent to a specific concentration such that mixing the two sub-formulations results in a bioadhesive matrix as described herein.

Alternatively, the kit includes one or more compartments, each containing a pre-measured amount of a dry powder of one or more constituent of the bioadhesive formulation, and a separate compartment containing a pre-measured amount of the solvent, such that mixing the powder(s) and the solvent results in a bioadhesive formulation as described herein.

The kit may further include mixing and stirring tools, bowls, applicators, freshness indicators, tamper-proof measures and printed matter for instructions for the user.

The kit may include a device, an applicator or a dispenser for expelling measured amounts of each sub-formulation controllably and optionally synchronously, each of which is dispensed from the individual compartment serving as a cartridge of the individual sub-formulation.

In some embodiments, the kit is for forming a drug-eluting bioadhesive matrix.

In some embodiments, the kit comprises:
(a) a formulation comprising the disclosed muco-adhesive polymer;
(b) a formulation comprising one or more nano-carriers, wherein the nano-carrier comprises a therapeutic or diagnostic as described herein.

In some embodiments, the kit further comprises a composition comprising one or more crosslinking agents as disclosed herein.

In some embodiments, the formulation is in the form of a paste.

In some embodiments the kit further comprises a composition comprising one or more blocking agents as described herein.

Methods of Use

The present inventors have shown the feasibility of localized therapy by the administration of the disclosed composition.

In some embodiments, there is provided a method for preparing a drug-eluting bioadhesive matrix on a mucus membrane, the method comprising performing the following steps in a predetermined order:
(a) introducing a paste comprising one or more nano-carriers on a mucus membrane, wherein the nano-carrier comprises at least one therapeutic or diagnostic agent;
(b) incorporating a formulation comprising a muco-adhesive polymer into/onto the paste, thereby forming a drug-eluting bioadhesive matrix.

In some embodiments, the method further comprises a step of introducing a composition comprising one or more crosslinking agents into the paste.

In some embodiments, the method further comprises a step of introducing a paste comprising a blocking agent onto the network.

Embodiments of nano-carriers, muco-adhesive polymer, bioadhesive matrix, crosslinking agents, are described hereinthroughout.

According to an aspect of embodiments of the invention there is provided a medicament comprising one or more compositions disclosed herein and a pharmaceutically acceptable carrier.

According to some embodiments of the invention, the medicament is being packaged in a packaging material and identified in print, in or on the packaging material, for use in the treatment of a medical condition associated with any disease, medical condition, or disorder as described hereinthroughout.

In some embodiments, localized therapy in the oral cavity (i.e. inner oral tissue) is achieved within e.g., several hours of administration, e.g., topical administration. Without being bound by any particular mechanism, it is assumed that the mechanism of in release of the active agent from the disclosed composition is likely to involve dissolution/erosion of the polymer.

According to some embodiments, there is provided a method of diagnosing a disease in a subject, the method comprising determining a level and/or activity of at least one saliva secreted marker in a saliva sample of the subject, wherein an alteration in the marker with respect to an unaffected saliva sample is indicative of the disease.

As used herein, the term "diagnosing" refers to determining the presence of a disease, classifying a disease, determining a severity of a disease (grade or stage), monitoring the disease progression, forecasting an outcome of the disease and/or prospects of recovery. In some embodiments, the disease is cancer.

In some embodiments, the disclosed paste or hydrogel further comprises a labeling agent. As used herein, the phrase "labeling agent" or "labeling compound" describes a detectable moiety or a probe. The labeling agent may be attached to a portion of the backbone units forming the polymeric backbone of the paste/hydrogel, directly or via a spacer. Alternatively, the labeling agent may be encapsulated within the void space within the paste/hydrogel.

As used herein, the term "subject" refers to any animal (e.g., a mammal), including, but not limited to, humans, non-human primates, rodents, and the like, to which the compositions and methods of the present invention are administered. In some embodiments, the terms "subject" and "patient" are used interchangeably herein in reference to a human subject. In other embodiments, the terms "subject" and "patient" are used interchangeably herein in reference to a non-human subject.

Examples of cancer therapeutic agents include, e.g., but are not limited to Abiraterone, Acitretin, Aldesleukin, Alemtuzumab, Amifostine, Amsacrine, Anagrelide, Anastrozole, Arsenic, Asparaginase, Asparaginase Erwinia, Axitinib, azaClTltidine, BCG, Bendamustine, Bevacizumab, Bexarotene, Bicalutamide, Bleomycin, Bortezomib, Brentuximab, Bromocriptine, Buserelin, Busulfan, Cabazitaxel-Cabergoline, Capecitabine, CARBOplatin, Carmustine, Cetuximab, Chlorambucil, ClSplatin, Cladribine, Clodronate, Crizotinib, Cyclophosphamide, CycloSPORINE, Cytarabine, Dacarbazine, Dactinomycin, Dasatinib, DAUNOrubicin, Degarelix, Denosumab, Dexamethasone, Dexrazoxane, DOCEtaxel, DOXOrubicin, DOXOrubicin pegylated liposomal, Enzalutamide, Epirubicin, Eribulin, Erlotinib, Estramustine, Etoposide, Everolimus, Exemestane, Filgrastim, Fludarabine, Fluorouracil, Flutamide, Fulvestrant, Gefitinib, Gemcitabine, Goserelin, Hydroxyurea, IDArubicin, Ifosfamide, Imatinib, Iniparib, Interferon alfa-2b, Ipilimumab, Irinotecan, Ixabepilone, Lambrolizumab, Lanreotide, Lapatinib, Lenalidomide, Letrozole, Leucovorin, Leuprolide, Lomustine, Mechlorethamine, medroxyPROGESTERone, Megestrol, Melphalan, Mercaptopurine, Mesna, Methotrexate, mitoMYCIN, Mitotane, mitoXANTRONE, Nilotinib, Nilutamide, Octreotide, Ofatumumab, Oxaliplatin, PACLitaxel, ACLitaxel nanoparticle, albumin-bound (nab), Pamidronate, Panitumumab, Pazopanib Pemetrexed, Pertuzumab, Porfimer, Procarbazine, Quinagolide, Raltitrexed, Reovirus Serotype 3—Dearing Strain, riTUXimab, Romidepsin, Ruxolitinib, SORAfenib, Streptozocin, SUNltinib, Tamoxifen, Temozolomide, Temsirolimus, Teniposide, Testosterone, Thalidomide, Thioguanine, Thiotepa, Thyrotropin alfa, Tocilizumab, Topotecan, Trastuzumab (HERCEPTIN®), Trastuzumab, Emtansine (KADCYLA®), Treosulfan, Tretinoin, Vemurafenib, vinBLAstine, vinCRIstine and Vinorelbine.

Examples of chemotherapeutic agents used as a therapeutic agent include, e.g., but are not limited to, e.g., alkylating agents (e.g., cyclophosphamide, ifosfamide, melphalan, chlorambucil, aziridines, epoxides, alkyl sulfonates), cisplatin and its analogues (e.g., carboplatin, oxaliplatin), antimetabolitites (e.g., methotrexate, 5-fluorouracil, capecitabine, cytarabine, gemcitabine, fludarabine), toposiomerase interactive agents (e.g., camptothecin, irinotecan, topotecan, etoposide, teniposide, doxorubicin, daunorubicin), antimicrotubule agents (e.g., vinca alkaloids, such as vincristine, vinblastine, and vinorelbine; taxanes, such as paclitaxel and docetaxel), interferons, interleukin-2, histone deacetylase inhibitors, monoclonal antibodies, estrogen modulators (e.g., tamoxifen, toremifene, raloxifene), megestrol, aromatase inhibitors (e.g., letrozole, anastrozole, exemestane, octreotide), octreotide, anti-androgens (e.g., flutamide, casodex), kinase and tyrosine inhibitors (e.g., imatinib (STI571 or Gleevac); gefitinib (Iressa); and erlotinib (Tarceva), etc. See, e.g. Cancer: Principles and Practice of Oncology, 7th Edition, Devita et al, Lippincott Williams & Wilkins, 2005, Chapters 15, 16, 17, and 63).

In some embodiments, the method of the invention is useful for determining or predicting the response of a subject afflicted with an inflammatory disease or disorder to a therapeutic agent.

Additional objects, advantages, and novel features of the present invention will become apparent to one ordinarily skilled in the art upon examination of the following examples, which are not intended to be limiting. Additionally, each of the various embodiments and aspects of the present invention as delineated hereinabove and as claimed in the claims section below finds experimental support in the following examples.

General

As used herein the term "about" refers to ±10%.

The terms "comprises", "comprising", "includes", "including", "having" and their conjugates mean "including but not limited to". The term "consisting of" means "including and limited to". The term "consisting essentially of" means that the composition, method or structure may include additional ingredients, steps and/or parts, but only if the additional ingredients, steps and/or parts do not materially alter the basic and novel characteristics of the claimed composition, method or structure.

The word "exemplary" is used herein to mean "serving as an example, instance or illustration". Any embodiment described as "exemplary" is not necessarily to be construed as preferred or advantageous over other embodiments and/or to exclude the incorporation of features from other embodiments.

The word "optionally" is used herein to mean "is provided in some embodiments and not provided in other embodiments". Any particular embodiment of the invention may include a plurality of "optional" features unless such features conflict.

As used herein, the singular form "a", "an" and "the" include plural references unless the context clearly dictates otherwise. For example, the term "a compound" or "at least one compound" may include a plurality of compounds, including mixtures thereof.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

As used herein the term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts.

As used herein, the term "treating" includes abrogating, substantially inhibiting, slowing or reversing the progression of a condition, substantially ameliorating clinical or aesthetical symptoms of a condition or substantially preventing the appearance of clinical or aesthetical symptoms of a condition.

In those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Various embodiments and aspects of the present invention as delineated hereinabove and as claimed in the claims section below find experimental support in the following examples.

EXAMPLES

Reference is now made to the following examples which, together with the above descriptions, illustrate the invention in a non-limiting fashion.

Generally, the nomenclature used herein and the laboratory procedures utilized in the present invention include molecular, biochemical, microbiological and recombinant DNA techniques. Such techniques are thoroughly explained in the literature. See, for example, "Molecular Cloning: A laboratory Manual" Sambrook et al., (1989); "Current Protocols in Molecular Biology" Volumes I-III Ausubel, R. M., ed. (1994); Ausubel et al., "Current Protocols in Molecular Biology", John Wiley and Sons, Baltimore, Md. (1989); Perbal, "A Practical Guide to Molecular Cloning", John Wiley & Sons, New York (1988); Watson et al., "Recombinant DNA", Scientific American Books, New York; Birren et al. (eds) "Genome Analysis: A Laboratory Manual Series", Vols. 1-4, Cold Spring Harbor Laboratory Press, New York (1998); methodologies as set forth in U.S. Pat. Nos. 4,666,828; 4,683,202; 4,801,531; 5,192,659 and 5,272,057; "Cell Biology: A Laboratory Handbook", Volumes I-III Cellis, J. E., ed. (1994); "Culture of Animal Cells—A Manual of Basic Technique" by Freshney, Wiley-Liss, N. Y. (1994), Third Edition; "Current Protocols in Immunology" Volumes I-III Coligan J. E., ed. (1994); Stites et al. (eds), "Basic and Clinical Immunology" (8th Edition), Appleton & Lange, Norwalk, Conn. (1994); Mishell and Shiigi (eds), "Strategies for Protein Purification and Characterization—A Laboratory Course Manual" CSHL Press (1996); all of which are incorporated by reference. Other general references are provided throughout this document.

Materials and Methods

Materials

Sodium alginate HF120RBS, with G content of about 50%, was generously supplied by FMC-Biopolymers (Norway). 1-Ethyl-3-(3-dimethylaminopropyl)-carbodiimide hydrochloride (EDC) and genipin were purchased from Tzamal D-chem (Israel). Fluorescein isothiocyanate (FITC), sulforhodamine B, sodium hydroxide (NaOH), chitosan-low MW (Lot #MKBL7900V), 5,5'-dithiobis(2-nitrobenzoic acid) (DTNB), cholesterol, tetrazolium salt-3-(4,5-dimethylthiazol-2-yl)-2,5-diphenyl tetrazolium bromide (MTT), Dulbecco's Modified Eagle's Medium . . . (DMEM), Dulbecco's phosphate buffered saline (PBS), glucono delta-lactone (GDL), 2-(N-morpholino) ethanesulfonic acid (MES) and N-hydroxysuccineimide (NETS) were purchased from Sigma-Aldrich (Israel). Sodium chloride (NaCl) was purchased from S.D. Fine-Chem (India). 32% Hydrochloric acid (HCl) and citric acid were purchased from Frutarom (Israel). 1,2-dimyristoyl-sn-glycero-3-phosphocholine (DMPC) was purchased from Lipoid (Germany). 14:0-Rhodamine was purchased from Avanti polar lipidsInc. (USA). Calcium chloride ($CaCl_2$) was purchased from J.T.Baker (USA). Barium chloride ($BaCl_2$) was purchased from Alfa Aesar (England). Strontium chloride ($SrCl_2$) and acetic acid (AcOH) were purchased from EMSURE (USA). Ethanol (EtOH), methanol (MeOH), acetone and ethylene glycol were purchased from Bio-Lab ltd. (Israel). Ethylene glycol tetra acetic acid (EGTA) was purchased from STREM CHEMICALS (USA). Potassium chloride was purchased from NILE CHEMICALS (India). Potassium phosphate monobasic, sodium phosphate dibasic and potassium thiocyanate were obtained from MERCK (Germany). Potassium bicarbonate was purchased from LOBA CHEMIE (India). Porcine tongue was supplied by the Preclinical Research Authority Technion (Israel).

Cell Culture

Human tongue squamous cell carcinoma cell line, CAL-27 was obtained from the American Type Culture Collection (ATCC, Manassas, Va., USA). The cell line was cultured in DMEM supplemented with 10% (v/v) FBS, 2 mM L-glutamine, 100 Units/mL penicillin and 100 µg/mL streptomycin in a humidified atmosphere containing 5% (v/v) $CO_2$ and 95% (v/v) air at 37° C. Cells were detached by 0.25% (w/v) trypsin/0.02% (w/v) EDTA and split every 2-3 days to maintain cell growth.

Liposome Fabrication

Liposomes either empty or containing were prepared as follows: Initially, DMPC and cholesterol in molar ratio of 60:40 were dissolved in chloroform. Only for empty liposomes to be detected fluorescently, 1% v/v of a 2 mg/mL 14:0-Rhodamine stock solution was added to the chloroform solution. Then the solvent was evaporated using a rotary evaporator (BUCHI Labortechnik AG, Postfach, Switzerland) resulting in a thin lipid film. The film was hydrated with either 5% dextrose (w/v), 10% PBS (v/v) while rotating at 50° C. The dispersion became milky indicating the spontaneous formation of lipid vesicles. Nanoscale vesicles were created with stepwise extrusion five times through polycarbonate membranes (GE healthcare, Wauwatosa, Wis., USA) using 200 nm pore size membranes in a 10 mL extrusion system (Northern Lipids, Vancouver, Canada) at 50° C. Liposome size (200 nm) was validated by dynamic light scattering (DLS) was used.

Preparation of Hybrid Liposome/Chitosan Hydrogels

Chitosan hydrogels were prepared as previously described and modified for hybrid system preparation i.e., chitosan hydrogel with entrapped liposomes. Chitosan (40 mg) was dissolved in 2.2 mL 2% AcOH. The pH of the resulting solution was between 4, 5, or 6, depending on the desired hydrogel acidity (for pH of 4.5, chitosan was initially dissolved in 2% AcOH, pH=4 and for acidity of 5.6, the chitosan was dissolved in 2% AcOH, pH 5). Liposome solution, 1 mL 100 mM, was applied and stirred until adequate homogenous solutions were achieved. Genipin solution, 0.8 mL 0.01% w/v, was placed and the pH of the solutions was adjusted to either pH=4.5 or 5.6, using 0.1M HCl solution. Chitosan solution, 600 µL, was casted onto a silicon ring mold (14 mm diameter). The mixture was left to cure for 24 hr at room temperature in a closed petri dish, to avoid evaporation.

Preparation of Hybrid Liposome/Alginate Hydrogels

Alginate hydrogels were prepared as previously reported and modified for entrapping liposomes. Alginate (40 mg, $1.33 \times 10^{-4}$ mmol) was dissolved in 1.8 mL DDW and in 1 mL, 100 mM liposome solution. Ca-EGTA solution (800 µL, 100 mM) and GDL solution (400 µL, 20 mM) were then added, and stirred for 1 min. Alginate solution, 600 was placed onto a silicon ring mold and allowed to cure for 24 hr at room temperature in a close petri dish to avoid evaporation. Alginate hydrogel cross-linked with calcium-barium ($Ca^{+2}$—$Ba^{+2}$) mixture was prepared by mixing 780 µL of 100 mM Ca-EGTA and 20 µL 100 mM $BaCl_2$. Alginate hydrogel cross-linked with $Ca^{+2}$—$Sr^{+2}$ mixture was prepared similarly: solutions of 780 µL of 100 mM Ca-EGTA and 20 µL of 400 mM $SrCl_2$ were mixed together. These solutions were added to alginate-liposome mixture followed by (400 µL, 20 mM) GDL solution addition, stirred and placed onto a silicon ring mold for curing as described above.

In Vitro Release from Hybrid Chitosan or Alginate Hydrogels

A hybrid chitosan or alginate hydrogel (600 µL) was placed in a vail containing 10 mL simulated saliva buffer pH 6.8, or 10 mL 5% dextrose solution. Next, the vail was immersed in a shaking water/ethylene-glycole bath at 37° C. and 100 rpm. An aliquot (200 µL) of the medium was used for quantification; this volume was replaced with fresh buffer or dextrose solution. The fluorescence values of the release media at different time points was recorded at 586 nm, by using an excitation wavelength of 530 nm, attained by Tecan Infinite 200 pro, multimodal micro plate reader, Männedorf, Switzerland.

It should be noted that the saliva simulated saliva buffer is composed of: potassium chloride 0.720 gr/L, $CaCl_2$ dihydrate 0.220 gr/L, NaCl 0.600 gr/L, potassium phosphate monobasic 0.680 gr/L, sodium phosphate dibasic 0.866 gr/L, potassium bicarbonate 1.5 gr/L, potassium thiocyanate 0.060 gr/L and citric acid 0.030 gr/L.

Synthesis of Alginate-Fluorescein

FITC (50 mg, 0.128 mmol) was reacted with an excess of ethylene diamine (60 µL, 0.9 mmol) in 1 mL EtOH for 15 min at room temperature. The solvent was evaporated under reduced pressure by rotary evaporation. The crude product was re-dissolved in MeOH and filtrated through short silica pad. The solvent was evaporated and the primary amine-conjugate to fluorescein was isolated as an orange-red solid. Alginate (1 gr, 3.33 µmol) was dissolved in 100 mL, 50 mM MES buffer pH=6, EDC 104 mg, 0.67 mmol and NHS 118 mg, 1.02 mmol were added to the alginate solution and stirred for 1 hr. After 1 hr, the primary amine-conjugated fluorescein (50 mg, 0.128 mmol) was added. The reaction mixture was stirred for 24 h at room temperature protected from light. The labeled alginate was precipitated with acetone, dissolved in 100 mL DDW and dialyzed against 1% HCl (v/v) and 1% NaCl for 1 week (fresh solution was introduced 3 times a day), followed by freeze-drying (Labconco, Kans., USA). Finally, a yellow-orange solid was isolated and stored at 4° C. until further use.

Synthesis of Chitosan-Fluorescein

Synthesis of chitosan-fluorescein was carried out as previously reported with some modifications. Chitosan (1 gr, 6.66 µmol) dissolved in 100 mL 0.1M AcOH. Fluorescein isothiocyanate (FITC; 25 mg, 64.2 µmol was dissolved in 100 mL MeOH and added to the chitosan solution. The combined solution was stirred overnight at room temperature protected from light. The labeled chitosan was precipitated by 100 mL of 0.1M NaOH. The crude product was filtrated under reduced pressure and the solid was washed with EtOH/DDW 70:30 (% v/v), repeated twice. The labeled chitosan-FITC was dissolved in 100 mL 1% AcOH and dialyzed against 1% AcOH followed by DDW for 48 h, followed by freeze-drying. Finally, as previously stated, a yellow-orange solid was isolated and stored at 4° C. until further use.

Synthesis of Alginate-Thiol

In exemplary procedures, sodium alginate HF120RBS (1 gr) was hydrated in DDW (100 ml) to form a homogeneous solution. The carboxylic acid groups of the polymer were activated by the addition of EDC (0.96 gr) to a final concentration of 50 mM. The reaction was allowed to proceed for 1 h. L-Cysteine monohydrate hydrochloride (2 gr) was dissolved in DDW and added to the reaction solution dropwise till the pH was adjusted to 5.0. At that point 2 M NaOH solution and L-Cysteine were added alternately to maintain pH=5, till all the amount of L-Cysteine was added. The reaction mixture was stirred overnight at room temperature. The resulting alginate-cysteine conjugate was isolated by dialyzing bag with a 12-14 kDa molecular weight cutoff (Spectrumlabs, CA, USA) against 1 mM HCl aqueous solution at room temperature, followed by two cycles of dialysis against 1% NaCl in 1 mM HCl aqueous solution and then thoroughly against 1 mM HCl aqueous solution. Samples were lyophilized by drying frozen aqueous polymer solution at −25° C. and 0.01 mbar. The final product was stored at 4° C. until further use.

Synthesis of Acrylated Alginate (Alginate-PEGAc)

In exemplary procedures, alginate-thiol was dissolved in 0.017 M NaOH solution. TCEP (150% molar excess) was added in order to break any possible intermolecular disulfide bonds. After dissolving the polymer, a 5×molar excess of PEG-DA 10 kDa (calculated based on the thiol content) was added to the solution and the reaction was allowed to proceed for 24 h. The resulting alginate-PEGAc conjugated was isolated by dialyzing bag with a 12-14 kDa molecular weight cutoff against distilled water at room temperature, followed by two cycles of dialysis against 1% NaCl aqueous solution and then thoroughly against aqueous solution. Sample was lyophilized by drying frozen aqueous polymer solution at −30° C. and 0.01 mbar. The final product was stored at 4° C. until further use.

Synthesis of Acrylated Chitosan (Chitosan-PEGAc)

Chitosan (1 gr) was dissolved in 2% (v/v) acetic acid (100 ml) overnight. After dissolving the polymer, PEG-DA 10 kDa (1 gr) was added to the solution. The reaction mixture was stirred for 15 min at room temperature and then for 3 h at 60° C. The resulting chitosan-PEGAc conjugate was isolated by dialyzing bag with a 12-14 kDa molecular weight cutoff against distilled water at room temperature. Sample was lyophilized by drying frozen aqueous polymer solution at −25° C. and 0.01 mbar. The final product was stored at 4° C. until further use.

Synthesis of Alginate-Thiol-PEG-Maleimide (Alginate-SH-PEGM)

In exemplary procedures, alginate-SH-PEGM was synthesized as follows Alginate-thiol (1 gr) was dissolved in 0.017 M NaOH solution (100 ml). TCEP (180% molar excess) was added in order to break any possible intermolecular disulfide bonds. After dissolving the polymer, a 5 fold molar excess of PEG-DM (calculated based on the thiol content) was added to the solution and the reaction mixture was stirred overnight at room temperature. The resulting alginate-PEGM conjugated was isolated by dialyzing bag with a 12-14 kDa molecular weight cutoff against distilled water at room temperature, followed by two cycles of dialysis against 1% NaCl aqueous solution and then thoroughly against aqueous solution. Sample was lyophilized by drying frozen aqueous polymer solution at −25° C. and 0.01 mbar. The final product was stored at 4° C. until further use.

Mucoadhesion and Liposome Release Rate from Hybrid Chitosan Pastes

Chitosan-fluorescein pastes containing liposomes were prepared by dissolving 10, 20 or 30 mg chitosan-fluorescein in 0.4 mL 2% AcOH, pH=4 and 0.6 mL of fluorescently labeled liposome solution. The mixtures were stirred until homogenous viscous solutions were achieved. Chitosan-fluorescein paste (50 μL, 0.25 mg, 3E-6 mol) was spread on porcine's tongue tissue (1 cm×1 cm) and placed in a vail with 10 mL simulated saliva buffer, pH 6.8. In order to estimate the relative influence impurities of unreacted fluorescein contained in the above pastes, chitosan-fluorescein paste was spread on a piece of tissue and inserted into a dialysis bag. The absorbance of this sample was used as a blank. The vails were immersed in a shaking water/ethylene glycol bath at 37° C. and 25 rpm. An aliquot, 200 was used for quantification; and replaced with fresh buffer. The release of chitosan-fluorescein and liposome was quantified by measuring the fluorescence (chitosan-fluorescein: $\lambda_{em}=530$ nm, $\lambda_{ex}(420$ nm, labeled liposome: $\lambda_{em}586$ nm, $\lambda_{ex}530$ nm) of the release medium at different time points.

Characterization of the Synthetic Products $^1$H NMR spectra were recorded on a Bruker Avance 300 spectrometer operating at 300 MHz and Bruker Avance 500 spectrometer operating at 500 MHz, Technion, Haifa, Israel. Fourier transform infrared spectroscopy (FT-IR) study FT-IR spectra were recorded using a Nicolet 6700 FTIR (Thermo Scientific) coupled to a liquid nitrogen cooled mercury-cadmium-telluride (MCT) detector, in attenuated total reflectance (ATR) mode. Spectra were collected in the range of 4000-600 $cm^{-1}$.

Tensile

Tensile assays were performed using a Lloyed tensile machine, Ametek, Berwyn, Pa., USA. Polymer tablet discs were prepared by placing 100 mg of the dry polymer samples in an 11 mm diameter mold and compressing under pressure of 2 metric tons for 1 min. Adhesion assays were performed by attaching the compressed polymer tablet discs to the upper arm of a Lloyed tensile machine using double-sided tape. A fresh small intestine sample (2×3 cm) was attached to the lower arm of tensile machine using vacuum pump. It should be noted, that intestine washing was avoided in order to preserve the mucus layer. The experiment was performed by lowering the upper arm until full contact between the disc sample and the fresh intestine is achieved, followed by applying persistent force of 0.1 N for 10 min. Next, the upper arm was pulled up at a constant rate of 1 mm/min until full detachment was achieved. The adhesion parameter was selected to be the maximum detachment force (MDF). Each result is an average of six independent measurements (n=6). Statistical data analysis was performed using standard t-test with p<0.05 as the minimal level of significance.

Rheology

The viscosities of polymer, mucin and their mixture solutions were measured using Advanced Rheometric Expansion System (ARES) instrument (Rheometric Scientific, NJ, USA). Mucin and polymer were dissolved in 0.1 M PBS pH=6.8 for 2 h at room temperature to yield 140 and 20 mg/ml solutions, respectively. The two solutions were mixed to obtain a final mucin concentration of 70 mg/ml and polymer concentration of 10 mg/ml. The mixture was stirred for 1 h at room temperature, after which viscosity measurements were carried out in the parallel plate geometry (40 mm) at 37° C. and shear rates ranging from 1 to 100 $s^{-1}$.

Mucoadhesion of Alginate Pastes and Liposome Release Rate

Alginate-fluorescein containing liposomes pastes were prepared by dissolving 30, 40 or 50 mg alginate-fluorescein in 0.4 mL DDW and 0.6 mL of fluorescently labeled liposome solution. The mixtures were stirred until homogenous viscous solutions were achieved. Alginate-fluorescein paste (50 μL) was spread on porcine's tongue tissue (1 cm×1 cm) which was glued with cyanoacrylate glue to a weight and placed in a vail with 10 simulated saliva buffer, pH 6.8. One sample (paste on a tissue) was inserted into dialysis bag and the absorbance of this sample was used as a blank. The vail was immersed in a shaking water/ethylene-glycole bath at 37° C. and 25 rpm. An aliquot (200 μL) of eluted liposome medium was removed for quantification; this volume was replaced with fresh buffer. The release of alginate-fluorescein and liposome was quantified by measuring the fluorescence (alginate-fluorescein: $\lambda_{ex}420$ nm, $\lambda_{em}530$ nm, labeled liposome: $\lambda_{ex}530$ nm, $\lambda_{ex}586$ nm) of the release media at different time points.

DLS

Liposome size distribution was measured by dynamic light scattering (DLS). Stability of the liposome was evaluated by measuring the particle size during liposome release experiment at different time point. DLS data of liposome samples were compared to the original liposome solution.

Small angle x-ray scattering (SAXS)

SAXS experiments were performed using a small-angle diffractometer (Molecular Metrology SAXS system with Cu Kα radiation from a sealed micro focus tube (MicroMax-002+S), two Gobel mirrors, and three-pinhole slits; generator powered at 45 kV and 0.9 mA). The scattering patterns were recorded by a 20×20 cm two-dimensional position sensitive wire detector (gas filled proportional type of Gabriel design with 200 μm resolution) that is positioned 150 cm behind the sample. The scattered intensity I(q) was recorded in the interval 0.008<q<0.25 Å-1, where q is the scattering vector defined as $q=(4\pi/\lambda)\sin(\theta)$, where 2θ is the scattering angle, and λ is the radiation wavelength (1.542 Å). The solution under study was sealed in a thin-walled capillary (glass) of about 2 mm diameter and 0.01 mm wall thickness; measurements were performed under vacuum at 37° C. The scattering curves were normalized by correcting for counting time and sample absorption. The data was additionally normalized to the scattering cross-section of an electron, also known as the Thompson scattering length or Lorentz radius, equal to $7.94*10^{-26}M^2$. The scattering of the solvent was subtracted from all curves prior to data analysis.

Polymer Retention Study

Mucoadhesion studies of alginate and cross-linked alginate pastes were performed on porcine tongue mucosa using a home-made flow apparatus, as previously described. The chamber consists of a channel, half a pipe, which was anchored on a stand at 45° angle. Porcine's tongue tissue was used as a substrate, the tissue was thawed for 5 minutes in 100% humidity and a temperature of 37° C. Fluorescein labeled alginate paste or cross-linked fluorescein labeled alginate (50 μl) were placed on the piece of tissue (1.5 cm×3.0 cm) and allowed to incubate in the dark at 37° C. and 100% humidity for 30 min. Next, simulated saliva buffer was dripped onto the substrate at a constant rate of 2.25 mL/min (at least 17 mL), using a syringe pump. The collected liquid, aliquots of ~1 mL each, were measured fluorescently using a Tecan plate reader ($\lambda_{em}$530 nm, $\lambda_{ex}$420 nm). The labeled polymer concentration was calculated using a calibration curve on the native labeled polymer in simulated saliva buffer following precise measurement of its volume. All measurements were performed in triplicates.

Liposome Preparation

Liposomes either empty or containing proteins were prepared as follows: Initially, 1,2-dimyristoyl-sn-glycero-3-phosphocholine (DMPC, Lipoid, Germany) and cholesterol (Sigma Aldrich) in molar ratio of 60:40 were dissolved in chloroform. 1% v/v of a 2 mg/ml 14:0-Rhodamine (Avanti polar lipids, Inc, Alabama, USA) stock solution was added to the chloroform solution. Then the solvent was evaporated using rotary evaporator (BUCHI Labortechnik AG, Postfach, Switzerland) enabling the creation of a thin lipid film. The film was hydrated with either 5% dextrose (w/v) or 10% PBS (v/v) (Sigma Aldrich) while rotating, for empty liposomes and for protein loaded liposomes the film was hydrated with 5 mg/ml Bovine Serum Albumin (BSA) in 10% PBS. The dispersion became milky indicating the spontaneous formation of lipid vesicles. Nanoscale vesicles were created with stepwise extrusion through polycarbonate membranes (GE healthcare, Wauwatosa, Wis., USA) using 200 nm pore size membranes in a 10 ml extrusion system (Northern Lipids, Vancouver, Canada) at 45° C. The non-encapsulated solution was removed by ultracentrifugation (150,000×g, 45 min, 4° C.) and the pellet was re-suspended with either 5% (w/v) dextrose or 10% PBS.

Preparation of Liposome-Containing Alginate Formulations

Hydrogels:

alginate was dissolved in DDW (blank gels, without liposome) or in liposome solution prepared from 100 mM DMPC (marked with rhodamine) and cholesterol (60:40 molar ratio) in 5% dextrose. Ca-EGTA solution (100 Mm) was added followed by 20 mM GDL solution. The mixture was stirred for 1 min and 600 μL solution was placed into a silicon ring (14 mm) used as a mold. The mixture was left to cure overnight at room temperature in a close petri plates.

Pastes:

pastes were prepared by dissolving 40 mg alginate or alginate-SH, or 300 mg alginate-PEGAc.

Control for release experiments was 0.015 mmol of liposome in 10 mL buffer or dextrose solutions (no gel).

Preparation of Doxorubicin Liposomes

Active liposomes encapsulation of doxorubicin was performed by an ammonium sulfate gradient according to Haran et al. [Biochim. Biophys. Acta 1151 (1993) 201-215]. Liposomes composition and thin film preparation was performed without the addition of Rhodamin. The hydration of the lipid film was performed with 125 mM ammonium sulfate solution at 50° C. The resulting mixture was stirred vigorously followed by extrusion five times, as described above. Dialysis exchanges of 5% glucose were used to remove the external ammonium sulfate from liposomes. After dialysis, 1 mg/mL of doxorubicin were added to the liposomes for 1 hr at 50° C. in a shaker and then placed on ice for 1 minute. In order to remove non-encapsulated doxorubicin the liposomes were ultra-centrifuged (150,000× g, 1 hr, 4° C.). The liposomes pellet was resuspended with either 5% dextrose or 10% PBS. The percentage of encapsulated doxorubicin within the liposome was determined by High Performance Liquid Chromatography (HPLC).

Preparation of 5-FU Liposomes

Liposomes composed of DMPC/Cholesterol (60:40 molar ratio) were dissolved in chloroform. The solvent was evaporated to dryness under reduced pressure at 51° C. to form a thin lipid film. The hydration of the lipid film was performed with 5 mg/ml of 5-FU solution (10 mM PBS, 138 mM NaCl) at 51° C. The resulting mixture was stirred vigorously, followed by extrusion (ten times). Extrusion was performed at 51° C. through a stack of two polycarbonate membranes (400 nm and 200 nm). To ensure the liposome size (200 nm) dynamic light scattering (DLS) was used. In order to remove non-encapsulated 5-FU, the liposomes were ultracentrifuged (150,000×g, 1 hr, 4° C.). The liposomes pellet was resuspended with 10% PBS.

Liposome Release from Alginate Formulation

Hydrogels: Alginate gel (600 μL) was placed in a vail containing 10 mL 0.01M PBS (pH=6.8, 8 gr/L NaCl) or 10 mL 5% dextrose solution. Then, the vail was immersed in a shaking water/ethylene-glycole bath at 37° C. and 100 rpm. An aliquot (200 μL) of eluted liposome medium was removed for quantification; this volume was replaced with fresh buffer or dextrose solution. The release of the liposome was quantified by measuring the fluorescence ($\lambda_{em}$586 nm, $\lambda_{ex}$530 nm) of the release media at different time points using a Tecan infinite 200 pro, multimodal microplate reader, Mannedorf, Switzerland.

Pastes:

Alginate paste (50 μL) was spread on a piece of tissue which was glued with cyanoacrylte glue to a weight and placed in a vail with 10 ml 0.01M PBS, pH=6.8. Then, the vail was immersed in a shaking water/ethylene-glycole bath at 37° C. and 25 rpm. An aliquot (200 μL) of eluted liposome medium was removed for quantification; this volume was replaced with fresh buffer. The release of liposome was quantified by measuring the fluorescence ($\lambda_{em}$586 nm, $\lambda_{ex}$530 nm) of the release media at different time points using a Tecan infinite 200 pro, multimodal microplate reader, Mannedorf, Switzerland.

Protein Release from Liposomes in Alginate Formulation

Protein release from hybrid liposome alginate gel system was measured over 120 hr. Hybrid system was prepared as described above, for empty liposomes, BSA loaded liposomes and a control system with BSA in alginate (without liposomes). Gels were agitated in 7.5 ml of 10% PBS at 37° C. Samples of 200 µl were taken over time and tested for protein concentration (BCA assay, Thermo Scientific), and for fluorescence of Rhodamin ($\lambda_{em}$586 nm, $\lambda_{ex}$530 nm).

Cell Culture

The human tongue squamous cell carcinoma cell line, CAL-27 was obtained from the American Type Culture Collection (ATCC, Manassas, Va., USA). The cell line was cultured in DMEM supplemented with 10% (v/v) FBS, 2 mM L-glutamine, 100 Units/ml penicillin and 100 µg/ml streptomycin in a humidified atmosphere containing 5% (v/v) CO2 and 95% (v/v) air at 37° C. Cells were detached by 0.25% (w/v) trypsin/0.02% (w/v) EDTA and split every 2-3 days to maintain cell growth.

Toxicity of Drug Loaded Hybrid Polymer/Liposome System to Cells

The cytotoxicity of chemotherapeutic drugs to CAL-27 cells was determined using the MTT assay. Cells were plated in 96-well plate in density of 50,000 cells per well in a total volume of 200 µl medium. After 24 hours the cells were treated with different drugs and liposomes for 24 h and 48 h. All experiments were done in quadruplicates.

MTT Assay

Cell viability was evaluated by MTT assay, a colorimetric assay based on the ability of viable cells to reduce a soluble yellow MTT substrate to a blue formazan crystal by mitochondrial succinate dehydrogenase activity of viable cells. This test is a good index of mitochondrial activity and thus of cell viability. After 24 or 48 hr of treatment, the medium was aspirated, and 100 µL of MTT, 1 mg/mL in PBS were added to each well. After MTT addition the plates were covered and returned to the incubator at 37° C. for 2 hr, the optimal time for formazan product formation. After 2 hr of incubation, the formazan product was dissolved by adding an amount of MTT solubilization solution, and the plate was incubated for 1 hr for dissolution enhance. The absorbance was measured at 570 nm and the background absorbance measured at 690 nm.

In exemplary procedures, alginate gels incorporating either empty or doxorubicin loaded liposomes were prepared as described above, in a volume of 100 µL each with liposome proportion of 6.7%, 16.7% and 33.3% (v/v). To determine the toxicity of this drug loaded hybrid systems to CAL-27 cells, cells were initially plated in 24-well plate in density of 50,000 cells per well in a total volume of 500 µL medium. After 24 hr, medium was replaced and alginate gels (control, with empty liposomes, or with doxorubicin loaded liposomes) were placed in the cells for 24 and 48 hr. Viability was measured using the MTT assay. All experiments were done in quadruplicates.

Example 1

Building an Apparatus for Assessing Paste Adhesion

Figure 1A:
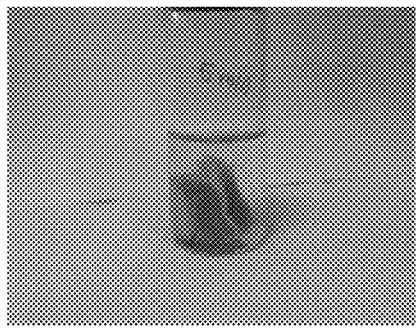
FIGS. 1A-B present a photograph showing the experimental setup (FIG. 1A); and a graph showing the fractional release of sulforohdamine B vs. time into 0.01M phosphate buffered saline (PBS), pH=6.8, at 37° C.
Figure 1B:
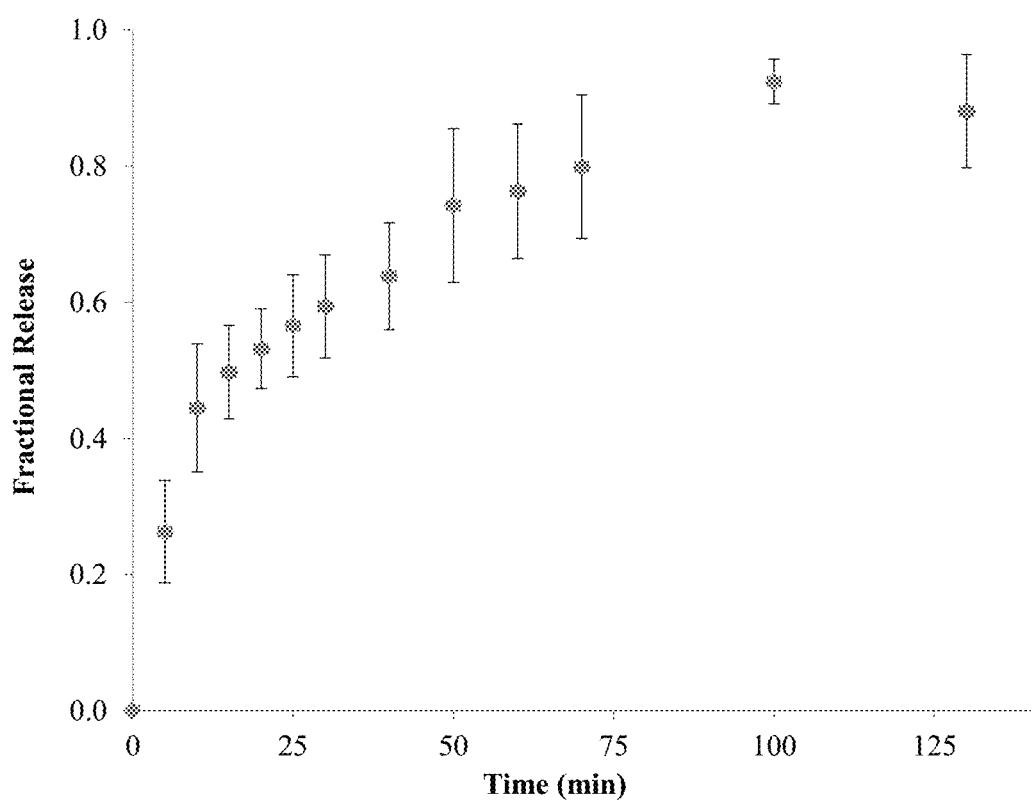

A home-made apparatus was designed, based on a flow cell for assessing the mucoadhesion of pastes and viscous polymer solutions under shear flow conditions. The experiment was set up by mixing viscous solution of alginate with the fluorescent dye solution, by that, the fluorescent dye was non-covalently attached to alginate. The pastes were spread on a slice of porcine tongue simulating the target tissue. The tissue holding the paste was placed in a vial and was subject to shear flow while immersed in PBS solution (see FIG. 1A). The release rate of the fluorescent marker to the PBS media was examined and is shown in FIG. 1B.

As can be seen, the fluorescent marker was completely released to the external PBS solution after two hours.

Since the dye is physically entrapped within the paste, it is likely that two mechanisms are involved in its release: diffusion of the dye out of the polymer, and polymer dissolution. Although complete release within 2 hr seems to be appropriate for clinical use, it is important to understand the balance between the release mechanisms better. Furthermore, polymer dissolution is related to the cohesive strength of the paste and to its mucoadhesion properties. In order to investigate polymer dissolution; alginate and chitosan were covalently attached to fluorescein, allowing the accurate monitoring of polymeric chain's release rate from the surface. These experiments are currently ongoing.

Figure 2A:
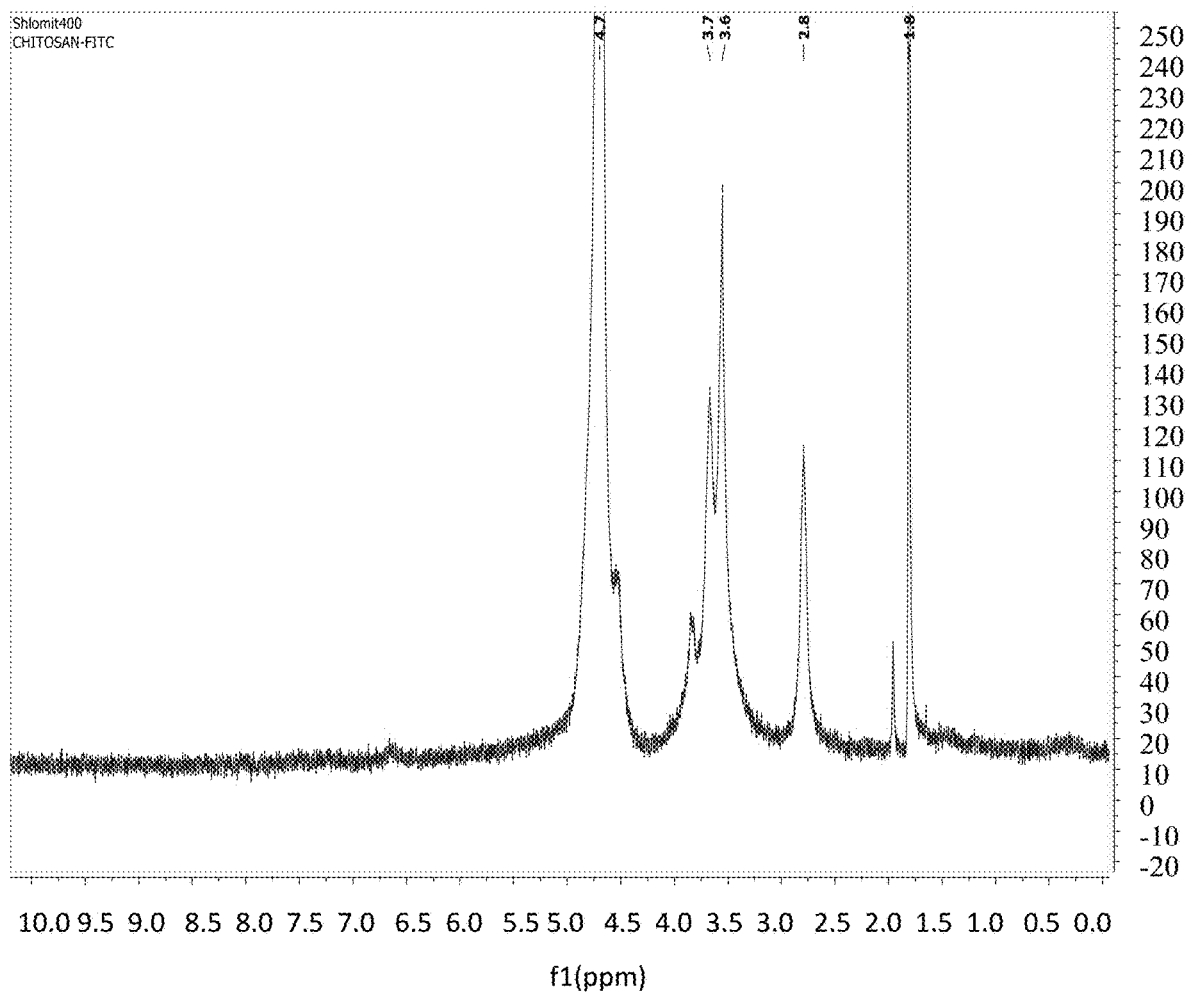
FIGS. 2A-B present $^1$H NMR spectra of chitosan-fluorescein in $D_2O$ (FIG. 2A); and FT-IR spectra of: 1. fluorescein, 2. chitosan, and 3. chitosan-fluorescein (FIG. 2B).
Figure 2B:
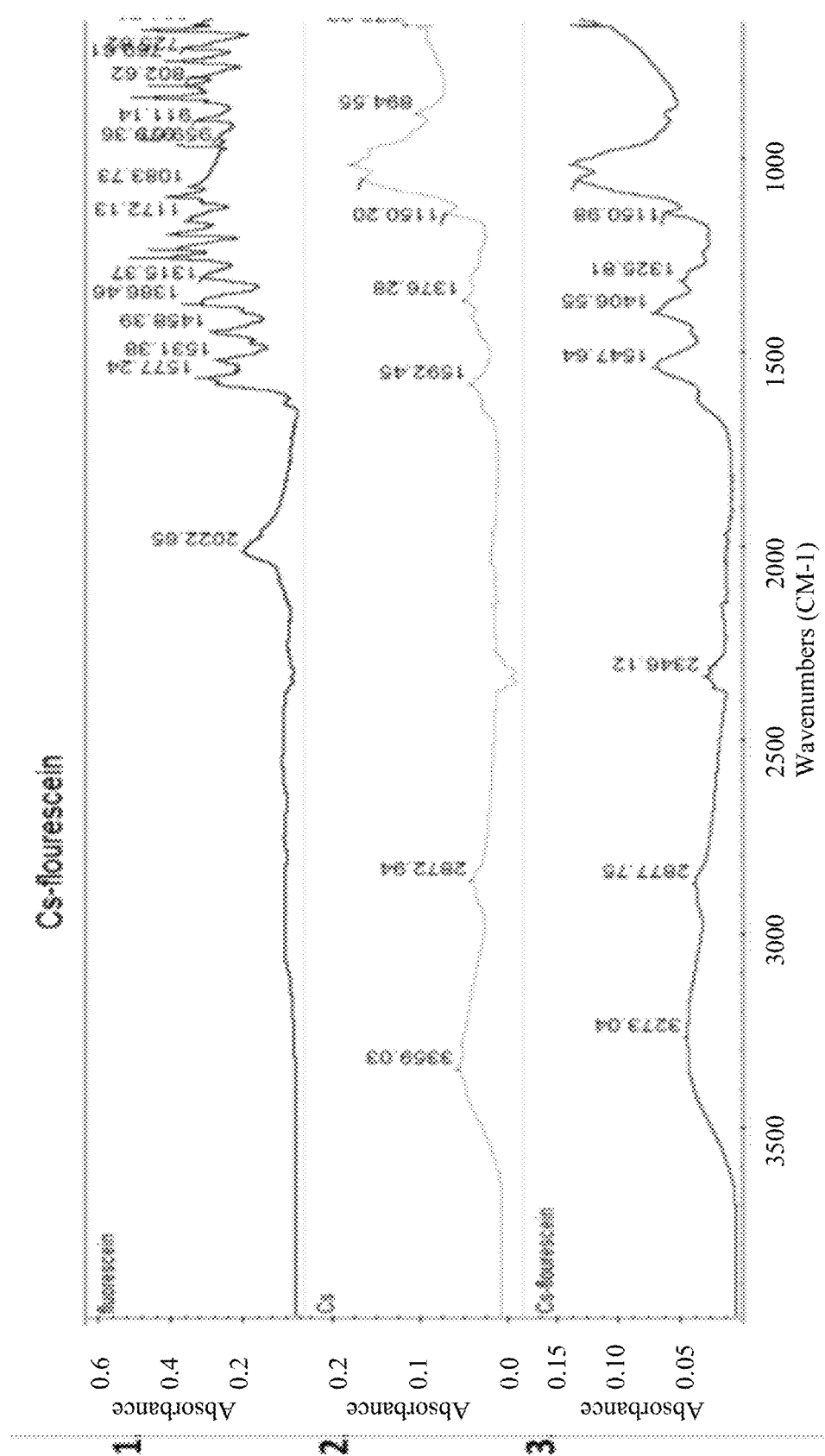
Figure 3A:
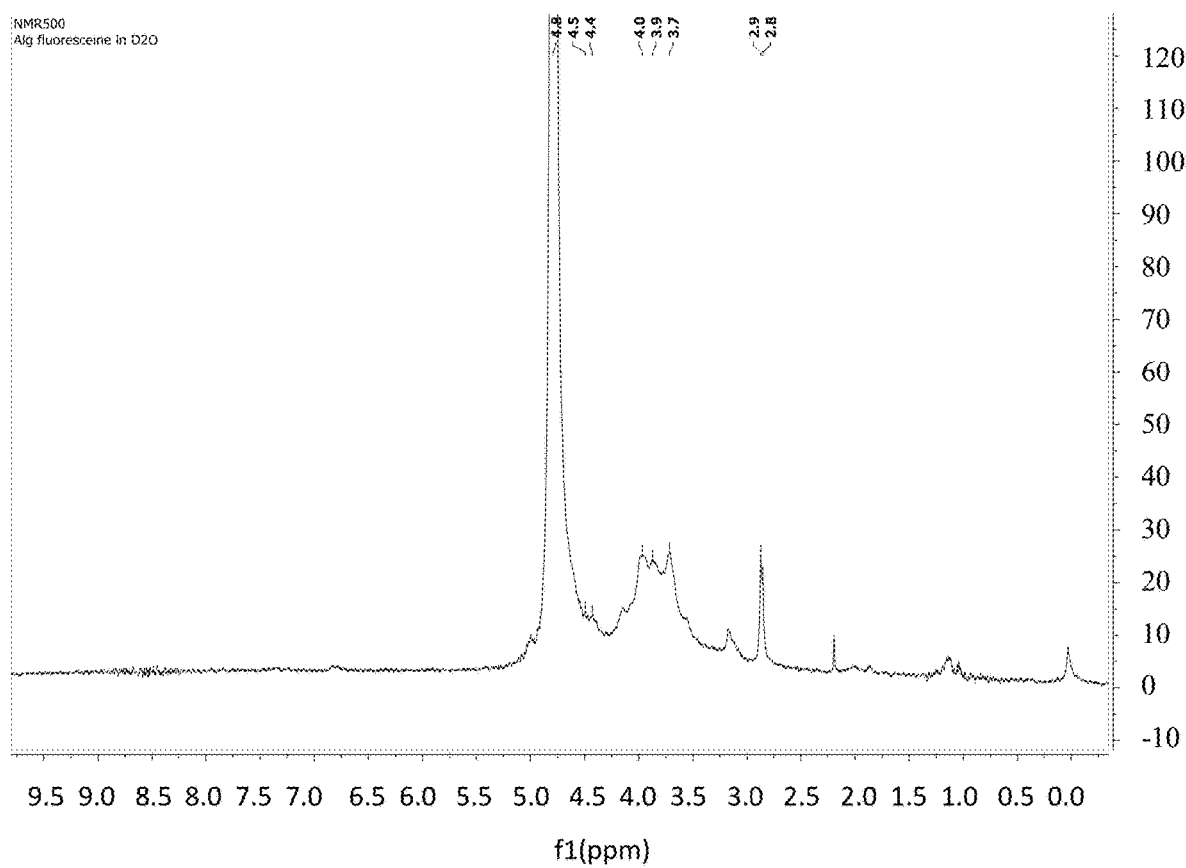
FIGS. 3A-B present $^1$H NMR spectra of alginate-fluorescein in $D_2O$ (FIG. 3A); and FT-IR spectra of: alginate-fluorescein 2. fluorescein, and 3. alginate (FIG. 3B).
Figure 3B:
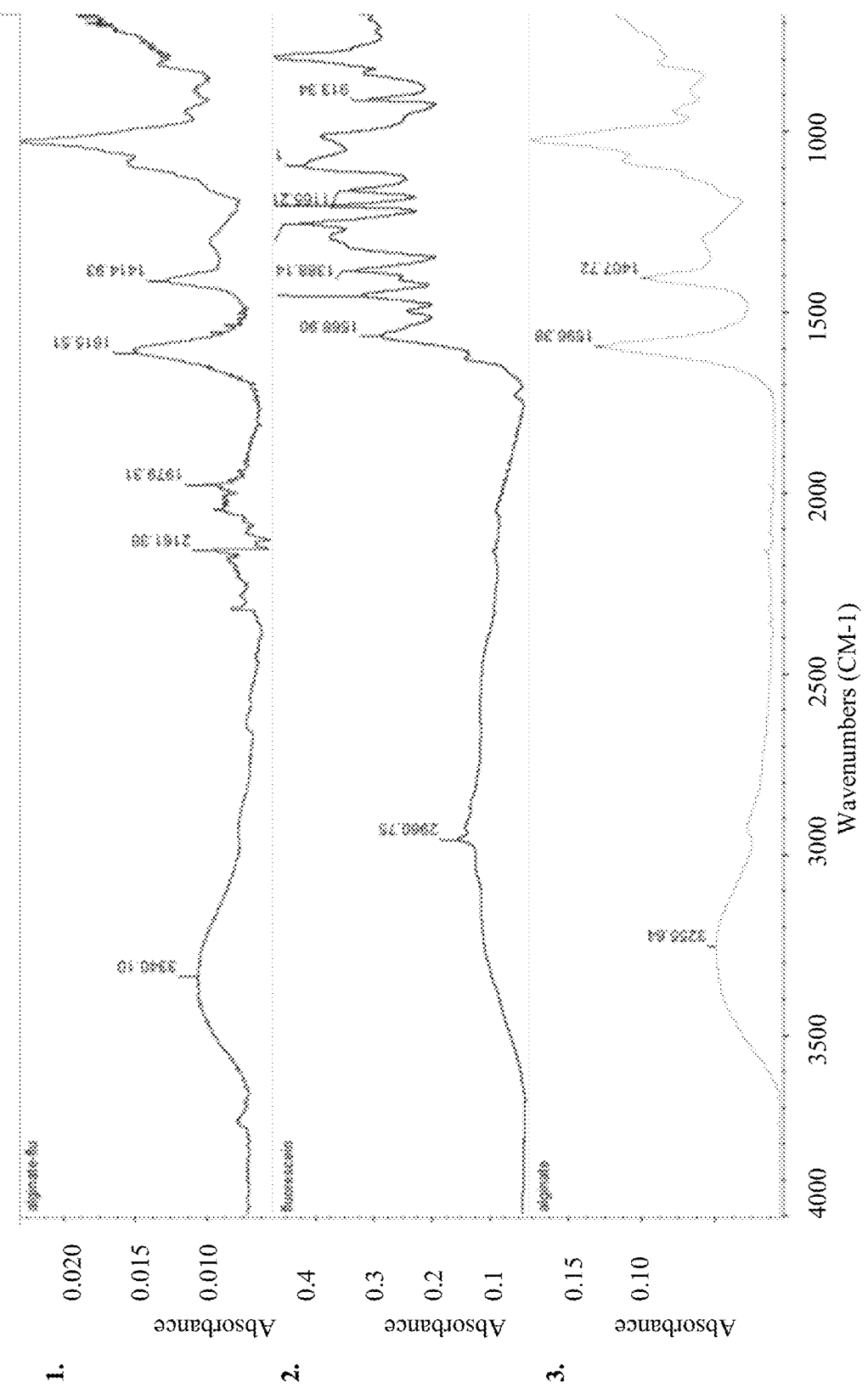

The synthesis of the labeled polymers was aimed to ~1.5% activation of chitosan's amines or alginate carboxylic acid, therefore, no significant changes in the NMR spectra of the labeled chitosan or alginate polymers as relative to the native polymer. However, some changes were observed in fourier transform infrared spectroscopy (FT-IR) spectra and compared to the native polymer and fluorescein (see FIGS. 2B and 3B).

Example 2

Synthesis and Characterization of Chitosan Acrylates

Figure 4A:
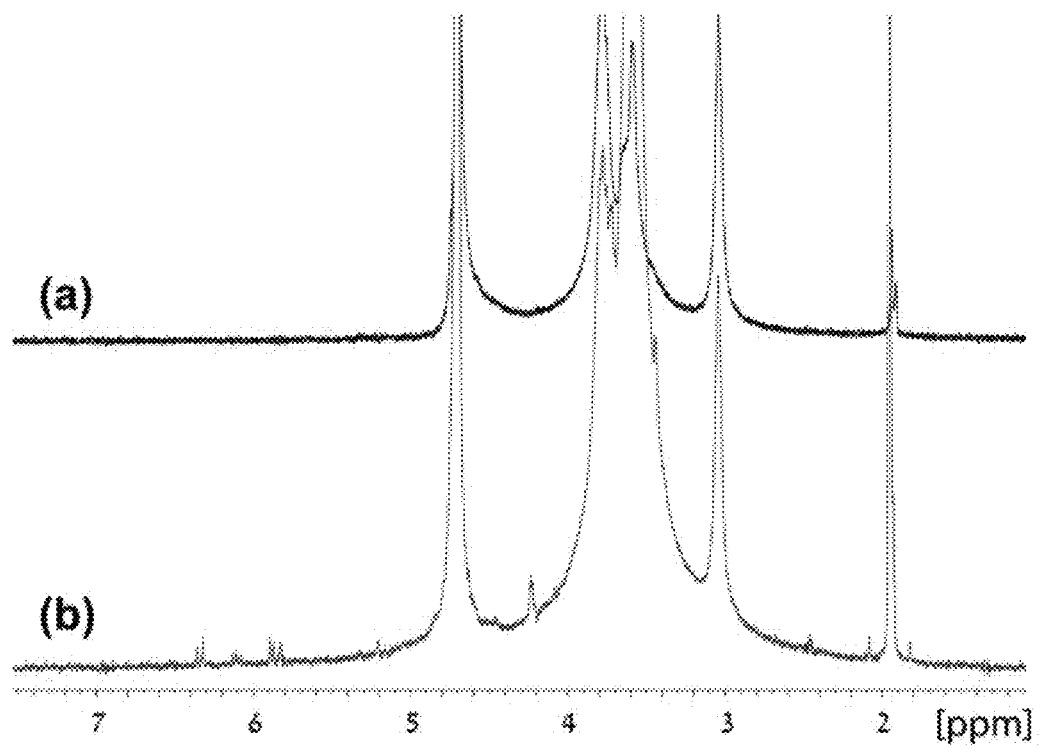

Chitosan-PEGAc was prepared in one synthetic step by nucleophilic addition of the chitosan's nitrogen on PEGDA. $^1$H NMR analysis revealed the acrylate's protons in the range of 5.8-6.4 ppm and chitosan's protons in the range of 3-4.2 ppm (as shown in FIG. 4A).

As detailed in Table 1, three products with different molar ratios were prepared. The highest PEGDA concentration used was 9/1 (nine primary amine groups of chitosan to one PEGDA chain). While preparing samples for further experiments, it was noticed that the polymer has very high solubility in water—which can be expected, as increasing the concentration of PEGDA with a high molecular weight makes the molecule more hydrophilic. The high solubility made this molecule irrelevant for drug delivery purposes since it dissolved in the medium immediately. Therefore, the focus was given to a molar ratio of 47/1, in which one PEGDA chain is used for every 47 primary amine groups. This ratio produced a polymer from which tablets that are stable in an aqueous medium could be prepared.

Synthesis Using PEGDA with an Mw of 0.7 kDa

Given that it was impossible to achieve a molar excess with PEGDA with an Mw of 10 kDa, a shorter PEGDA with an MW of 0.7 kDa. 6.6% (w/v) of PEGDA with a molar mass of 0.7 kDa was used to achieve a molar ratio of 1:2, i.e., two PEGDA chains for each primary amine group of chitosan, and 13.4% (w/v) for a molar ratio of 1:4.

Tensile Strength

Figure 4C:
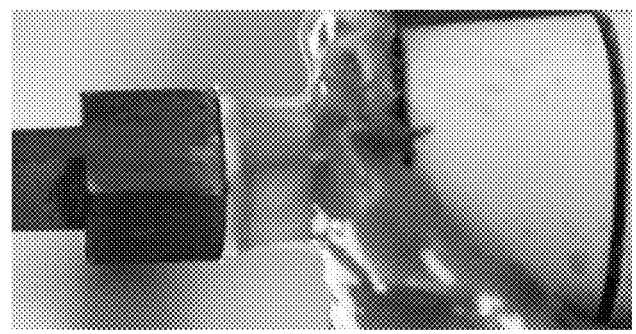
Figure 4B:
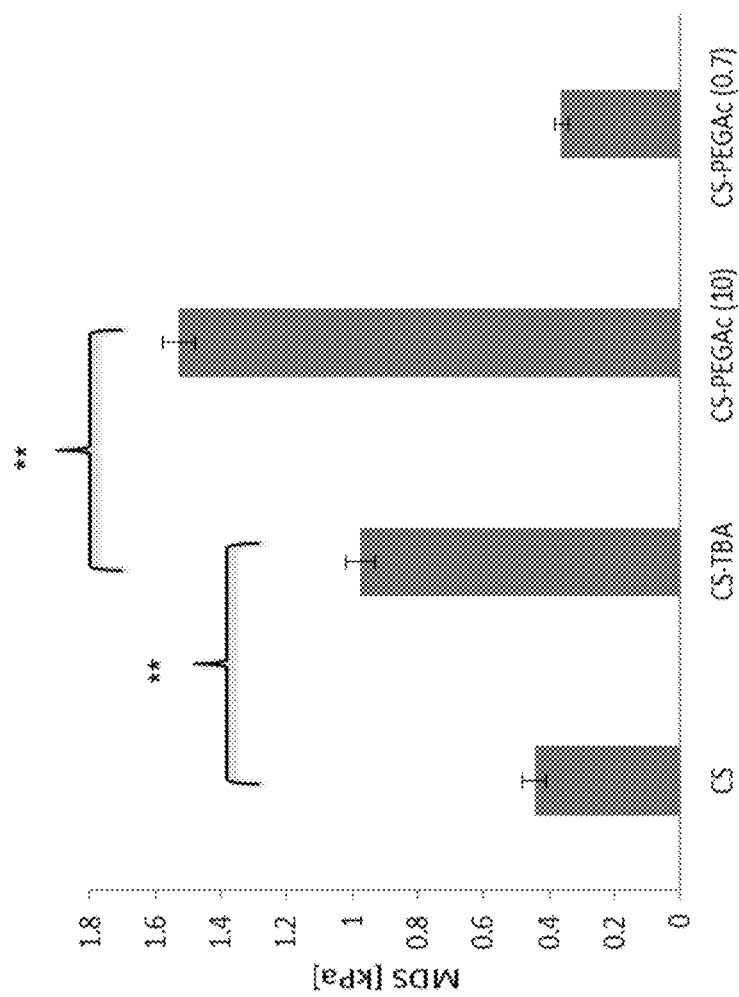
Figure 4H:
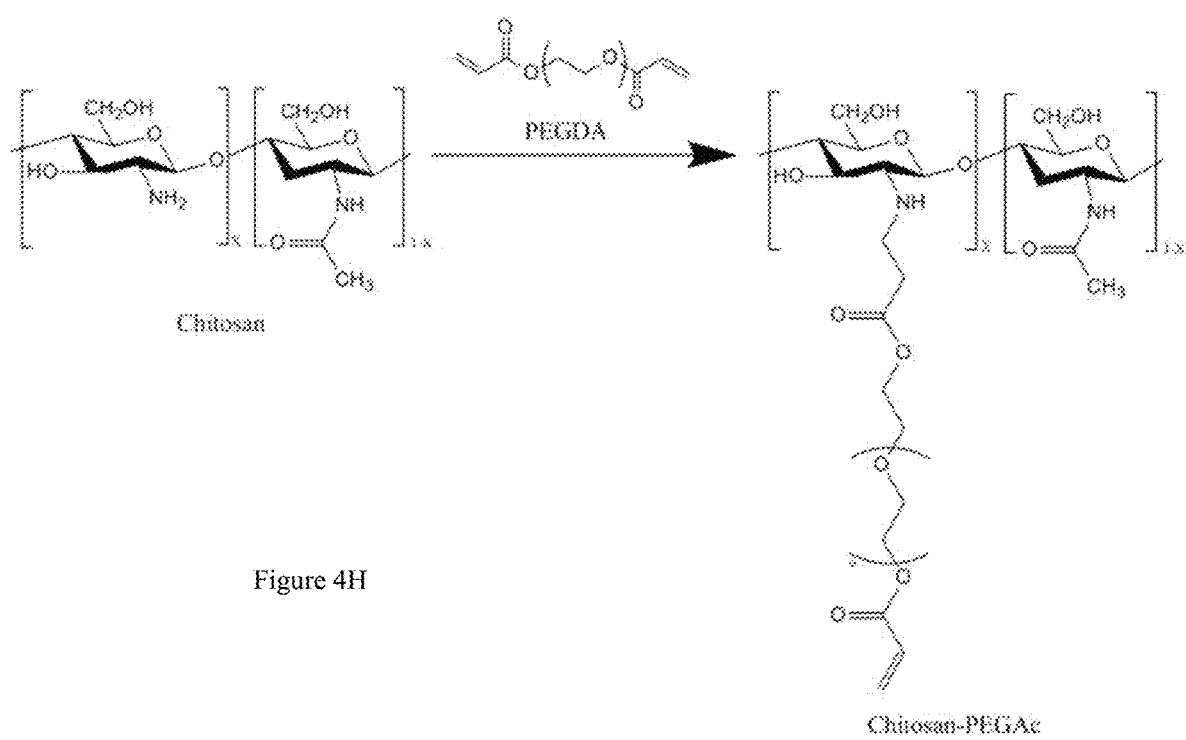

Mucoadhesion was first characterized by a tensile study. FIG. 4B demonstrates that the maximum detachment strength (MDS) of chitosan-PEGA(10) is significantly higher than that of the thiolated chitosan (chitosan-TBA) (p<0.01), which in turn is significantly higher than that of chitosan (p<0.01). The new polymer, chitosan-PEGA(10), presents further improvement in mucoadhesive properties compared to the other two polymers. The improved adhesion can be attributed to the unsaturated functional group carried by PEGA, which increases the probability of creating covalent bonds between the polymer and the mucin on the tissue.

Surprisingly, although chitosan-PEGA(0.7) has a high degree of acrylation, its MDS value was not significantly different from that of chitosan (p<0.5), whereas chitosan-PEGA(10) with only 30% acrylation is five times more adhesive than chitosan. The high adhesion of chitosan-PEGA(10) could be visually observed in a photograph taken during the detachment of the polymeric tablet from the tissue; see FIG. 4C.

Rotating System

To be of practical use as mucoadhesive drug delivery vehicles, the polymer must survive and function in a hydrated environment. Therefore, mucoadhesion using a rotating system was also assessed. Table 1 below summarizes the retention time of dry compressed polymer tablets on porcine small intestinal mucous. Due to technical limitations, it was not possible to observe the tablets for more than 6 h. It was found that the detachment time of both chitosan-PEGA(10) and chitosan-TBA from porcine small intestinal mucous was higher than this limit.

The corresponding detachment time of chitosan was 1.1 h±0.2. Chitosan-PEGA(0.7) disintegrated in the medium after only one minute, probably due to the high grafting density of short PEG chains, which on one hand are too short to form a network, and on the other hand, may interrupt the entanglements of chitosan and make it less stable in the physiological medium. Based on these results, it can be concluded that the mucoadhesion of both chitosan-PEGA (10) and chitosan-TBA is larger than that of chitosan. These findings are in line with those of the tensile studies. However, the maximum observation time limitation does not allow us to conclude whether chitosan or chitosan-TBA is more efficient in this case.

Qualitative support for the enhanced mucoadhesion of chitosan-PEGA(10) compared to chitosan can be seen in FIG. 4D, which shows a photograph of chitosan and chitosan-PEGA(10) tablets after 30 minutes of experiment. It is apparent that the chitosan tablet retained its original shape and size while the chitosan-PEGA(10) tablet integrated with the tissue, possibly indicating better interactions with the tissue's mucous layer.

TABLE 1

| Polymer | Retention time [h] |
|---|---|
| Chitosan | 1.1 ± 0.2 |
| Chitosan-TBA | >6 |
| Chitosan-PEGAc(10) | >6 |
| Chitosan-PEGAc(0.7) | 0.01 ± 0.005 |

Retention time of dry compressed polymer samples on porcine small intestinal mucous. Mucoadhesion studies were performed in 0.1 M PBS pH 7.4 at 37° C. Indicated values are means±SD (n≥4).

Assessment of Mucin/Polymer Interaction

Rheology measurements were performed to provide information on interactions between mucin glycoproteins and chitosan-PEGA.

Synergistic increase in viscosity can be observed in FIG. 4E, where the viscosity of the chitosan-PEGA(10)/mucin mixture is higher than the additive viscosity of these components separately. On the other hand, as can be seen in FIG. 4F, the viscosity of the chitosan-PEGA(0.7)/mucin mixture is similar to mucin's viscosity, which means that the synergistic effect is not observed in this case.

Thus, these observations provide additional evidence of the superiority of chitosan-PEGA(10) over chitosan-PEGA (0.7).

It can be also seen from FIG. 4G that the viscosity of mucin solutions decreases when the shear rate increases, indicating that mucin displays shear-thinning behavior. On the contrary, the studied acrylated chitosan solutions display an almost Newtonian behavior, as apparent from the very small dependence of the viscosity on the shear rate (FIG. 4G).

The volume of the polymeric chain of chitosan-PEGA(10) in the solution is larger than that of chitosan-PEGA(0.7), leading to increased viscosity. As for mucin-acrylated chitosan mixtures, while the chitosan-PEGA(10)/mucin mixture displayed pronounced shear-thinning behavior, the viscosity of chitosan-PEGA(0.7)/mucin is almost Newtonian (FIG. 4G). In case of chitosan-PEGA(10), the high weight concentration and the high molecular weight increases the molecular volume of the polymer/mucin complex hence leading to shear-thinning behavior.

Another interesting phenomenon is the differences in the viscosities of the polymer/mucin mixtures at high shear rates. While the ultimate viscosity of chitosan-PEGA(0.7)/ mucin is similar to that of mucin, the viscosity of the chitosan-PEGA(10)/mucin mixture is higher than that of mucin. To quantitatively determine the high shear rate viscosity, the flow curves were fitted to a Cross model using the Equation below (Cross, 1965; Macosko, 1994; Picout & Ross-Murphy, 2003)

$$\eta = \eta_\infty + \frac{\eta_0 - \eta_\infty}{1 + (\lambda\dot{\gamma})^{1-n}},$$

where $\eta_0$ is the low shear rate viscosity, $\eta_\infty$ is the high shear rate viscosity, $\lambda$ is time constant related to the relaxation time of the polymer in solution and n is the power law flow behavior index. Fitting was performed using a non-linear regression analysis in Excel. Equation parameters ($\eta_0$, $\eta_\infty$) and their coefficients of variations were estimated and the goodness-of-fit was assessed by least squares analysis.

Table 2 summarizes the cross model best-fit parameters, showing non-linear regression parameters for the Cross model of 5% mucin and of polymer/mucin mixtures as calculated by the Cross model. It can be seen that the high shear rate viscosity of the mucin solution and of the chitosan-PEGA(0.7)/mucin mixture is zero, while the high shear rate viscosity of the chitosan-PEGA(10)/mucin mixture is higher.

At high shear rates, molecular chain alignments and disentanglements occur since the rate of destruction of entanglements is higher than the formation of new entanglements, leading to orientation of polymer chains in the direction of the flow and decreasing the viscosity (Menchicchi et al., 2014; Tomioka and Matsumura, 1987). It is likely that polymer/mucin complexation is based both on physical and chemical interactions. A high shear rate may be capable of breaking physical interactions and disentangling the polymer; covalent bonds, however, are much more difficult to destroy. The viscosity of the chitosan-PEGA(10)/mucin mixture decreases dramatically but still stays high even at high shear rates, which may be indicative of strong chemical bonds between the mixture's components.

TABLE 2

| Sample | $\eta_0$[Pa * s] | $\eta_\infty$[Pa * s] | λ | n | R2 |
|---|---|---|---|---|---|
| Mucin 5% | 0.046 | 0 | 0.215 | 0.618 | 0.011 |
| Chitosan-PEGA(0.7)/mucin | 0.02 | 0 | 0.027 | 0.414 | 0.009 |
| Chitosan-PEGA(10)/mucin | 0.087 | 0.02 | 0.139 | 0.024 | 0.001 |

Example 3

Characterization of Alginate-SH-PEGM

Alginate-SH-PEGM Synthesis

In exemplary procedures, a new polymer, alginate-SH-PEGM was explored. Since the reactivity of PEGM in Michael-thiol addition reaction is higher than that of acrylate, it was expected that this polymer will display better mucoadhesive properties. The synthesis of alginate-SH-PEGM was performed by two semi-synthetic steps as described herein.

Figure 5A:
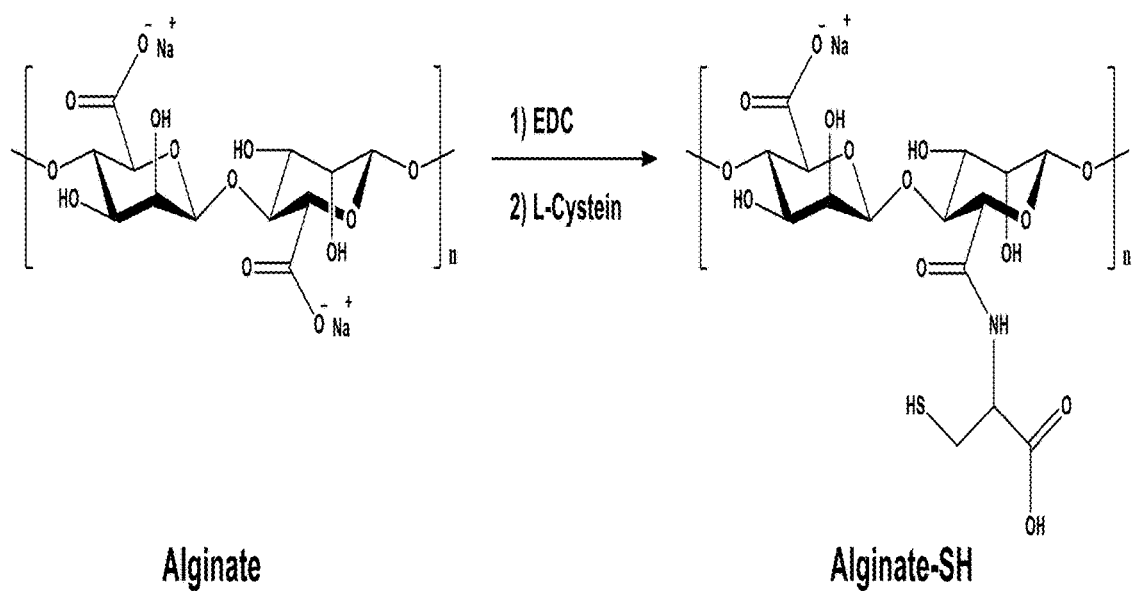
FIGS. 5A-B present schemes of synthesis of alginate-SH (FIG. 5A; scheme 1), and synthesis of alginate-SH-PEGM (PEGM; poly(ethylene glycol) microspheres) (FIG. 5B; scheme 2).
Figure 5B:
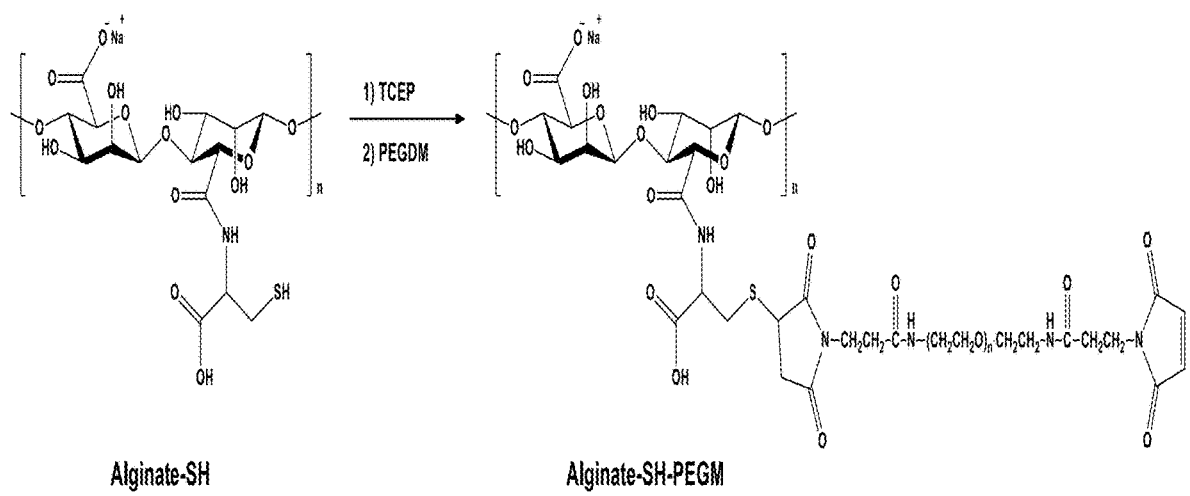

The first step was preparation of alginate-thiol by conjugation reaction of alginate and cysteine which followed a procedure summarized in Scheme 1 in FIG. 5A. In next step, nucleophilic substitution of the thiol end group on PEGDM afforded the Michael addition adduct. TCEP was added to the reaction in order to avoid disulfide bonds formation (Scheme 2 in FIG. 5B).

Alginate-SH-PEGM Characterization

Figures 6A, 6B, 6C:
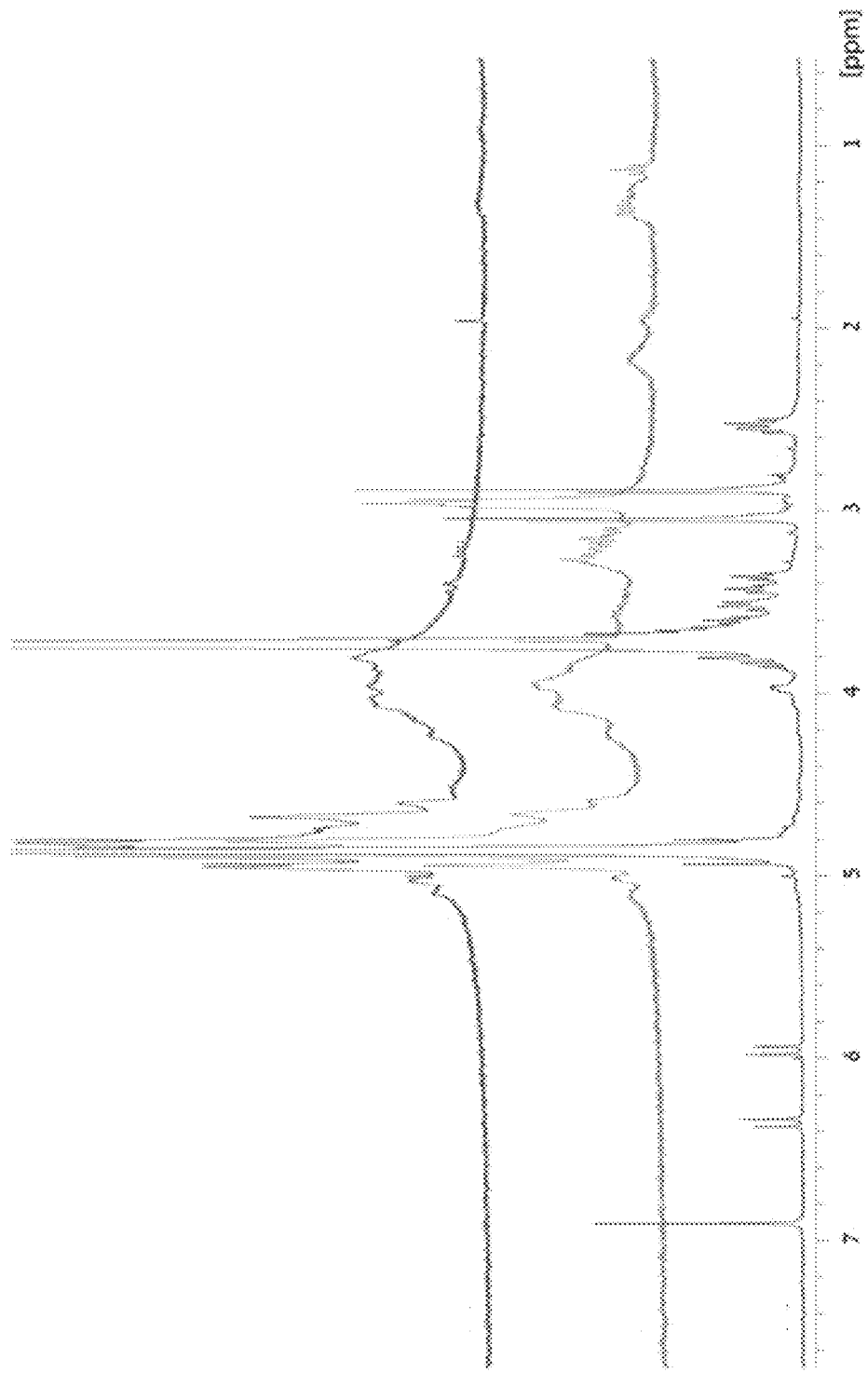
FIGS. 6A-C presents $^1$H NMR spectra of 15 mg/ml: alginate (FIG. 6A), alginate-SH (FIG. 6B) and alginate-SH-PEGM at 25° C. in $D_2O$ (FIG. 6C).

The molecular structure of the starting material, alginate, the intermediate alginate-SH and the resulted product alginate-SH-PEGM were analyzed using NMR spectra. The peaks typical to alginate are seen in the range from δ=3.5 to δ=4.5 ppm (as shown in FIG. 6A). It can be also observed that the reaction intermediate, alginate-SH, has additional peaks typical to cysteine, in the range from δ=3.0 to δ=3.5 ppm (as shown in FIG. 6B). In addition to the NMR, the thiol presence was verified using Ellman's reagent reaction and its concentration was found to be 297.6 μmol thiol/gr alginate. Alginate-SH-PEGM, the desired product, contains several new types of protons: the spacer's amide proton, located at δ=6.9 ppm; double bond protons of the maleimide group, located at δ=5.9 and δ=6.3 ppm; two methylene groups of the repeating unit of PEG, located at δ=3.7 ppm, and four different methylene groups of the spacer that are located at δ=3.3, δ=3.4, δ=3.5 and δ=3.6 ppm (as shown in FIG. 6C). The peak located at δ=4.87 is water's protons.

Assessment of the Mucoadhesion Properties

Figure 7:
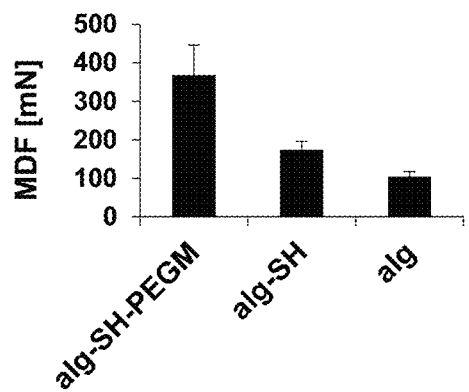
FIG. 7 presents a bar graph showing the maximum detachment force (MDF) of dry compressed polymer samples. The results are significantly different (P<0.0002).

For the characterization of mucoadhesion ability, tensile study was conducted. FIG. 7 depicts that maximum detachment force (MDF) of alginate-SH-PEGM is significantly higher than of alginate-SH, which in turn is significantly higher than alginate. The new polymer alginate-SH-PEGM presents improved mucoadhesive properties compare to the other two polymers. The maleimide functional group has two reactive carbons and two carbonyl groups that increase the possibility of creating covalent bonds and additional hydrogen bonds, respectively.

Figure 8:
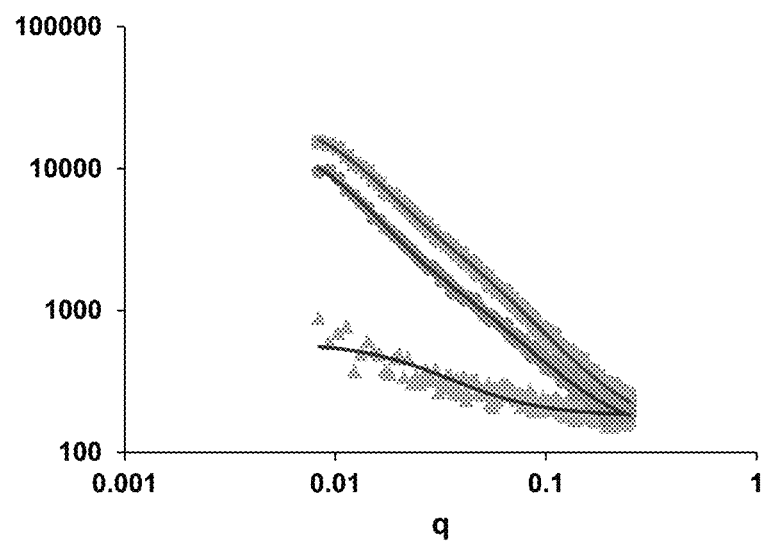
FIG. 8 presents small angle x-ray scattering (SAXS) curves of (▲) PEGDM 2%, (■) Mucin 2% and (●) their mixture. Lines are fits to the models: Equations for PEGDM and as described hereinbelow for mucin and mixture.

Mucoadhesion can also be confirmed by the appearance of aggregates in the mixture solution of the polymer and mucin. SAXS was used to detect aggregates formation within PEGDM/mucin mixture. Without being bound by any particular theory, solutions of PEGDM, mucin and their mixture were measured and the resulted SAXS curves were fitted to known models (FIG. 8). The scattering intensity is given by Equation 1:

$$I(q) = KP(q)S(q)$$

where K is a constant, P(q) is the form factor and S(q) is the structure factor calculated according to the Percus-Yevick approximation.

Moreover, and without being bound by any particular theory, a more complex model taking into account summation of the Ornstein-Zernike model and the Debye-Bueche model (Equation 2 below), which describes chain entanglements and aggregation, respectively, showed a good fit to the mucin, the PEGDM and their mixture solutions (FIG. 8).

$$P(q) = \frac{k_{net}}{1 + (q\xi_1)^2} + \frac{k_{agg}}{(1 + (q\xi_2)^2)^2}$$

where $\xi_1$ is the correlation length of the network, $\xi_2$ is the dimension of aggregates, $k_{net}$ is the constant of the network and $k_{agg}$ is the constant of the aggregates.

A comparison between the mucin and the mixture solutions (Table 3 below (showing the parameters of three solutions as described therein) demonstrate that there is no significant change in the parameters values, meaning no major change in the mesh size of the network and/or size of aggregates. However, the constant value related to the network decreased which may be resulted to from the amount of mucin due to sedimentation of larger aggregates.

TABLE 3

|  | PEGDM 2% | mix 1:1 | mucin 2% |
|---|---|---|---|
| network ξ | 12.537 | 21.242 | 29.039 |
| Aggregate ξ | 73.040 | 58.536 | 53.552 |
| kNetwork | 152.451 | 1613.342 | 4846.202 |
| kAggregate | 850.885 | 10000.000 | 9999.999 |
| Goodness of fit R² | 0.894 | 0.995 | 0.996 |

Figure 9:
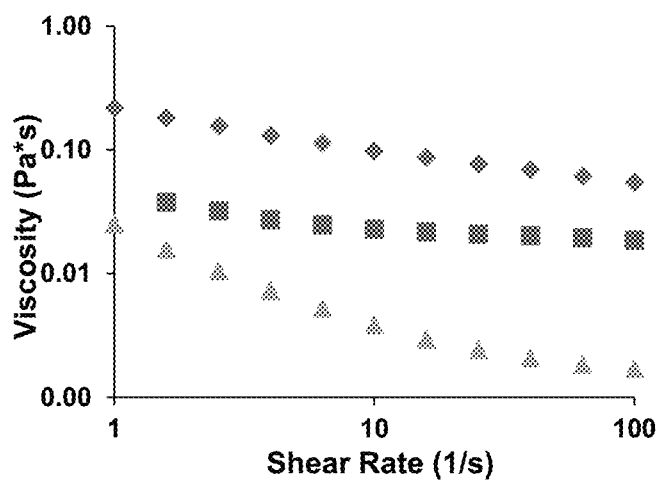
FIG. 9 presents graphs showing the viscosity vs. shear rate for alginate-SH-PEGM, mucin and their mixture in 0.1 M PBS at 37° C. Symbols: (♦) alginate-SH-PEGM/Mucin mixture, (■) mucin and (▲) alginate-SH-PEGM.

In addition, rheology measurements were performed to prove the existence of interactions between the mucin's glycoproteins and alginate-SH-PEGM. As observed in FIG. 9, the viscosity of alginate-SH-PEGM/mucin mixture is higher than the additive viscosity of these components separately. This result supports the hypothesis that alginate-SH-PEGM interacts with the mucin glycoproteins. It is suggested, without being bound by any particular mechanism, that those interactions are a result of Michael addition reaction and hydrogen bonding.

Optimization of Liposome-Containing Alginate Formulation

Figure 10A:
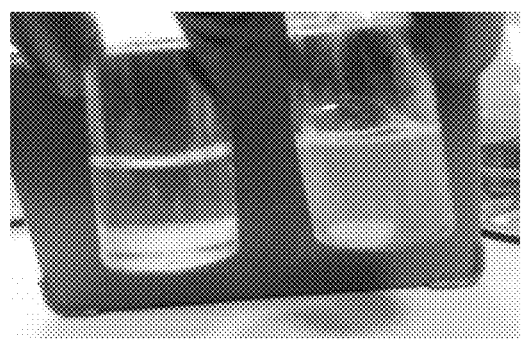
FIGS. 10A-B present experimental observation after 5 hr of incubation in 5% dextrose (left photograph) or in 0.01M PBS, pH=6.8 (right photograph) at 37° C.

The release rate of liposomes from alginate hydrogels was monitored. Alginate hydrogels were prepared as previously reported with $Ca^{+2}$ ions as the cross-linking reagent. The liposomes were mixed with the pre-gel solution, hence after curing remained trapped in alginate gels. The gels were incubated in 5% dextrose or PBS solution under shaking conditions at 37° C. The liposomes were marked with fluorescence dye and their release to the PBS or dextrose media was quantified (FIG. 10A).

Figure 10B:
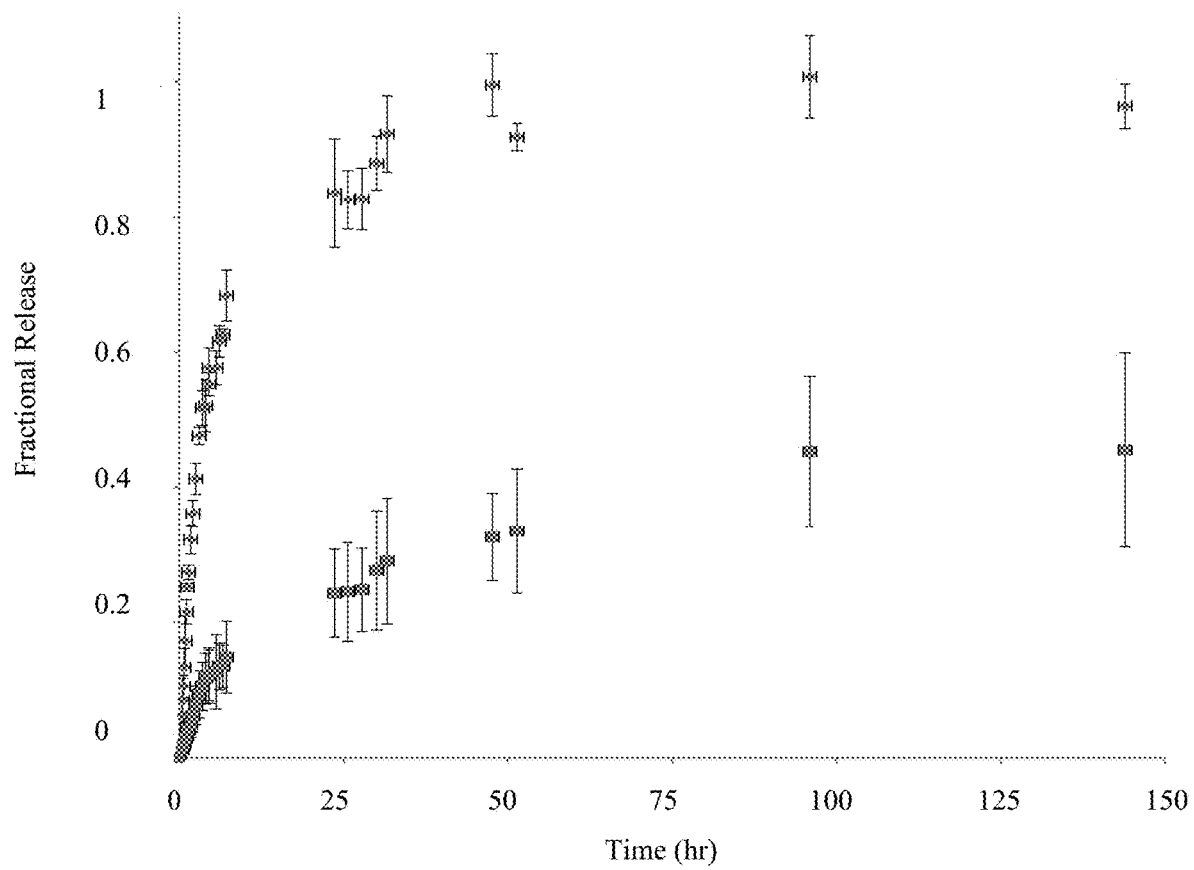

In 5% dextrose solution, the release rate was significantly slower compared to the buffer solution (FIG. 10B). Approximately 45% of the liposomes were released after a week, whereas, in buffer most of the liposomes were released at the first day.

Based on this results, alginate gels with ionic cross-linking were found to be potential candidates for sustained release of liposomes. Within 8 hours most of the liposomes were released (FIG. 10B). This is an optimal time for non invesive drug delivery in the oral cavity.

The release rate of the liposomes may be determined by the degradation rate of the polymeric matrix, the liposome's diffusion rate or a combination of both. Using biodegradable polymer as a drug carrier to specific site could be an advantage, since the polymer slowly degrades into non-toxic materials and releases the drug. In the experiments described herein, the liposome's mixture was released to external PBS solution which simulates the saliva fluids. It is known that alginate gels degrade due to chelation of calcium by phosphate ions.

Figure 11A:
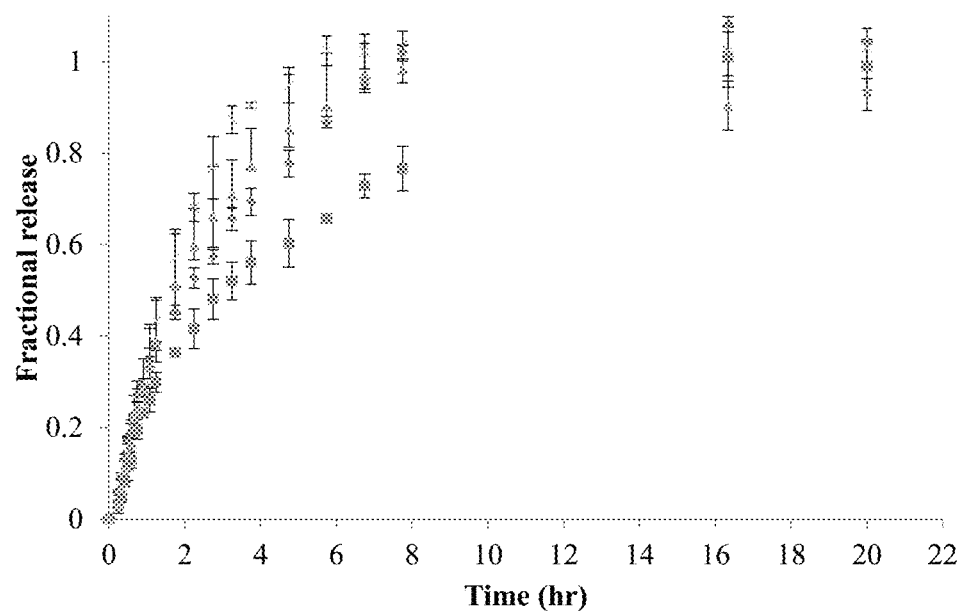
FIGS. 11A-C present an exemplary systems and results of release of liposomes vs. time.

Alginate gels with ionic cross-linking ($Ca^{2+}$) could be useful as a drug carrier if the diffusion of liposome into the cells is faster than the degradation rate of the polymeric matrix. In order to delay the degradation rate of the polymeric matrix, different compositions of alginate gels were prepared and the release rate of the liposomes from them was measured over time (FIG. 11A).

The amount of cross-linker used in the hybrid system determined the release rate of the liposomes and the mucoadhesion.

Figure 11B:
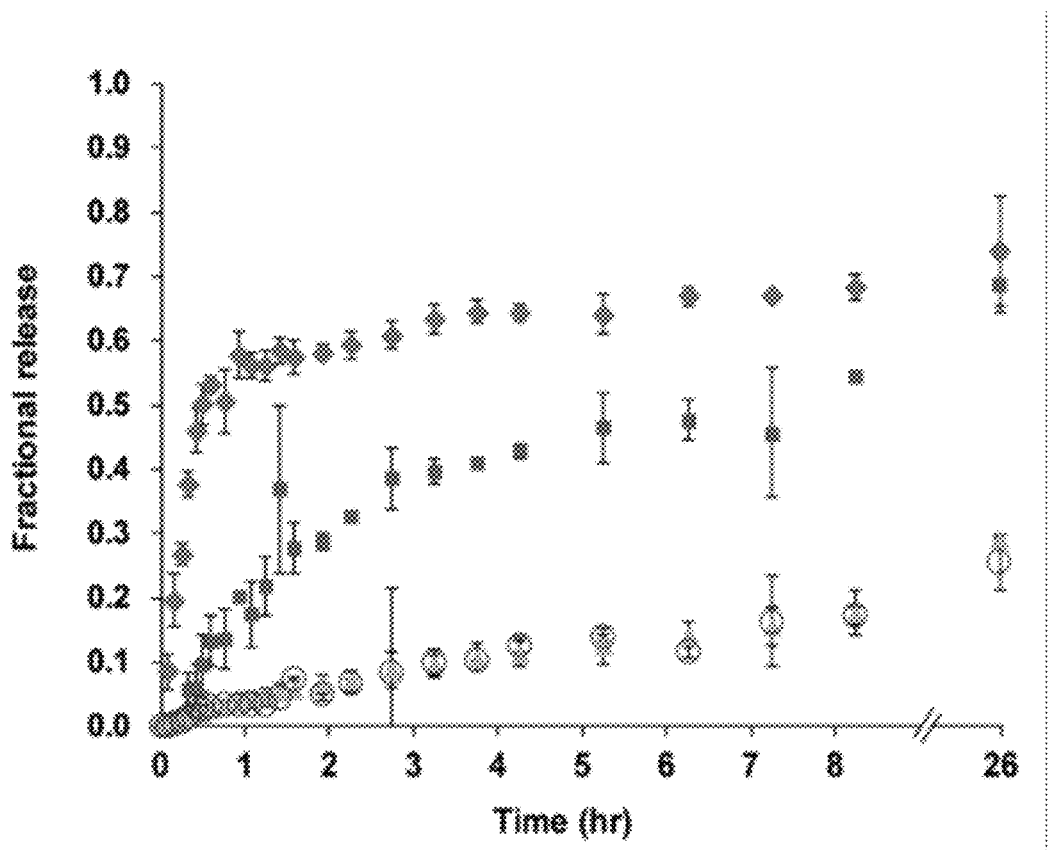

When hydrogels were created used 20% (v/v) cross-linker (in exemplary procedures: 19.5 mM $CaCl_2$ and 0.5 mM $BaCl_2$ mixture), which resulted in the optimal liposome release (FIG. 11B). However this formulation had lost its mucoadhesive properties.

Next, a cross-linked paste in which the non-cross linked paste is applied and then the cross linker solution (in exemplary procedures: 19.5 mM $CaCl_2$ and 0.5 mM $BaCl_2$ mixture) is added only on the top layer of the paste. The interface with the tissue must be kept as a none cross-linked paste to ensure the adhesion.

In exemplary procedures, for the application in oral cancer, a cap or a blocking agent is added prevent the release of the drug loaded liposome outwards.

Figure 11C:
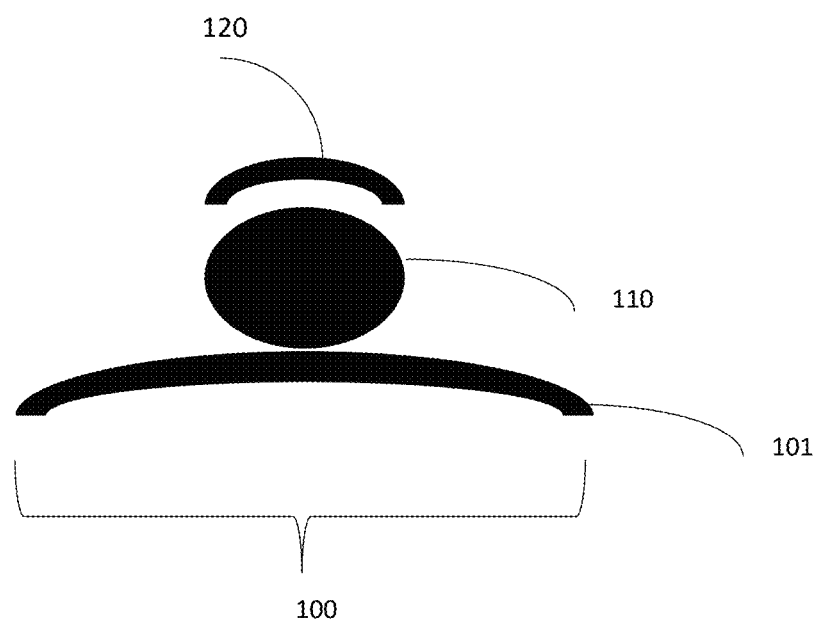

FIG. 11C presents a scheme of an exemplary hybrid polymer/liposomes system (100) as discloses herein. The first surface of polymeric matrix (110) is deposited on the tongue tissue (101) The cap (120) is deposited upwardly (i.e. on the second surface of the matrix opposite to the first surface of the matrix). The first surface of the matrix is characterized by higher mucoadhesiveness (i.e., less cross-linked) than the second surface adjacent to the cap (120). That is, in some embodiments, the portion of the matrix adjacent to the cap (120) is in the form of a hydrogel, and the portion of the matrix adjacent to the tongue tissue (101) is in the form of a paste (i.e. being less crosslinked).

The liposome release and the degradation rates of hydrogels formed from calcium cross-linking were slower by addition of divalent barium or strontium metal ions (observed during experiment). In addition, the rate of liposome release may be regulated by addition of different concentration of those ions. Controllable degradation rate was achieved, thus, controllable rates of liposome release.

Similar release rates were obtained in hydrogels with different concentration of alginate (1% or 3% alginate). In 1.33% alginate gel, the observed rate was slower compared to the 1% alginate gel. 1.33% alginate gel composed from the same amounts of all components as in 1% gel (alginate, cross-linking agent and liposome) in less amount of water, i.e., more concentrated. In addition, higher concentration of cross-linking agent (++1% hydrogel) slightly accelerated the release rate. These unexpected results are currently under investigation.

Figure 12:
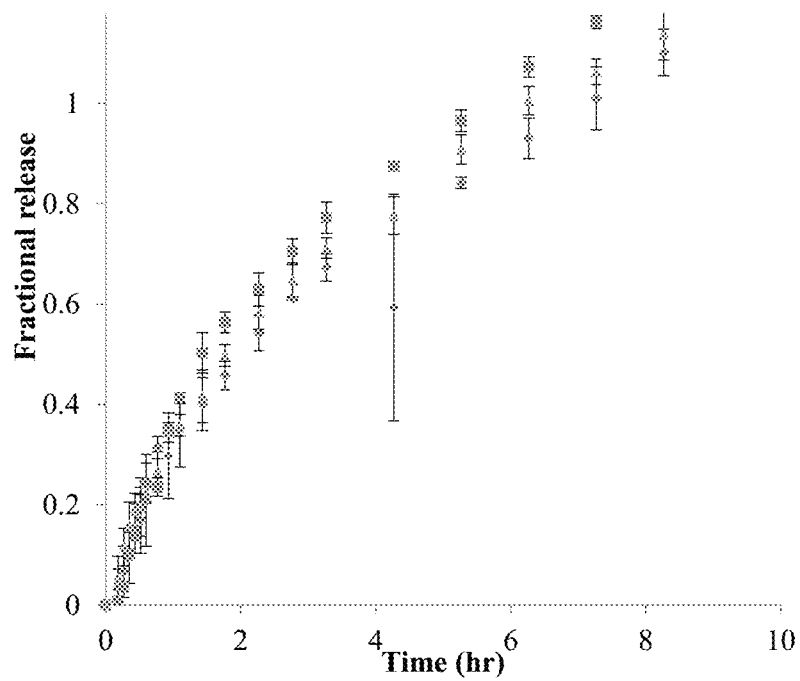
FIG. 12 presents a graph showing the fractional release of liposome vs. time from alginate hydrogels into 0.01M PBS, pH=6.8, at 37° C. (♦) 1% w/v alginate in high dextrose concentration within the hydrogel, (▲) 1% w/v alginate hydrogel-liposome concentration (0.025 M), and (■) 1% w/v alginate in high liposome concentration (0.033 M) within the hydrogel.

To further understand the factors affecting the release rate of the liposomes, the release rate was monitored with high concentration of liposomes (0.033M) or dextrose (dex) in the hydrogel. It is assumed that high concentration of dextrose may increase the osmotic pressure around the polymeric chains as a result the hydrogel may absorb water and accelerate the release of the liposome. The results are presented in FIG. 12.

Figure 13:
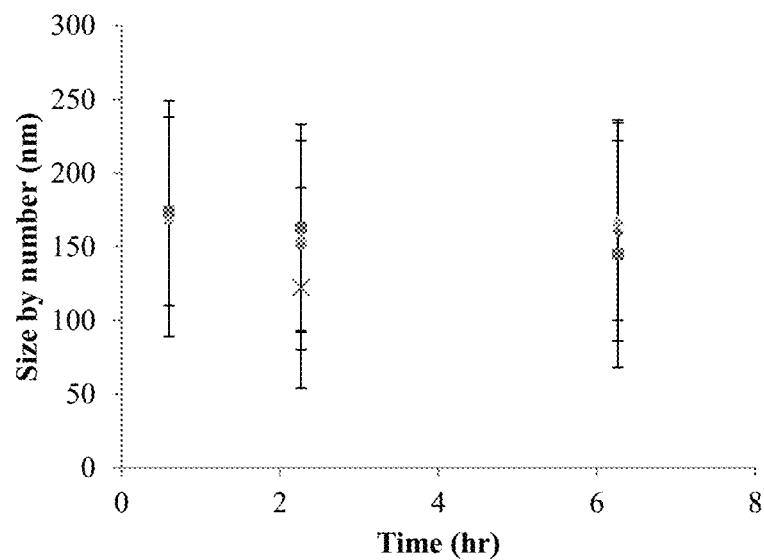
FIG. 13 shows a graphical presentation of the size distribution of the liposomes as a function of time. (♦) 1% w/v alginate in high dextrose concentration within the hydrogel, (▲) 1% w/v alginate hydrogel, and (■) 1% w/v alginate in high liposome concentration within the hydrogel, (x) 0.015 mmol of liposome in 10 mL buffer or dextrose solutions (no gel).

As seen in FIG. 13, higher concentrations of liposomes or dextrose did not influence liposome's release rate. In parallel to the release rate monitoring, the size distribution of the released liposomes was measured by DLS (see Table 4 below presenting DLS results of the released liposome's solution).

TABLE 4

| | Day/Time | By volume (nm) | By number (nm) |
|---|---|---|---|
| Original liposome solution | 1 | 227 | 185 ± 52 |
| In 0.01M PBS pH = 6.8 | 1, 0.5 hr, 1% high [lipo] | 266 | 174 ± 64 |
| | 1, 0.5 hr, 1% high [dex] | 285 | 169 ± 80 |
| | 1, 2.25 hr, 1% ord | 299 | 151 ± 71 |
| | 1, 2.25 hr, 1% high [lipo] | 290 | 163 ± 70 |
| | 1, 2.25 hr, 1% high [dex] | 279 | 157 ± 65 |
| | 1, 2.75 hr, control | 349 | 122 ± 68 |
| | 1, 6.166 hr, 1% ord | 288 | 160 ± 74 |
| | 1, 6.166 hr, 1% high [lipo] | 345 | 145 ± 77 |
| | 1, 6.166 hr, 1% high [dex] | 257 | 168 ± 68 |

DLS results show particles size in the range of 107-190 nm, similar to the original liposome solution that showed particles with a number average diameter of 185 nm. In addition, the size distribution of the liposome's release solutions was constant during the experiment. This result suggests that the liposomes are stable under experimental conditions.

Figure 14A:
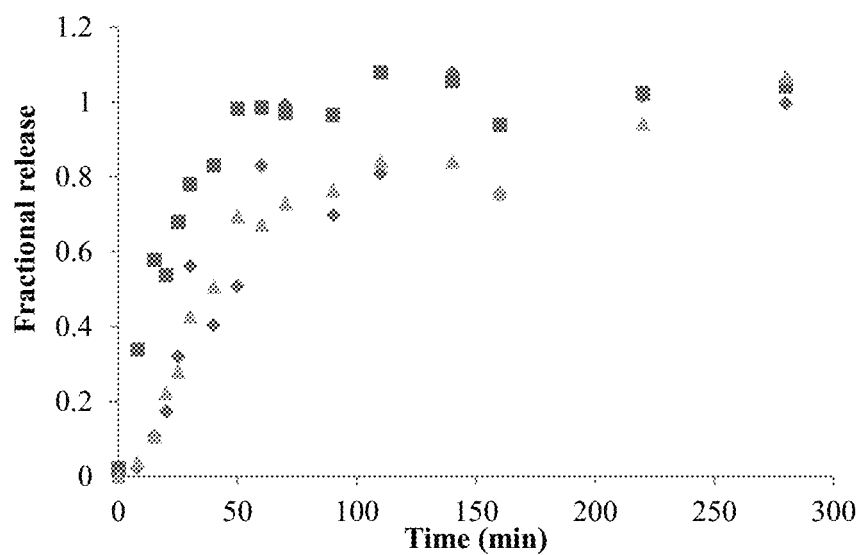

The rate of liposomes release from cross-linked alginate hydrogel was examined as well. Different alginate pastes were examined as alternative drug delivery system. Different alginate pastes were prepared and the rate of liposome's release from native, thiolated (SH) and acrylated (PEGAc) alginate pastes were monitored as shown in FIG. 14A. The rates for all polymeric pasts were nearly the same. Most of the liposomes were released within the first two hours of the experiment. Different concentrations of alginate pastes were prepared and the liposomes and polymeric chains release rates were monitored (FIG. 14B).

Figure 18B:
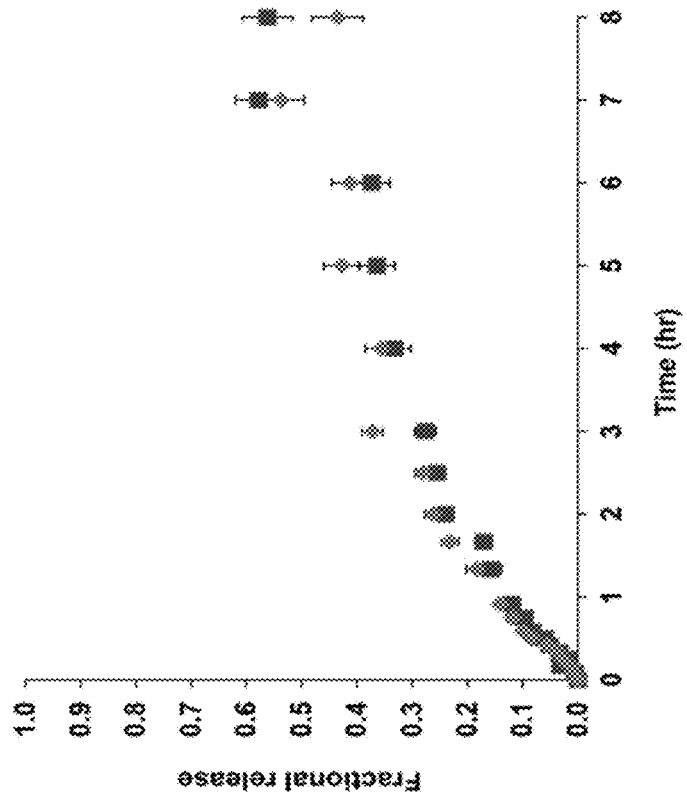
FIGS. 18A-B present graphs showing the fractional release of liposomes vs. time from alginate pastes and cross-linked alginate pastes into simulated saliva buffer, pH=6.8, at 37° C. (■) 3% alginate paste, (▲) 3% $Ca^{+2}$—$Ba^{+2}$ cross-linked alginate paste (FIG. 18A); fractional release of (♦) free Dox, (■) Dox liposomes vs. time from 3% $Ca^{+2}$—$Ba^{+2}$ cross-linked alginate pastes into simulated saliva buffer, pH=6.8, at 37° C.
Figure 18A:
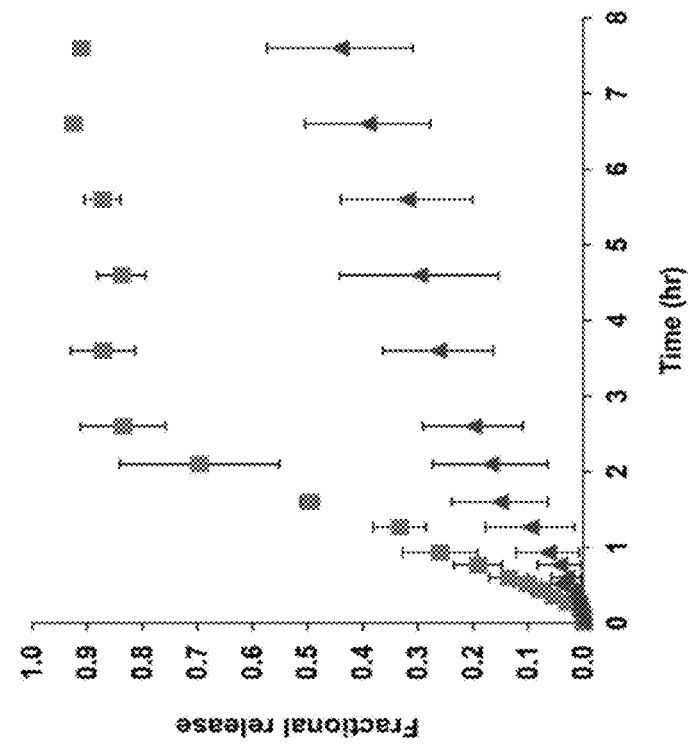

The paste concentration has insignificant impact of the on the liposome release rate. In addition, the liposome and the polymeric chains were released in a similar rate to the buffer solution (FIG. 18 C-E).

Protein Release from Liposomes in Alginate Formulations

Figure 15:
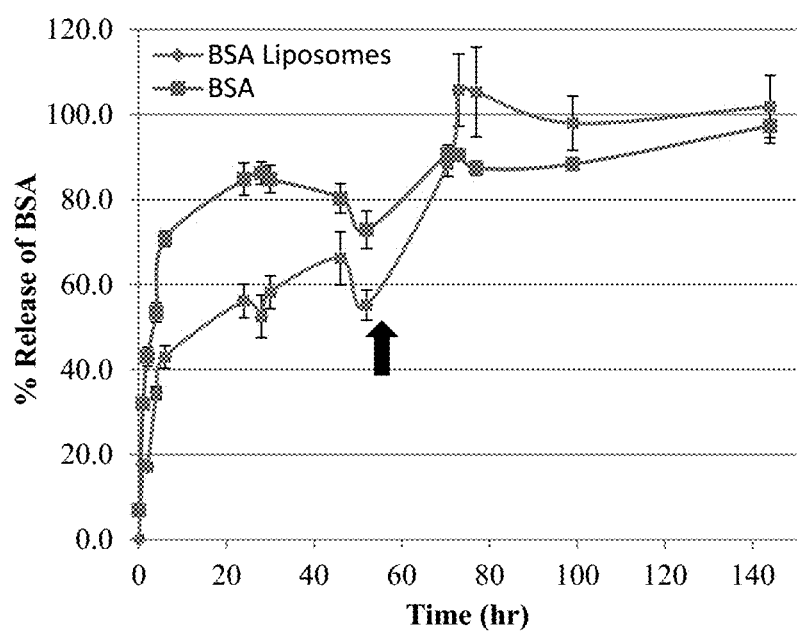
FIG. 15 presents graphs showing the release of BSA from alginate gel formulation over time while agitated in 10% PBS and then (see arrow) PBS, at 37° C. (♦) BSA in liposomes in alginate formulation, (■) Free BSA in alginate formulation. The black arrow shows the point in which the buffer was replaced from 10% PBS to PBS.

The release of a model protein, BSA, from liposomes in alginate formulations was measured. The alginate gels were initially agitated in 10% PBS for 24 hours after which the buffer was replaced by PBS in order to assess the release during the deterioration of the gel. The release over time is presented in FIG. 15.

As can be observed, the protein which is encapsulated in liposomes is released considerably slower than the free protein in alginate formulation. Without being bound by any particular mechanism, it is assumed that upon replacement of the buffer to PBS, the release is very fast in both samples due to the deterioration of the gel resulting from calcium chelation.

Example 4

Liposome Release Rate from Hybrid Chitosan Hydrogels

As described herein, hybrid chitosan hydrogels were prepared by cross-linking chitosan with 0.1% w/v genipin in pH of 4.5. These conditions lead to low cross-linking density and were chosen in order to obtain soft and sticky gels which may better adhere to the mucus surface. In addition, the expectation was that with lightly cross-linked system the swelling ability of the gel may increase and the liposomes would diffuse out more rapidly. However, the gels were shrunken during the experiment and the liposomes were not released to the buffer medium in these conditions (data not shown). It is assumed that the major reason for the observed de-swelling is the ionic strength of the release medium.

To further investigate this phenomenon, covalently cross-linked chitosan hydrogels with 0.1% w/v genipin at pH 4.5 were incubated in 0.01M PBS and in diluted PBS (10%) at pH 6.8 and 37° C. for 12 hr. Hydrogels which were incubated in 0.01M PBS solution shrunk during experiment, whereas, hydrogels which were incubated in diluted PBS solution initially swelled and absorbed water until the point that the polymeric network lost its integrity and decomposed.

In further exemplary procedures, less cross-linked hybrid chitosan hydrogels were prepared using 0.05% w/v genipin in two different pH values of 4.5 and 5.6. It was expected to find different swelling behavior of the two kinds of hydrogels, and consequently, different liposome release rate from them. However, only about 1% of liposomes were released to the external buffer solution after 24 hr in both hydrogels. Several reports estimated the turnover rate of the oral mucosal epithelium in the region of 2-6 days. Without being bound by any particular mechanism, this fact combined with the dilution factor of the saliva fluids, may lead to reduce absorption of the drug. Therefore, controlled release system in the oral cavity should be designed to release most of the active compound within the first two days.

Example 5

Liposome Release Rate from Hybrid Chitosan Pastes

The rate of liposome release from hybrid chitosan hydrogels was too slow to allow sufficient release of drug-containing liposomes near cancerous lesions. Therefore, the performance of hybrid non cross-linked viscous chitosan solutions, and chitosan paste was examined. Different concentrations (1%, 2% and 3% w/v) of chitosan pastes were prepared and spread on a porcine's tongue tissue. The rate of liposome release and concentration of polymer chains in the release medium were monitored.

Figure 16A:
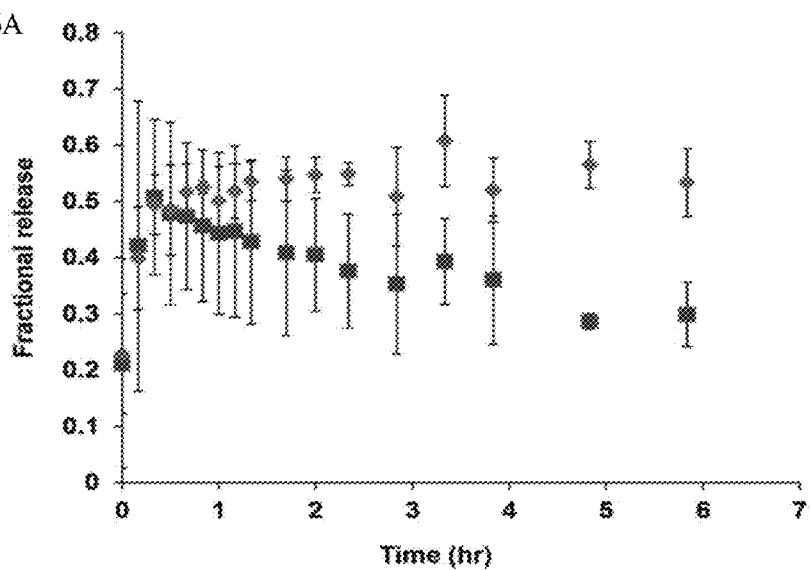
FIGS. 16A-C present graphs showing the fractional release of liposome and polymeric chains vs. time into simulated saliva buffer, pH=6.8, at 37° C. (♦) liposome release, (■) polymeric chain release. (a) 1% chitosan paste; (b) 2% chitosan paste; (c) 3% chitosan paste.
Figure 16B:
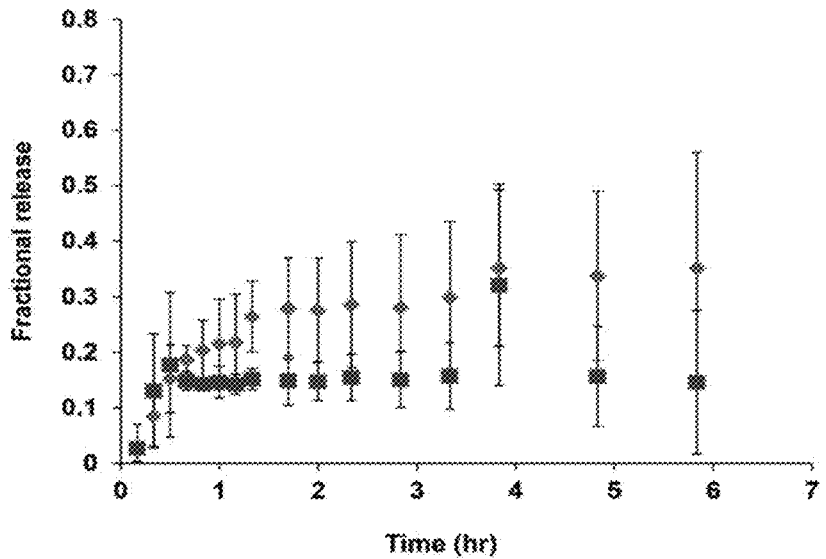
Figure 16C:
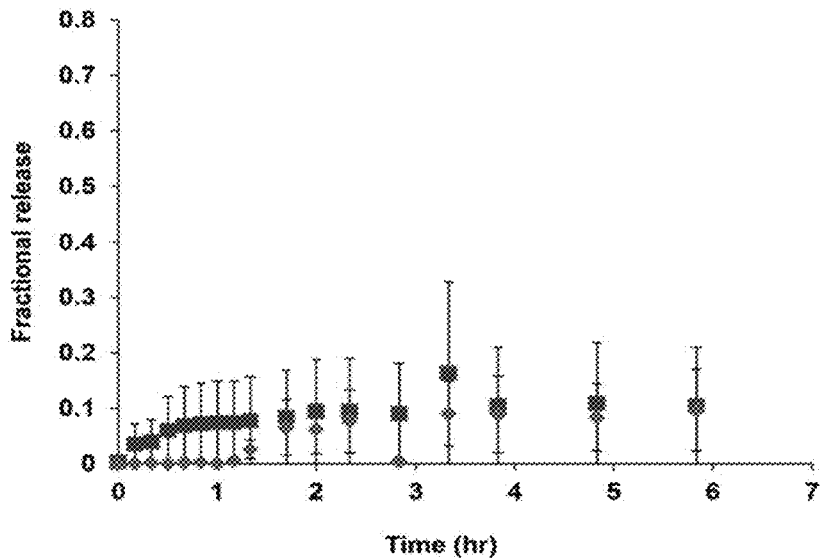

Liposomes release rate from polymeric matrix can be controlled by the diffusion rate of liposomes, polymeric chains dissociation or both. In order to understand the mechanism controlling the liposomes release, both polymeric chains and liposomes concentrations were monitored. The liposomes and polymeric chains exhibits similar release rates, may indicates that polymeric chains dissociation is fast process relative to free diffusion of liposomes out from the polymeric matrix. However, the rate of liposomes release from chitosan pastes is affected by the polymer concentration. At the highest concentration, 3% chitosan, (FIG. 16C) less than 1% of the liposomes were released during the first hour of the experiment, whereas, in 1% paste (FIG. 16A) approximately 50% was released. Importantly, the concentrations of both liposomes and polymer chains reaches fast to a plateau (~1 hr) and stay constant over the time (FIGS. 16A-C). This phenomenon is referred to as the in situ gelation of chitosan pastes. During the first hour the polymeric chains cross-linked, the polymeric pores decreased and make it difficult/block for the liposome to diffuse out.

In order to support this assumption, chitosan solutions 1%, 2%, 3% w/v cast into a silicon ring which was placed in a petri plate. Simulated saliva buffer solution (37° C., pH 6.8) was added, the plate closed and warmed to 37° C. overnight. Soft, tree-dimensional hydrogels were obtained in 2% and 3% chitosan solutions. After systematic evaluation of the buffer contents, it was concluded that the cross-linking is induced by the bicarbonate ions. Without bicarbonate ion tree-dimensional hydrogel was not received.

Example 6

Liposome Size and Stability

Figure 17:
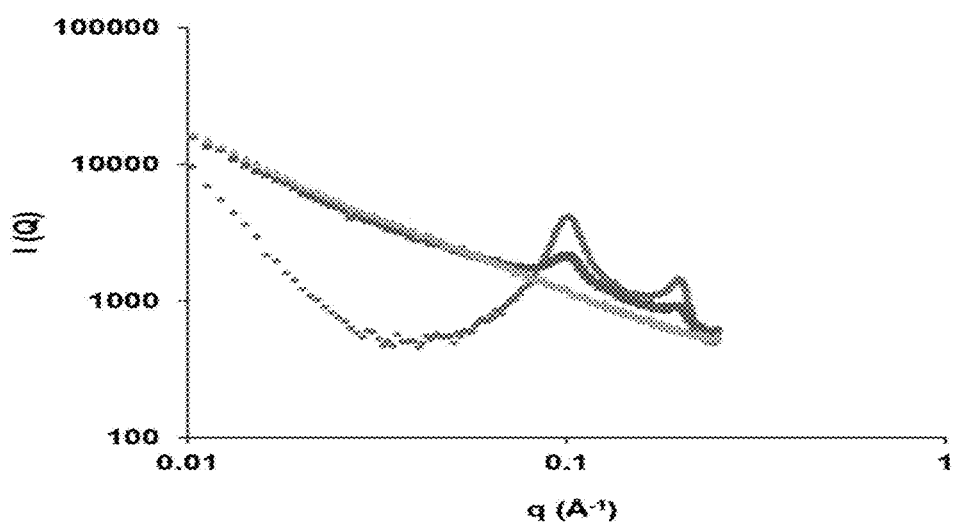
FIG. 17 presents graphs showing SAXS data collected for: (blue; upper curve in the right edge) 100 mM liposome solution; (red; middle curve in the right edge) 3% Alginate hydrogel with 25 mM liposome; (green; lower curve in the right edge) 3% Alginate hydrogel without liposome.

As described above, Liposome size distribution was measured by DLS. In addition, the size distribution of the liposome's release solutions was constant during the experiment; this result suggests that the liposomes are stable under experimental conditions. Moreover, SAXS measurements were carried out in order to examine the structural stability of the trapped liposome in alginate hydrogel (FIG. 17).

Two distinctive peaks of liposome were observed in the original liposome solution as well as in alginate hydrogel. The liposome retained its structural morphology in the polymeric matrix.

Example 7

Liposome Release Rate from Cross-Linked Alginate Pastes

In order to combine the mucoadhesive properties of alginate paste with the sustained release of the liposome from alginate hydrogel, the paste was cross-linked with mixture of $Ca^{+2}$—$Ba^{+2}$ solution on the porcine's tongue tissue surface, then, immersed into the buffer solution. The liposome release rate was monitored and compared to non-cross-linked alginate solution (see FIGS. 18A-B)

Cross-linking alginate paste on the tissue surface leads to improved adherence of the paste and sustain the liposome release from the polymeric matrix.

The cross-linked pastes for the release rate of doxorubicin (a clinically approved chemotherapeutic drug) were further examined. The release of drug loaded liposomes and free drug were similar, and sustained as observed for the empty liposomes.

Example 8

Polymer Retention Study

Flow through study was used as additional tool to evaluate the mucoadhesion of alginate pastes. Fluorescent labeled alginate paste was spread on a porcine tongue and washed away at a constant rate by a simulated saliva buffer. The analysis was performed by determining the polymer concentration in the eluting fluid. The adhesion of 3% alginate paste was compared to 3% cross-linked alginate paste.

Figure 19:
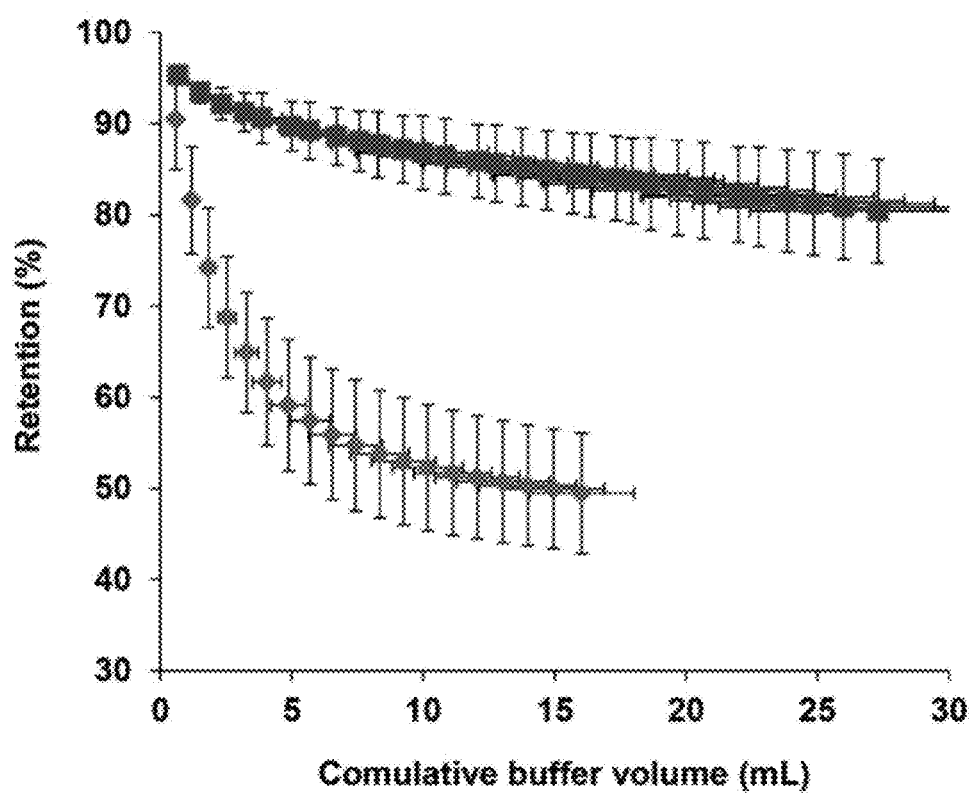
FIG. 19 presents graphs showing the mucoadhesion evaluation of (♦) 3% w/v, alginate paste; (■) 3% w/v, cross-linked alginate paste on porcine tongue.

The concentration of alginate in the collected buffer samples reached to a steady state of 50% retention after about 10 mL of eluting buffer. Although cross-linked alginate paste did not reach to equilibrium and the concentration constantly increased up to 80% retention after 27 mL of eluting buffer (FIG. 19). The clearance of cross-linked alginate paste is much slower than alginate paste; therefore, the adhesion is much stronger.

Example 9

The Efficacy of Drugs and Drug Loaded Liposomes

The Efficacy of Drugs and Drug Loaded Liposomes Towards HNSCC Cells (CAL-27)

Figure 20A:
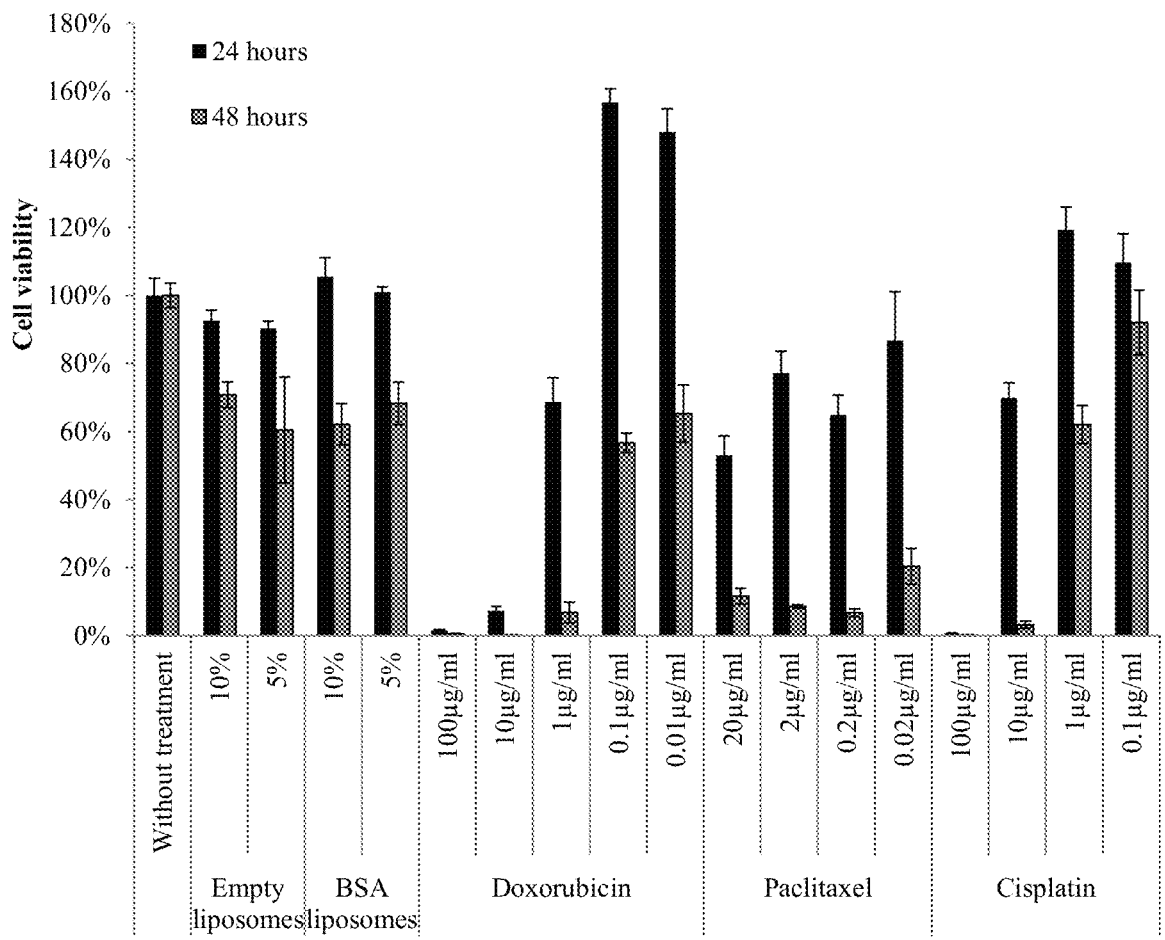
FIGS. 20A-B present bar graphs showing the cell viability of CAL-27 after 24 and 48 hr in the presence of empty liposomes, BSA, Doxorubicin, Paclitaxael, Cisplatin (FIG. 20A) 5-FU and Carboplatin (FIG. 20B). Cell viability was determined using the MTT assay. In each couple of bars in FIGS. 20, 21, and 27 the left one refers to 24 h and the right one refers to 48 h.
Figure 20B:
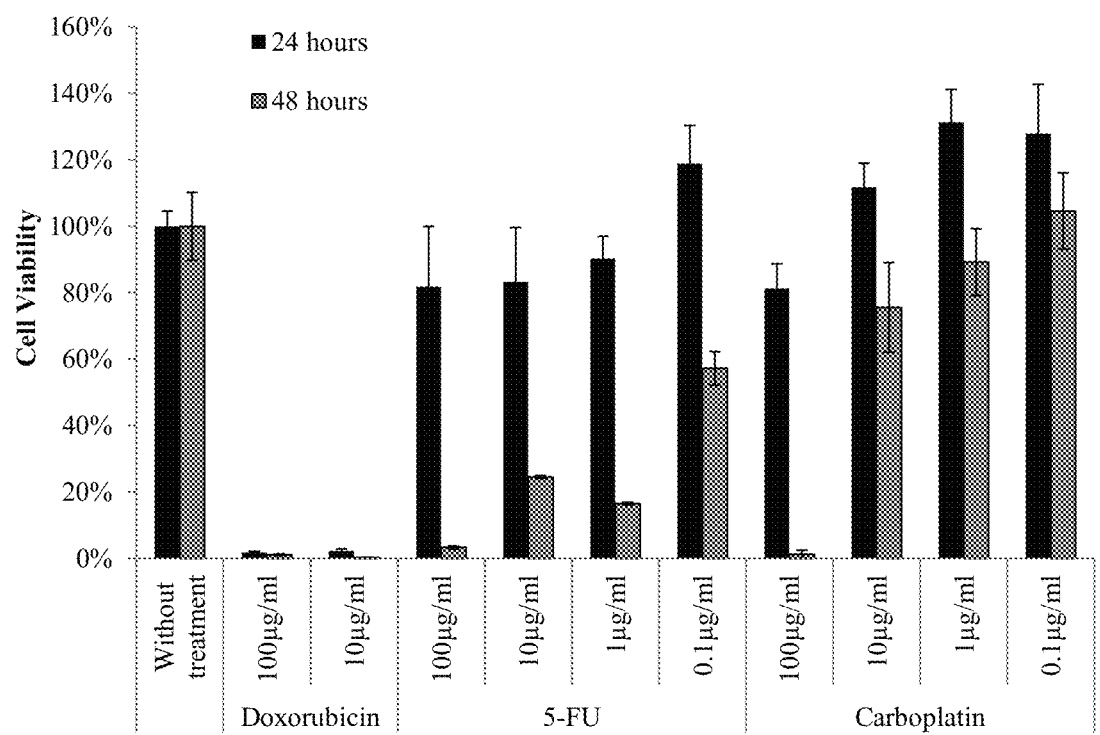
Figure 21A:
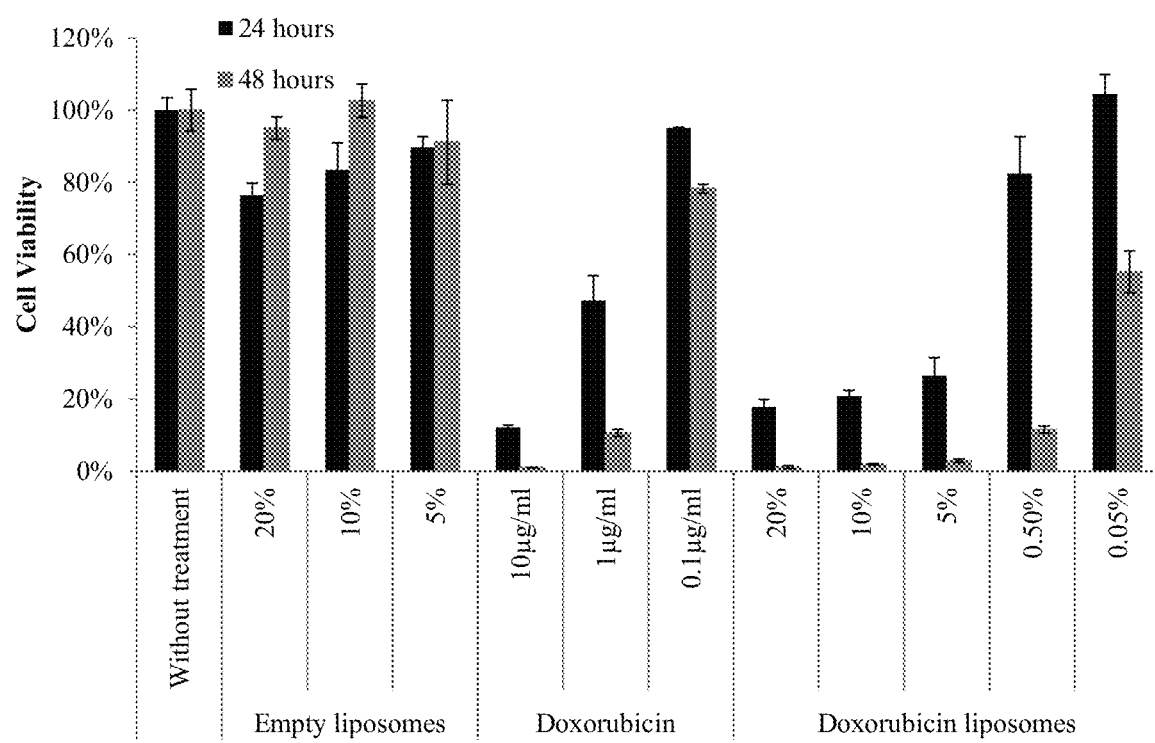
FIGS. 21A-B present bar graphs showing the cell viability of CAL-27 after 24 and 48 hr in the presence of drug loaded liposomes in comparison to free drug and empty liposomes (FIG. 21A); and cell viability in the presence of free Doxorubicin and loaded into liposomes (400 µg/ml), and 5-FU free and loaded into liposomes (FIG. 21B). Cell viability was determined using the MTT assay.
Figure 21B:
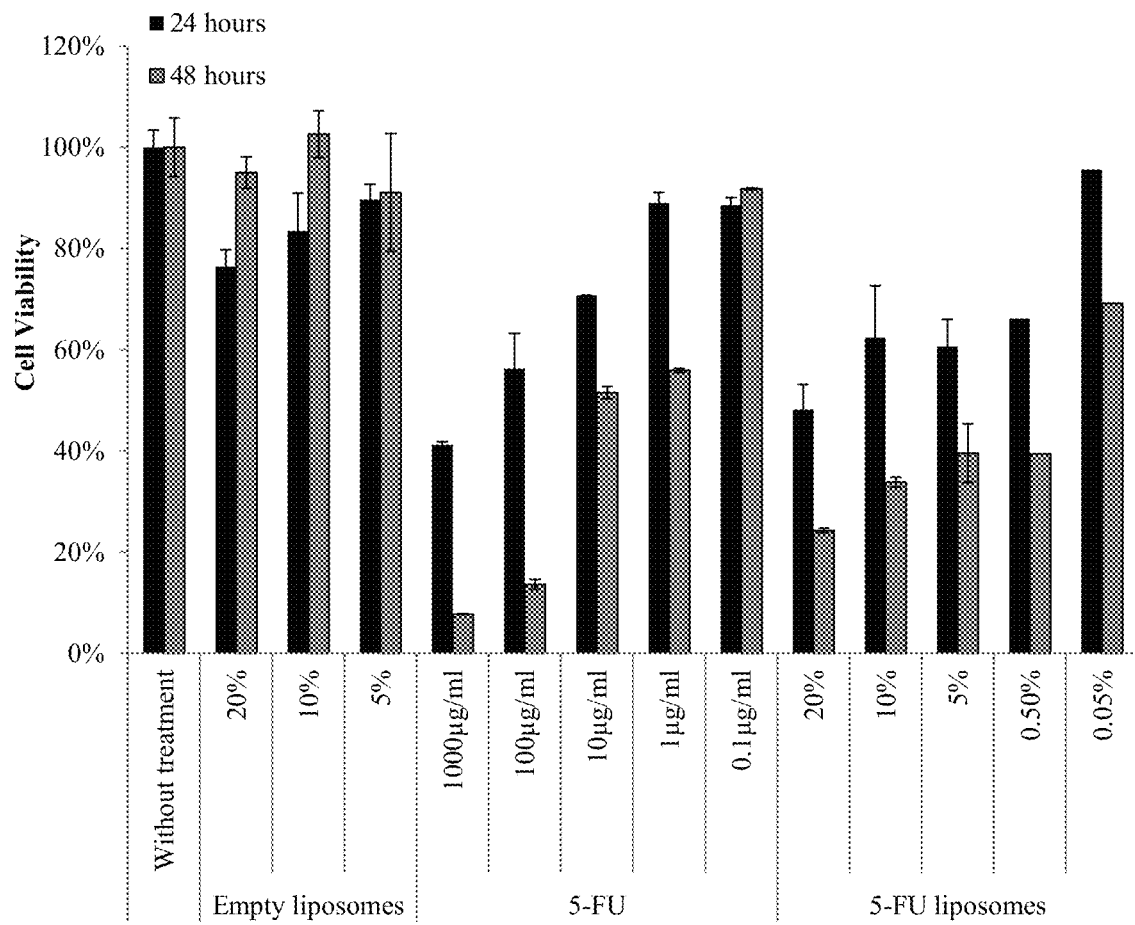

In order to examine the effectivity of the proposed hybrid system, in vitro experiments were initiated using an HNSCC cell line, CAL-27. First, the toxicity of empty liposomes, BSA loaded proteins and various concentrations of chemotherapeutic drugs, was tested using the MTT viability assay. Results are presented in FIGS. 20A-B. Based on the results obtained two chemotherapeutic drugs, doxorubicin and 5-FU, were encapsulated in liposomes and their toxicity was examined in comparison to the free drug. The Doxorubicin liposomes were very efficient in promoting cancer cell death, while 5-FU liposomes and free drug are slower in action and therefore seemed less efficient within the 48 hr experiment (FIGS. 21A-B).

Example 10

Protein Loaded Liposomes

The efficient encapsulation of proteins into liposomes is important to ensure drug potency. To study the delivery of proteins into cancer cells the model protein VGFP was first encapsulated into liposomes. Next, the encapsulation of the biological drug of choice, Cetuximab, a monoclonal antibody that targets the epidermal growth factor receptor (EGFR) was examined. Cetuximab is approved in many countries all over the world for treating patients with squamous cell carcinoma of the head and neck (SCCHN).

Table 5 below presents the encapsulation yield and properties for both VGFP and Cetuximab loaded liposomes.

TABLE 5

| Protein | Encapsulation Yield | Size (nm, DLS) | Polydistribution index |
|---|---|---|---|
| sfGFP | 30% | 159.2 | 0.065 |
| Erbitux | 12% | 156.1 | 0.056 |

It was able to encapsulate significant amounts of protein which can be used either as a diagnostic tool for examining delivery (GFP) or as treatment (Cetuximab).

Study of Cetuximab Binding to Cancer Cells Using Flow Cytometry

In order to examine the affinity of the Cetuximab to human tongue squamous cell carcinoma CAL-27 cells, the commercial antibody and its isotype control IgG antibody was fluorescently labeled.

Figure 22A:
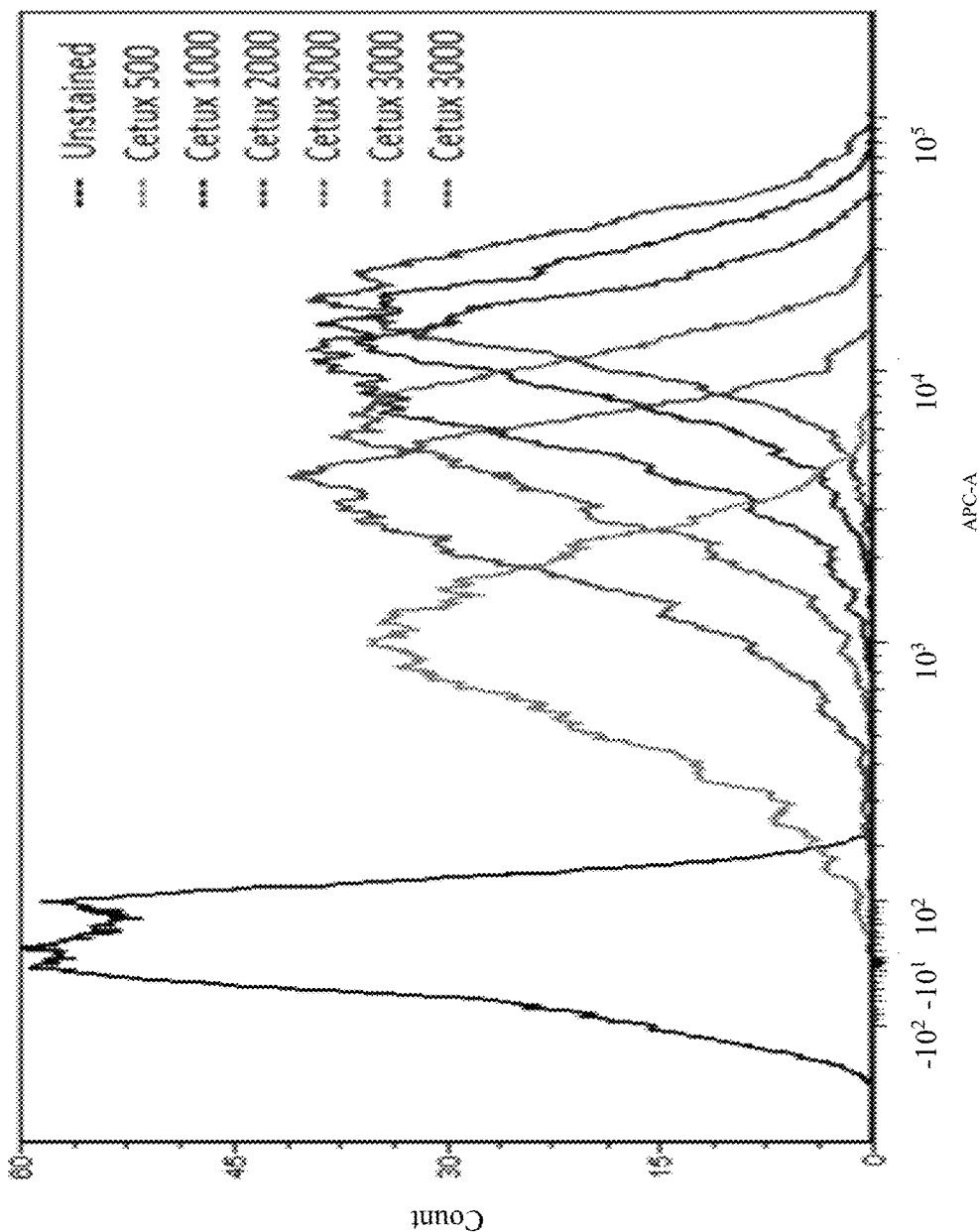
FIGS. 22A-E present graphs showing characterization of Cetuxibam binding to CAL-27 cells and normal human dermal fibroblasts (NHDF) cells using flow cytometry: chromatogram presenting the optimization of Cetuximab concentrations immunostaining of cells (bar graph.

To optimize the amount of antibody required, staining of CAL-27 cells with decreasing antibody concentration was examined using cell cytometry (FIG. 22A). Based on these results it was decided to use an antibody concentration of 1 µg/ml and 0.5 µg/ml for the following experiments.

Figure 22B:
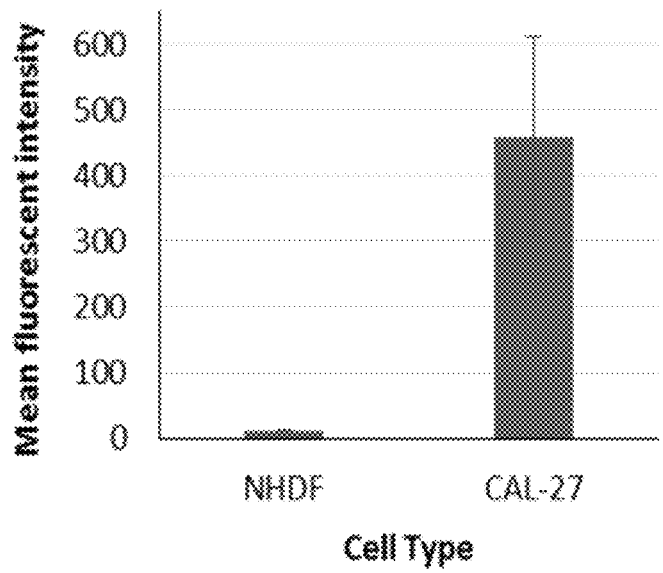
Figure 22C:
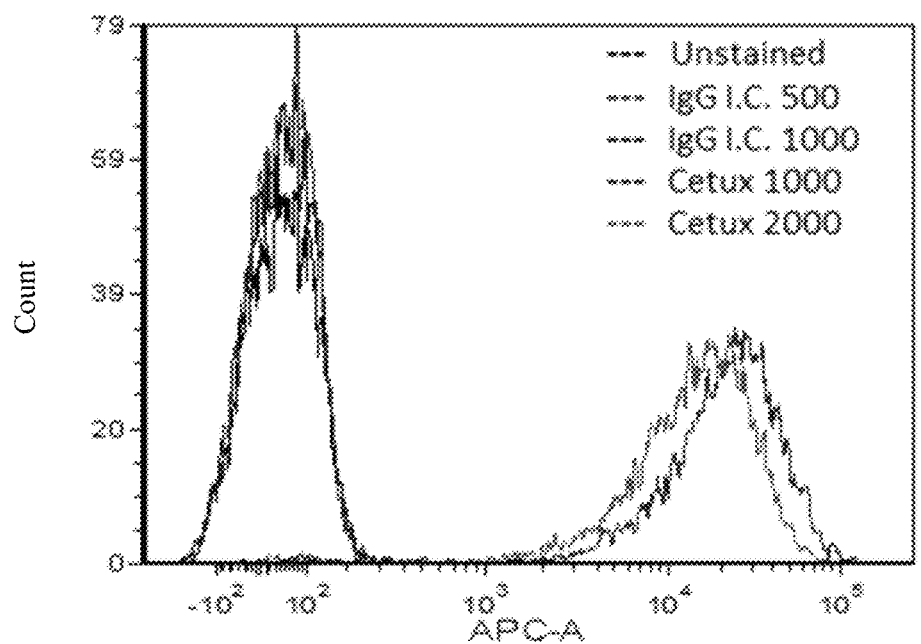
Figure 22D:
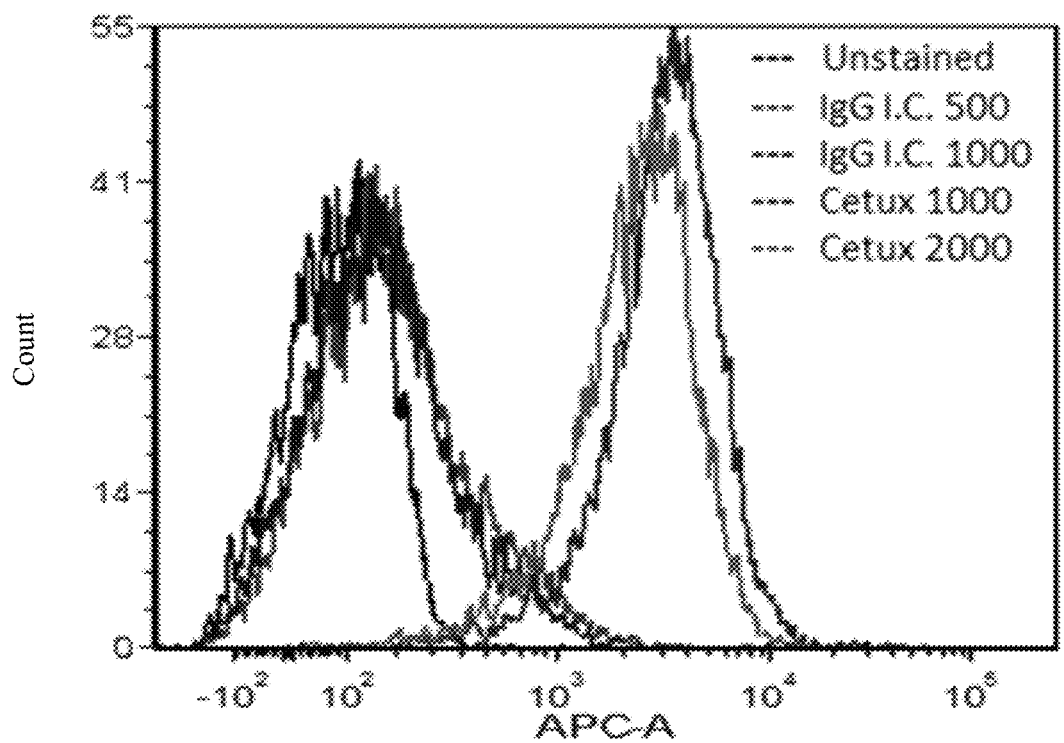

Next, the difference in antibody binding to normal human dermal fibroblasts (NHDF) versus cancer cells (CAL-27) was examined (FIG. 22B-D). The same concentrations of isotype control antibody were used. As expected, the intensity obtained for cancer cells was significantly higher than for NHDF, which indicated a very large amount of target sites, EGFR, on the cancer cell membrane.

Figure 22E:
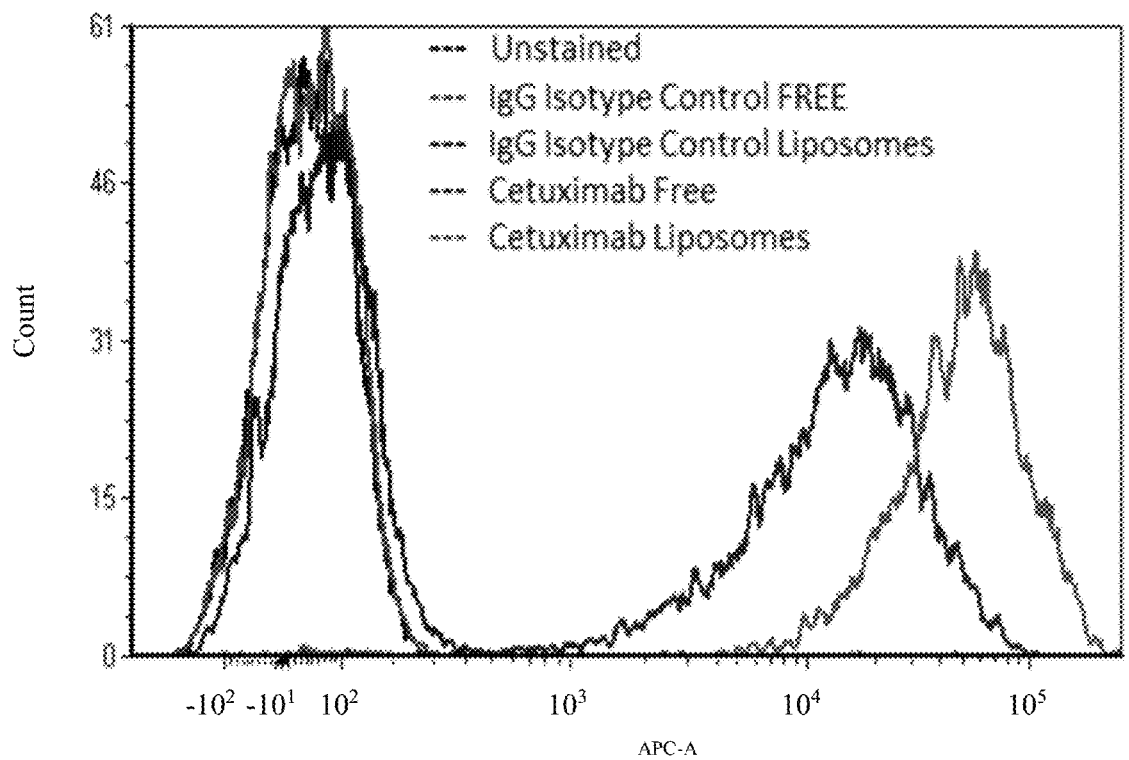

To examine the ability to deliver liposomes loaded with antibodies and to test the antibody affinity, CAL-27 cells were treated with Cetuximab loaded liposomes in comparison to IgG isotype control loaded liposomes and to free antibody (FIG. 22E). The Cetuximab loaded liposomes were delivered efficiently and the antibody was released and bound specifically. This proves the encapsulation process did not damage the potency of the drug. Liposomal delivery of proteins into cancer cells and to cancer cell membrane.

The ability of liposomes to deliver proteins to intra- and extracellular sites is essential for the efficiency of using them as treatment. Protein loaded liposomes were exposed to SCC 7 (murine) and CAL 27 (human) cancer cells and imaged using confocal microscopy. In order to view the delivery of proteins into cells, sfGFP loaded liposomes were used, while fluorescently labeled Cetuximab loaded into liposomes was used to examine the delivery to the cell membrane.

FIGS. 23A-G present the delivery of sfGFP loaded liposomes into SCC 7 cells and the delivery of Cetuximab loaded liposomes to CAL27 membranes.

Determination of Drug Penetration Through Tongue Tissue Using Franz Cell

The tongue is a relatively non permeable tissue. In order to examine the ability of the disclosed hybrid system to penetrate the basal layer and to deliver the drug to the cancer cells, the ability of free doxorubicin and doxorubicin loaded liposomes to penetrate using a Franz cell was assessed (FIGS. 24A-D).

The permeability enhancer phenylpiprazine (PPZ) effectively improved the penetration of free doxorubicin through the basal layer (FIG. 24C). When using liposomes, however, the doxorubicin did not penetrate through the tongue layer even in the presence of PPZ. This is probably due to the lipids that get trapped in the tissue, possibly within the cells.

Due to the fact that the SCC tumor penetrates the basal layer it may be hypothesized that the delivery of the liposomes will be possible when a tumor is present. This was tested further using in vivo animal models.

In Vitro Efficacy of Hybrid System (Alginate/Liposome)

In order to examine the effectivity of the proposed hybrid system, alginate pastes with empty liposomes, free drug and drugs loaded liposomes were tested for their effect on CAL-27 cells using permeable tissue culture inserts. Cell viability was determined using the Cell Titer-Glo® assay (see Table 6 below showing the relative cell viability obtained after 24 and 48 hr of treatment with hybrid system and FIG. 25).

TABLE 6

| | Relative cell viability 24 h | Relative cell viability 48 h |
|---|---|---|
| Empty liposome | 1.00 ± 0.033 | 1.00 ± 0.028 |
| Cisplatin liposome | 0.10 ± 0.016 | 0.02 ± 0.006 |
| 5FU liposome | 0.98 ± 0.032 | 1.01 ± 0.021 |

TABLE 6-continued

| | Relative cell viability 24 h | Relative cell viability 48 h |
|---|---|---|
| Doxorubicin liposome | 0.04 ± 0.003 | 0.01 ± 0.001 |
| Free Doxorubicin (100 μg/ml) | 0.04 ± 0.008 | 0.00 ± 0.000 |

The high potency of cisplatin and doxorubicin loaded liposomes released from the alginate paste was observed. 5FU loaded liposomes were not effective at all, and this is probably due to a very low to negligible encapsulation of the drug inside the liposomes. It can be seen that the doxorubicin liposomes are as effective as the free drug that is released as well from alginate paste and therefore it can be concluded that the hybrid system using alginate and liposomes is highly effective.

Animal Model Experiments to Assess Hybrid System Efficacy

The pre-clinical model is used for the assessment of the disclosed hybrid system as treatment for oral cancer is a squamous cell carcinoma (SCC) model in immunocompetent mice. The cancer cells are injected to the mice tongue and when a tumor is formed the hybrid system treatment is applied locally. Expect the tumor impairing the mice ability to feed and therefore a soft agar-based pallets using powdered food was developed (FIG. 26). In a preliminary experiment untreated healthy mice were fed with the agar-based food for about a week. Mice consumed the soft food normally without significant weight change and therefore this food was chosen as an alternative for mice with oral tumors.

Example 11

Toxicity of Hybrid System to HNSSC Cells

Using a human cell line derived from a tongue SCC (CAL-27) the toxicity of the drug loaded hybrid polymer/lipid system was examined. Alginate gels incorporating doxorubicin loaded liposomes were exposed to cells resulting in significant decrease in viability (FIG. 27). The alginate gels themselves and the gels with empty liposomes had no effect on the cells.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting.

The invention claimed is:

1. A composition comprising a polymeric matrix and one or more nano-carriers, wherein:
   (a) a first mucoadhesive surface of the polymeric matrix comprises a muco-adhesive polymer characterized by a volume by volume (v/v) crosslinking degree of less than 0.5%;
   (b) a second surface of the polymeric matrix comprises a muco-adhesive polymer characterized by a v/v crosslinking degree of at least 3%;
   (c) said one or more nano-carriers are entrapped within said polymeric matrix;
   (d) said one or more nano-carriers comprise at least one therapeutic or diagnostic agent, and wherein at least 0.5% to 60%, by total volume of said muco-adhesive polymer, are crosslinked via a crosslinking agent.

2. The composition of claim 1, being in the form of a muco-adhesive matrix, wherein said cross-linked muco-adhesive polymer defines a network having internal pores.

3. The composition of claim 2, wherein said one or more nano-carriers are entrapped within said internal pores.

4. The composition of claim 1, wherein said first mucoadhesive surface is characterized by a v/v crosslinking degree of less than 0.01%.

5. The composition of claim 1, comprising a blocking agent attached to said second surface, and wherein said blocking agent is adapted to inhibit said one or more nano-carriers from passing therethrough, and wherein said blocking agent is selected from the group consisting of polymeric and non-polymeric materials.

6. The composition of a claim 1, wherein said one or more nano-carriers further comprise a coupling agent attached thereto, optionally wherein said coupling agent is polyethylene glycol (PEG) or a derivative thereof.

7. The composition of claim 6, wherein at least 10% of said nano-carriers are linked to said muco-adhesive polymer via said coupling agent.

8. The composition of claim 1, wherein any one of: (i) said crosslinking agent is an ion selected from the group consisting of calcium, barium and strontium or a combination thereof; (ii) said muco-adhesive polymer is selected from the group consisting of: alginate, chitosan, or any derivative or a combination thereof.

9. The composition of claim 2, wherein an average diameter of said internal pores is at least 10% smaller than an average diameter of said one or more nano-carriers.

10. The composition of claim 1, wherein said muco-adhesive polymer is selected from: (i) a muco-adhesive polymer having attached thereto polyethylene (PEG); (ii) a bioerodible muco-adhesive polymer.

11. The composition of claim 1, wherein said one or more nano-carriers are lipid-based particles, optionally liposomes or micelles.

12. The composition of claim 1, wherein said one or more nano-carriers have an average diameter of about 50 to 500 nanometers.

13. The composition of claim 1, having a molar ratio of nano-carrier and polymer of 1:100 to 1:800.

14. The composition of claim 1, wherein said nano-carrier comprises 2-dimyristoyl-sn-glycero-3-phosphocholine (DMPC) and cholesterol, optionally wherein the DMPC and the cholesterol are in a ratio that ranges from 80:20 to 60:40, respectively.

15. The composition of claim 1, wherein any one of: (i) said therapeutic agent is characterized by having a therapeutic effect in the treatment of an oral cavity disease; (ii) said diagnostic agent is selected from the group consisting of: chromophores, fluorescent compounds, phosphorescent compounds, heavy metal clusters, radioactive labeling compounds and contrast agents.

16. The composition of claim 1, wherein the molar concentration of the nano-carriers is about 10-200 millimolar (mM).

\* \* \* \* \*